United States Patent
Haystead et al.

(10) Patent No.: US 10,000,469 B2
(45) Date of Patent: Jun. 19, 2018

(54) HEAT SHOCK PROTEIN 70 (HSP-70) RECEPTOR LIGANDS

(71) Applicant: Duke University, Durham, NC (US)

(72) Inventors: Timothy A. J. Haystead, Chapel Hill, NC (US); Khaldon Bodoor, Irbid (JO); Philip F. Hughes, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days. days.

(21) Appl. No.: 15/128,825

(22) PCT Filed: Mar. 25, 2015

(86) PCT No.: PCT/US2015/022555
§ 371 (c)(1),
(2) Date: Sep. 23, 2016

(87) PCT Pub. No.: WO2015/148714
PCT Pub. Date: Oct. 1, 2015

(65) Prior Publication Data
US 2017/0174660 A1    Jun. 22, 2017

Related U.S. Application Data

(60) Provisional application No. 61/970,339, filed on Mar. 25, 2014, provisional application No. 62/075,646, filed on Nov. 5, 2014, provisional application No. 62/048,133, filed on Sep. 9, 2014.

(51) Int. Cl.
*C07D 401/14* (2006.01)
*A61K 45/06* (2006.01)
*A61K 31/497* (2006.01)

(52) U.S. Cl.
CPC .......... *C07D 401/14* (2013.01); *A61K 31/497* (2013.01); *A61K 45/06* (2013.01)

(58) Field of Classification Search
CPC combination set(s) only.
See application file for complete search history.

(56) References Cited

U.S. PATENT DOCUMENTS

| | | | |
|---|---|---|---|
| 5,260,291 A | 11/1993 | Lunt et al. | |
| 5,747,498 A | 5/1998 | Schnur et al. | |
| 2008/0139587 A1 | 6/2008 | Huang et al. | |
| 2013/0158019 A1 | 6/2013 | Bryan et al. | |

FOREIGN PATENT DOCUMENTS

| | | |
|---|---|---|
| CA | 2093203 | 10/1993 |
| EP | 0520722 | 12/1992 |
| EP | 0564409 | 10/1993 |
| EP | 0566226 | 10/1993 |
| EP | 0837063 | 10/1996 |
| EP | 0787722 | 8/1997 |
| WO | WO 96/33980 | 10/1996 |
| WO | WO 97/02266 | 1/1997 |
| WO | WO 97/30034 | 8/1997 |
| WO | WO 97/38983 | 10/1997 |
| WO | WO 97/49688 | 12/1997 |
| WO | WO 98/10767 | 3/1998 |
| WO | WO 99/03854 | 1/1999 |
| WO | WO 02/22577 | 3/2002 |
| WO | WO 03/013541 | 2/2003 |
| WO | WO 03/041708 | 5/2003 |

OTHER PUBLICATIONS

Afanasyeva et al. (2007). Drug-induced Myc-mediated apoptosis of cancer cells is inhibited by stress protein Hsp70. International journal of cancer Journal international du cancer 121, 2615-2621.
Barrott et al. (2013). Optical and radioiodinated tethered hsp90 inhibitors reveal selective internalization of ectopic hsp90 in malignant breast tumor cells. Chemistry & biology 20, 1187-1197.
Beere (2001). Stressed to death: regulation of apoptotic signaling pathways by the heat shock proteins. Science's STKE, 7 pages.
Beere et al. (2000). Heat-shock protein 70 inhibits apoptosis by preventing recruitment of procaspase-9 to the Apaf-1 apoptosome. Nature cell biology 2, 469-475.
Blazer et al. (2010). Reversible, allosteric small-molecule inhibitors of regulator of G protein signaling proteins. Molecular pharmacology 78, 524-533.
Braunstein et al. (2011). Antimyeloma Effects of the Heat Shock Protein 70 Molecular Chaperone Inhibitor MAL3-101. Journal of oncology 2011, 232037.
Britten et al. (2000). A phase I and pharmacokinetic study of the mitochondrial-specific rhodacyanine dye analog MKT 077. Clinical cancer research: an official journal of the American Association for Cancer Research 6, 42-49.
Bulinski (1997) "Overexpression of MAP4 inhibits organelle motility and trafficking in vivo", J. Cell Sci. 110:3055-3064.
Carlson et al. (2013). Fluorescence Linked Enzyme Chemoproteomic Strategy for Discovery of a Potent and Selective DAPKI and ZJPK Inhibitor. ACS chemical biology, 8, 2715-2723.
Cummings et al. (2006). Universal screening methods and applications of Thermo Fluor. Journal of biomolecular screening 11, 854-863.
Daugaard et al. (2007). The heat shock protein 70 family: Highly homologous proteins with overlapping and distinct functions. FEBS letters 581, 3702-3710.
Dix et al. (1996). Targeted gene disruption of Hsp70-2 results in failed meiosis, germ cell apoptosis, and male infertility. Proceedings of the National Academy of Sciences of the United States of America 93, 3264-3268.

(Continued)

*Primary Examiner* — Brian E McDowell
(74) *Attorney, Agent, or Firm* — Michael Best & Friedrich LLP

(57) ABSTRACT

Inducible HSP70 is overexpressed in a wide spectrum of human tumors and its expression correlates with metastasis and poor outcomes to radiation and chemotherapy in patients. Identification of small molecule inhibitors of HSP70 pose a new therapy to cancer treatment. HS72, a benzimidazole piperidinyl carboxamide has been identified as an allosteric inhibitor for HSP70 and has demonstrated good tumor growth inhibition in vivo.

10 Claims, 31 Drawing Sheets

(56) References Cited

OTHER PUBLICATIONS

Evans et al. (2010). Heat shock protein 70 (hsp70) as an emerging drug target. Journal of medicinal chemistry 53, 4585-4602.
Fewell et al. (2001). Identification of an inhibitor of hsc70-mediated protein translocation and ATP hydrolysis. The Journal of biological chemistry 276, 910-914.
Fewell et al. (2004). Small molecule modulators of endogenous and co-chaperone-stimulated Hsp70 ATPase activity. The Journal of biological chemistry 279, 51131-51140.
Goloudina et al. (2012). Inhibition of HSP70: a challenging anticancer strategy. Cancer letters 325, 117-124.
Grosdidier et al. (2011). Fast docking using the CHARMM force field with EADock DSS. Journal of computational chemistry, 2149-2159.
Grosdidier et al. (2011). SwissDock, a protein-small molecule docking web service based on EADock Dss. Nucleic acids research 39, W270-277.
Guo et al. (2005). Abrogation of heat shock protein 70 induction as a strategy to increase antileukemia activity of heat shock protein 90 inhibitor 17-allylamino-demethoxy geldanamycin. Cancer research 65, 10536-10544.
Guo et al. (2005b). Mechanistic role of heat shock protein 70 in Bcr-Abl-mediated resistance to apoptosis in human acute leukemia cells. Blood 105, 1246-1255.
Haystead et al. (1993). Gamma-phosphate-linked ATP-sepharose for the affinity purification of protein kinases. Rapid purification to homogeneity of skeletal muscle mitogenactivated protein kinase kinase. European Journal of Biochemistry FEBS 214, 459-467.
Hughes et al. (2012). A highly selective Hsp90 affinity chromatography resin with a cleavable linker. Bioorganic & medicinal chemistry 20, 3298-3305.
Hunt et al. (1985). Conserved features of eukaryotic hsp70 genes revealed by comparison with the nucleotide sequence of human hsp70. Proceedings of the National Academy of Sciences of the United States of America 82, 6455-6459.
International Search Report and Written Opinion for Application No. PCT/US2015/022555 dated Jun. 25, 2015 (13 pages).
Jego et al. (2013). Targeting heat shock proteins in cancer. Cancer letters 332, 275-285.
Juhasz et al. (2013). The complex function of hsp70 in metastatic cancer. Cancers 6, 42-66.
Kang et al. (2008). Design of a fluorescence polarization assay platform for the study of human Hsp70. Bioorganic & medicinal chemistry letters 18, 3749-3751.
Leu et al. (2009). A small molecule inhibitor of inducible heat shock protein 70. Molecular cell 36, 15-27.
Massey (2010). ATPases as drug targets: insights from heat shock proteins 70 and 90. Journal of medicinal chemistry 53, 7280-7286.
Massey et al. (2010). A novel, small molecule inhibitor of Hsc70/Hsp70 potentiates Hsp90 inhibitor induced apoptosis in HCT 116 colon carcinoma cells. Cancer chemotherapy and pharmacology 66, 535-545.
Mayer et al. (2005). Hsp70 chaperones: cellular functions and molecular mechanism. Cellular and molecular life sciences : CMLS 62, 670-684.
Miyata et al. (2012). Cysteine reactivity distinguishes redox sensing by the heat-inducible and constitutive forms of heat shock protein 70. Chemistry & biology 19, 1391-1399.
Miyata, Y., Chang, L., Bainor, A., McQuade, T.J., Walczak, C.P., Zhang, Y., Larsen, M.J., Kirchhoff, P., and Gestwicki, J.E. (2010). High-throughput screen for Escherichia coli heat shock protein 70 (Hsp70/DnaK): ATPase assay in low vol. By exploiting energy transfer. Journal of biomolecular screening 15, 1211-1219.
Muhlradt (1997) "Epothilone B Stabilizes Microtubuli of Macrophages Like Taxol without Showing Taxol-like Endotoxin Activity," Cancer Res. 57:3344-3346.
Neef et al. (2010). Modulation of heat shock transcription factor 1 as a therapeutic target for small molecule intervention in neurodegenerative disease. PLoS biology 8, e 1000291.

Nicolaou (1997) "Synthesis of epothilones A and B in solid and solution phase," Nature 387:268-272.
Niesen et al. (2007). The use of differential scanning fluorimetry to detect ligand interactions that promote protein stability. Nature protocols 2, 2212-2221.
Nylandsted et al. (2002). Eradication of glioblastoma, and breast and colon carcinoma xenografts by Hsp70 depletion. Cancer research 62, 7139-7142.
Panda (1996) "Differential Effects of Vinblastine on Polymerization and Dynamics at Opposite Microtubule Ends", J. Biol. Chem. 271 :29807-29812.
Panda (1997) "Stabilization of microtubule dynamics by estramustine by binding to a novel site in tubulin: a possible mechanistic basis for its antitumor action ," Proc. Natl. Acad. Sci. USA 94:10560-10564.
Parcellier et al., "Heat shock proteins, cellular chaperones that modulate mitochondrial cell death pathways." Biochemical and biophysical research communications 304, 505-512 (2003).
Park et al. (2001). Hsp72 functions as a natural inhibitory protein of c-Jun N-terminal kinase. The EMBO journal 20, 446-456.
Pettersen et al. (2004). UCSF Chimera—a visualization system for exploratory research and analysis. Journal of computational chemistry 25, 1605-1612.
Powers et al. (2008). Dual targeting of HSC70 and HSP72 inhibits HSP90 function and induces tumorspecific apoptosis. Cancer cell I 4, 250-262.
Powers et al. (2009). Death by chaperone: HSP90, HSP70 or both? Cell Cycle 8, 518-526).
Powers et al. (2010). Targeting HSP70: the second potentially druggable heat shock protein and molecular chaperone? Cell Cycle 9, 1542-1550.
PubChem CID 38790029 created May 29, 2009.
Qi et al. (2013). Allosteric opening of the polypeptide-binding site when an Hsp70 binds ATP. Nature structural & molecular biology 20, 900-907.
Ramos, "Molecular charperones and protein quality control." Protein and peptide letters 18, 100 (2011).
Rodina et al. (2013). Identification of an allosteric pocket on human hsp70 reveals a mode of inhibition of this therapeutically important protein. Chemistry & biology 20, 1469-1480.
Rowlands et al. (2010). Detection of the ATPase activity of the molecular chaperones Hsp90 and Hsp72 using the TranscreenerTM ADP assay kit. Journal of biomolecular screening 15, 279-286.
Schlecht et al. (2013). Functional analysis of Hsp70 inhibitors. PloS one 8, e78443.
Seguin et al. (2012). A screen for modulators of large T antigen's ATPase activity uncovers novel inhibitors of Simian Virus 40 and BK virus replication. Antiviral research 96, 70-81.
She et al. (2008). Breast tumor cells with PI3K mutation or HER2 amplification are selectively addicted to Akt signaling. PloS one 3, e3065.
Shu et al. (2008). HSP70s: From Tumor Transformation to Cancer Therapy. Clinical medicine Oncology 2, 335-345.
Swain et al. (2007). Hsp70 chaperone ligands control domain association via an allosteric mechanism mediated by the interdomain linker. Molecular cell 26, 27-39.
Tan et al. (2011). GRP78 up-regulation is associated with androgen receptor status, Hsp70-Hsp90 client proteins and castrate-resistant prostate cancer. The Journal of pathology 223, 81-87.
Taneja et al. (2009). MMTV mouse models and the diagnostic values of MMTV-like sequences in human breast cancer. Expert review of molecular diagnostics 9, 423-440.
Tavaria et al. (1996). A hitchhiker's guide to the human Hsp70 family. Cell stress & chaperones 1, 23-28.
Vasquez et al. (1997) Nanomolar concentrations of nocodazole alter microtubule dynamic instability in vivo and in vitro. Mol. Biol. Cell. 8:973-985.
Wacker et al. (2009). Loss of Hsp70 exacerbates pathogenesis but not levels of fibrillar aggregates in a mouse model of Huntington's disease. The Journal of neuroscience: the official journal of the Society for Neurosci.ence 29, 9104-9114.

(56) References Cited

OTHER PUBLICATIONS

Wisen et al. (2008). Identification of small molecules that modify the protein folding activity of heat shock protein 70. Analytical biochemistry 374, 371-377.

Wyttenbach et al. (2001). Polyglutamine expansions cause decreased CREmediated transcription and early gene expression changes prior to cell death in an inducible cell model of Huntington's disease. Human molecular genetics 10, 1829-1845.

Yang et al. (2012). Hsp70 promotes chemoresistance by blocking Bax mitochondrial translocation in ovarian cancer cells. Cancer letters 321, 137-143.

Zeng et al. (2004). Hsp70 dynamics in vivo: effect of heat shock and protein aggregation. Journal of cell science 117, 4991-5000.

Howe et al., "Identification of an allosteric small-molecule inhibitor selective for the inducible form of heat shock protein 70," Chem Biol. Author Manuscript Published Online Dec. 11, 2014 Final Edited Form Published Dec. 18, 2014; 21(12):1648-59. doi: 10.1016/j.chembiol.2014.10.016. (55 pages).

chemical Abstracts Search Report for Ca No. 1118861-60-1, Jan. 16, 2018 (5 pp.).

C.

HEAT SHOCK PROTEIN 70 (HSP-70) RECEPTOR LIGANDS

CROSS-REFERENCE TO RELATED APPLICATIONS

This application is a U.S. national stage filing under 35 U.S.C. 371 of International Application No. PCT/US2015/022555, filed Mar. 25, 2015, which application claims priority to U.S. Provisional Patent Application No. 61/970,339, filed Mar. 25, 2014; U.S. Provisional Patent Application No. 62/048,133, filed Sep. 9, 2014; and U.S. Provisional Patent Application No. 62/075,646, filed Nov. 5, 2014, each of which is incorporated herein by reference in its entirety.

STATEMENT OF GOVERNMENT INTEREST

This invention was made with U.S. Government support under Grant Nos. R01-AI089526-04 and R01-NS065890 awarded by the National Institutes of Health; under a Department of Defens Transformative Vision Award; and under Grant No. GM75061. The U.S. Government has certain rights in the invention.

TECHNICAL FIELD

The present disclosure relates to compounds having affinity to Hsp70i receptors, pharmaceutical compositions containing the compounds, and methods of using the compounds and compositions for treating or preventing diseases and conditions in which Hsp70i is involved.

BACKGROUND

The Heat shock protein 70 (Hsp70) family members have broad chaperone functions in cells that include folding of nascent proteins, refolding of misfolded proteins, removal of protein complexes, and control of regulatory proteins [Daugaard, M., Rohde, M., and Jaattela, M. (2007). The heat shock protein 70 family: Highly homologous proteins with overlapping and distinct functions. FEBS letters 581, 3702-3710; Evans et al. (2010). Heat shock protein 70 (hsp70) as an emerging drug target. Journal of medicinal chemistry 53, 4585-4602]. These functions are driven by ATP hydrolysis in the N-terminal nucleotide-binding domain (NBD) of the Hsp70s. The Hsp70s are evolutionary conserved across species and there are 8 mammalian family members [Hunt, C., and Morimoto, R. I. (1985). Conserved features of eukaryotic hsp70 genes revealed by comparison with the nucleotide sequence of human hsp70. Proceedings of the National Academy of Sciences of the United States of America 82, 6455-6459]. The inducible form of Hsp70 (Hsp70i, also called Hsp72, Hsp70-1, HspA1A/HspA1B) is present in low or undetectable levels in unstressed normal cells, however, expression levels rapidly increase in response to cellular stresses such as heat shock, viral infection or transformation. Deletion of its immediate paralog, the constitutive heat shock protein cognate 70 (Hsc70) is developmentally lethal, whereas deletion of Hsp70i results in sterility of male mice, but no other overt phenotype [Dix et al. (1996). Targeted gene disruption of Hsp70-2 results in failed meiosis, germ cell apoptosis, and male infertility. Proceedings of the National Academy of Sciences of the United States of America 93, 3264-3268; Wacker et al. (2009). Loss of Hsp70 exacerbates pathogenesis but not levels of fibrillar aggregates in a mouse model of Huntington's disease. The Journal of neuroscience: the official journal of the Society for Neuroscience 29, 9104-9114]. Hsp70i and Hsc70 are highly related, sharing 90% sequence identity, with most of the amino acid variability confined to the NBD. There is greater sequence divergence with respect to other Hsp70 family members (50-80% identity), especially within the NBD [Daugaard et al., 2007]. The close sequence similarity between Hsp70i and Hsc70 has contributed to past difficulties in separating the two proteins' functions, both pharmacologically and with RNA interference approaches.

Overexpression of Hsp70i has been observed in several cancers, including breast, prostate, and colon, and this is thought to aid in resistance to apoptosis as well as to anti-cancer treatments [Goloudina et al. (2012). Inhibition of HSP70: a challenging anti-cancer strategy. Cancer letters 325, 117-124; Shu et al. (2008). HSP70s: From Tumor Transformation to Cancer Therapy. Clinical medicine Oncology 2, 335-345]. Hsp70i inhibits both intrinsic and extrinsic apoptosis pathways. This occurs by preventing TNF-related apoptosis-inducing ligand formation of the death-induced signaling complex through inhibition of death receptors 4 and 5, as well as by inhibiting events in mitochondrial-mediated apoptosis [Goloudina et al., 2012; Guo et al. (2005b). Mechanistic role of heat shock protein 70 in Bcr-Abl-mediated resistance to apoptosis in human acute leukemia cells. Blood 105, 1246-1255]. In the latter case, Hsp70i prevents Bax translocation to the mitochondria, preventing release of cytochrome c, an apoptosis inducing factor [Yang et al. (2012). Hsp70 promotes chemoresistance by blocking Bax mitochondrial translocation in ovarian cancer cells. Cancer letters 321, 137-143]. Additionally, Hsp70i mediates both caspase dependent and independent apoptotic pathways by binding Apaf-1, blocking recruitment of procaspase-9 to the apoptosome, and by inhibition of JNK, respectively [Beere et al. (2000). Heat-shock protein 70 inhibits apoptosis by preventing recruitment of procaspase-9 to the Apaf-1 apoptosome. Nature cell biology 2, 469-475; Park et al. (2001). Hsp72 functions as a natural inhibitory protein of c-Jun N-terminal kinase. The EMBO journal 20, 446-456]. Hsp70i also protects cancer cells from oncogenic stress induced by up-regulation of specific oncogenes such as HER2 [Afanasyeva et al. (2007). Drug-induced Myc-mediated apoptosis of cancer cells is inhibited by stress protein Hsp70. International journal of cancer Journal international du cancer 121, 2615-2621]. Increased expression of Hsp70i correlates with resistance to chemotherapy and radiation and therefore poor clinical outcomes by providing cancer cells a route to survive and proliferate in the presence of noxious stimuli such as hypoxia or denatured protein aggregates [Jego et al. (2013). Targeting heat shock proteins in cancer. Cancer letters 332, 275-285]. These data have led to the proposal that cancer cells are dependent on Hsp70i for survival [Goloudina et al., 2012]. This hypothesis is supported by Hsp70i depletion studies in which tumor cell death and sensitivity to chemotherapeutic drugs were evident, while non-tumorigenic cell lines were unaffected by Hsp70i depletion [Nylandsted et al. (2002). Eradication of glioblastoma, and breast and colon carcinoma xenografts by Hsp70 depletion. Cancer research 62, 7139-7142].

From a drug discovery perspective, Hsp70i presents a number of challenges, not least of which being its close sequence identity with Hsc70. Specific, physiological substrates of Hsp70i are poorly defined and high throughput assays based on chaperone or trafficking activities are limited [Kang et al. (2008). Design of a fluorescence polarization assay platform for the study of human Hsp70. Bioorganic & medicinal chemistry letters 18, 3749-3751]. The crystal structure of Hsp70i shows the protein in either a closed nucleotide bound state or open unbound state [Qi et al. (2013). Allosteric opening of the polypeptide-binding site when an Hsp70 binds ATP. Nature structural & molecular biology 20, 900-907]. In the closed conformation, the bound nucleotide shows little solvent accessibility to the surface, limiting access to diffusible small molecule inhibitors. In cells, Hsp70s may be reminiscent of small G proteins in which the nucleotide-binding pocket is always occupied, undergoing GTP/GDP exchange upon activation, again limiting small molecule accessibility. In the case of Hsp70i, the protein has high affinity for ADP, which is likely exchanged with ATP through allosteric regulation [Powers et al. (2010). Targeting HSP70: the second potentially druggable heat shock protein and molecular chaperone? Cell Cycle 9, 1542-1550; Swain et al. (2007). Hsp70 chaperone ligands control domain association via an allosteric mechanism mediated by the interdomain linker. Molecular cell 26, 27-39]. The chaperone activities of Hsp70i are also regulated by the C-terminus in cooperation with co-chaperones, such as Hsp40, Hip, Hop, CHIP and Bag1 [Tavaria et al. (1996). A hitchhiker's guide to the human Hsp70 family. Cell stress & chaperones 1, 23-28]. Crystallographic and NMR studies have shown that these co-chaperones induce altered conformational states [Evans et al., 2010; Mayer et al. (2005). Hsp70 chaperones: cellular functions and molecular mechanism. Cellular and molecular life sciences: CMLS 62, 670-684]. Because of these many complications, most Hsp70 inhibitors have either failed to discriminate between various Hsp70 family members or perform poorly in vivo [Massey, A. J. (2010). ATPases as drug targets: insights from heat shock proteins 70 and 90. Journal of medicinal chemistry 53, 7280-7286].

Prior inhibitors identified to target Hsp70s include NSC 630668-R/1, VER, MAL3-101, MKT-077, PES, Apoptozole, and YK5 [Powers et al., 2010; Rodina et al. (2013). Identification of an allosteric pocket on human hsp70 reveals a mode of inhibition of this therapeutically important protein. Chemistry & biology 20, 1469-1480]. There is considerable structural diversity amongst these inhibitors and generally the NBD domain has been favored for inhibitor development [Powers et al., 2010]. However, the polar interactions present in the nucleotide binding pocket and its affinity for ATP have contributed to difficulties in selective inhibitor discovery [Massey, 2010]. The full-length crystal structure of the nucleotide bound form shows that the nucleotide is completely enclosed, making the accessibility of small inhibitors difficult (FIG. 1B). Approaches adopted thus far have not been able to target specific Hsp70 family members, especially Hsp70i from Hsc70. NSC 630668-R/1, inhibits ATPase activity but does not discriminate Hsp70i from Hsc70 [Fewell et al. (2001). Identification of an inhibitor of hsc70-mediated protein translocation and ATP hydrolysis. The Journal of biological chemistry 276, 910-914]. VER shows broad specificity with other Heat shock protein family members, largely because it is a nucleotide derivative. It also contains two potentially labile, perhaps by design, benzyl groups [Massey, 2010]. MAL3-101 has been shown to compromise co-chaperone-stimulated Hsp70 ATPase activity, suggesting it is an allosteric regulator, although the exact binding site of this molecule remains unknown [Braunstein et al. (2011). Antimyeloma Effects of the Heat Shock Protein 70 Molecular Chaperone Inhibitor MAL3-101. Journal of oncology 2011, 232037]. Like NSC 630668-R/1, MAL3-101 is quite large and has a number of labile ester groups. MKT-077 targets the NBD and inhibits proliferation in tumor cell lines, however, severe renal dysfunction in patients was observed in phase I clinical trials [Britten et al. (2000). A phase I and pharmacokinetic study of the mitochondrial-specific rhodacyanine dye analog MKT 077. Clinical cancer research: an official journal of the American Association for Cancer Research 6, 42-49]. PES has been shown to interact with the SBD of both Hsc70 and Hsp70i and disrupt client protein interaction in vitro [Leu et al. (2009). A small molecule inhibitor of inducible heat shock protein 70. Molecular cell 36, 15-27]. However, recent evidence suggests that the PES interaction with Hsp70 is through non-specific interactions [Schlecht et al. (2013). Functional analysis of Hsp70 inhibitors. PloS one 8, e78443]. The molecule promotes caspase-dependent cell death only in tumor cells, suggesting some specificity to Hsp70i in vitro, although p53 binding has also been shown, which may explain its antitumor actions [Leu et al., 2009]. Moreover, MKT-077 and PES have potential reactive groups that render them covalent modifiers, which may contribute to side effects in vivo. YK5 is an allosteric inhibitor of Hsp70, recently identified using modeling techniques, but this molecule does not discriminate between Hsp70i and Hsc70 [Rodina et al., 2013].

Accordingly, there exists a need for receptor ligands selective for Hsp70i.

DETAILED DESCRIPTION

Figure 1:
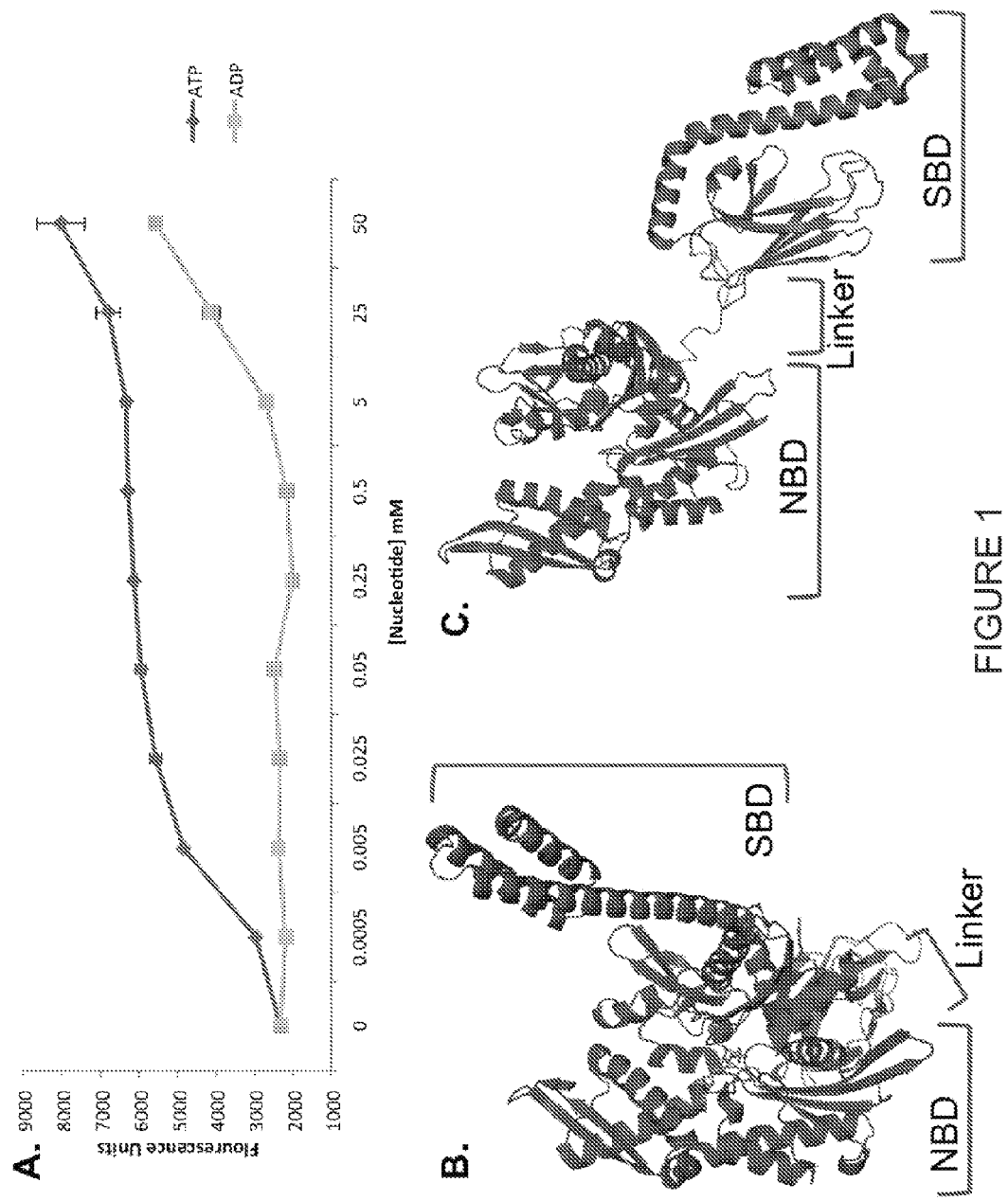
FIG. 1 shows that recombinant GFP-Hsp70i is readily captured on γ-phosphate linked ATP resin and is competitively released with ATP/ADP, consistent with nucleotide induced conformational changes. (A) GFP-Hsp70i was bound to γ-phosphate-linked ATP-Sepharose then eluted with the indicted [ATP] or [ADP]. The solution structures shown in (B and C) suggest a mode of binding in which the GFP-fusion protein first recognizes the immobilized nucleotide in its open apo state. The protein closes around the immobilized ATP but cannot hydrolyze the γ phosphate. The presence of free Mg2+ATP, in contrast to ADP, however, enables rapid turnover and release of the bound protein. (B) Structure of Hsp70 (E. coli, DnaK) in the ATP-bound conformation (PDB 4B9Q) and (C) in the ADP-bound apo conformation (PDB 2KHO). NBD highlighted in blue, linker domain highlighted in green, and SBD highlighted in red. ATP represented in (B) as ball-and-stick model.

Disclosed are Hsp70i receptor ligands. The Hsp70 inhibitors can exhibit selectivity for Hsp70i over Hsc70 and other family members. ((S)—N-(1-propyl-1H-benzo[d]imidazol-2-yl)-1-(pyrazin-2-yl)piperidine-3-carboxamide) ("HS-72"), a selective allosteric inhibitor of Hsp70i, bears all the hallmarks of an Hsp70 inhibitor in cell models of breast cancer and in a cell culture model of Huntington's disease. The molecule is well tolerated and is bioavailable in mice, and shows efficacy in the MMTV-neu mouse model of breast cancer.

Various biochemical approaches demonstrated the selectivity of HS-72 towards Hsp70i over other Hsp70 family members, in particular Hsc70. This includes selective elution from γ-phosphate linked ATP resin, creation of a highly selective HS-72 affinity resin, a selective thermo destabilizing effect in the presence of ATP compared with Hsc70 and Hsp90, altered protease digestion patterns in the presence and absence of the inhibitor, and sensitivity to the S enantiomer over the R form HS-71.

The present disclosure demonstrates that HS-72 can act in vitro as an allosteric inhibitor of ATP binding, a feature believed to underlie its ability to discriminate Hsp70i from other Hsp70 family members. This mode of action may also explain HS-72 selectivity against the broader purinome, since the molecule is not directly targeting the ATP binding pocket, suggested by molecular docking studies.

In cells, HS-72 bears all the hallmarks associated with inhibition of Hsp70i. At the molecular level this includes loss of HER2 and AKT expression in breast tumor cells and formation of protein aggregates in a cellular based model of Huntington's disease. The inhibitor is also synergistic in combination with Hsp90 inhibitors, as determined by monitoring HER2 and AKT expression. In proliferation assays, HS-72 shows specificity towards more aggressive breast and prostate tumor cell lines, consistent with the specific role of Hsp70i in mediating metastatic progression in vivo [Juhasz et al. (2013). The complex function of hsp70 in metastatic cancer. Cancers 6, 42-66]. HS-72 is well tolerated and bioavailable in mice with no evidence of overt toxicity at high doses. Efficacy of HS-72 was evaluated in the MMTV model, a murine model of spontaneous breast cancer in humans [Taneja et al. (2009). MMTV mouse models and the diagnostic values of MMTV-like sequences in human breast cancer. Expert review of molecular diagnostics 9, 423-440]. On a conservative biweekly administration cycle, HS-72 demonstrated significant inhibition of tumor growth with evidence of improved survival. Further, a PK study showed that plasma [HS-72] are maintained at >20 μM for at least 8 hours, levels that reflect its potency against various tumor cell lines in vitro. An HS-72 affinity resin was synthesized and analogs can readily be prepared according to the present disclosure.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "about" is used synonymously with the term "approximately." Illustratively, the use of the term "about" indicates that values slightly outside the cited values, namely, plus or minus 10%. Such values are thus encompassed by the scope of the claims reciting the terms "about" and "approximately."

The terms "administer", "administering", "administered" or "administration" refer to any manner of providing a compound or a pharmaceutical composition (e.g., one described herein), to a subject or patient. Routes of administration can be accomplished through any means known by those skilled in the art. Such means include, but are not limited to, oral, buccal, intravenous, subcutaneous, intramuscular, transdermal, by inhalation and the like.

"Contacting" as used herein, e.g., as in "contacting a sample" refers to contacting a sample directly or indirectly in vitro, ex vivo, or in vivo (i.e. within a subject as defined herein). Contacting a sample may include addition of a compound to a sample (e.g., a sample comprising cells that contain Hsp70), or administration to a subject. Contacting encompasses administration to a solution, cell, tissue, mammal, subject, patient, or human. Further, contacting a cell includes adding an agent to a cell culture.

"Detection moiety" as used herein includes one or more groups that are detectable, either directly or indirectly, by methods such as spectroscopic, photochemical, biochemical, chemical, or other methods. For example, useful detectable moieties or labels include chromophores, fluorophores, biotin, radioactive compounds, and the like. The detection moiety often generates a measurable signal, such as a radioactive, chromogenic, luminescent, or fluorescent signal, which can be used to quantitate the amount of the detection moiety in a sample. In some embodiments a detection moiety may include more than one detectable group, e.g., a fluorophore and a radioactive moiety.

"Effective amount," as used herein, refers to a dosage or an amount of a compound or a composition effective for eliciting a desired effect. This term as used herein may also refer to an amount effective at bringing about a desired in vivo effect in an animal, e.g., a mammal, e.g., a human. For example, in methods of treating cancer, an effective amount may be an amount sufficient to treat the disorder.

As used herein, the term "subject" is intended to include human and non-human animals. Exemplary human subjects include a human patient having a disorder, e.g., cancer, or a normal subject. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.).

As used herein, the term "treat" or "treating" a subject having a disorder refers to administering a compound or a composition described herein to the subject, such that at least one symptom of the disorder is cured, healed, alleviated, relieved, altered, remedied, ameliorated, or improved. Treating includes administering an amount effective to alleviate, relieve, alter, remedy, ameliorate, cure, improve or affect the disorder or the symptoms of the disorder. The treatment may inhibit deterioration or worsening of a symptom of a disorder.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "acyl" refers to an alkylcarbonyl, cycloalkylcarbonyl, heterocyclylcarbonyl, arylcarbonyl or heteroarylcarbonyl substituent, any of which may be further substituted (e.g., with one or more substituents).

The term "alkyl" refers to a saturated aliphatic hydrocarbon chain, which may be straight or branched. An alkyl group may have an indicated number of carbon atoms. For example, $C_1$-$C_{12}$ alkyl refers to an alkyl group having from 1 to 12 (inclusive) carbon atoms. $C_1$-$C_4$ alkyl refers to an alkyl group having 1, 2, 3 or 4 carbon atoms, such as methyl, ethyl, n-propyl, isopropyl, n-butyl, sec-butyl or tert-butyl. An alkyl group may be optionally substituted, e.g., with one or more substituents.

The term "alkylene" refers to a divalent alkyl, e.g., —$CH_2$—, —$CH_2CH_2$—, —$CH_2CH_2CH_2$— or —$CH_2CH(CH_3)CH_2$—. An alkylene may be optionally substituted, e.g., with one or more substituents.

The term "alkenyl" refers to a straight or branched hydrocarbon chain having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkenylene" refers to a divalent alkenyl, e.g., —CH═CH—, —CH═$CH_2CH_2$— or —CH═C═CH—. An alkenyl or alkenylene may be optionally substituted, e.g., with one or more substituents.

The term "alkynyl" refers to a straight or branched hydrocarbon chain having one or more triple bonds. Examples of alkynyl groups include, but are not limited to, ethynyl, propargyl, and 3-hexynyl. One of the triple bond carbons may optionally be the point of attachment of the alkynyl substituent. The term "alkynylene" refers to a divalent alkynyl, e.g., —C≡C— or —C≡C—$CH_2$—. An alkynyl or alkynylene may be optionally substituted, e.g., with one or more substituents.

The term "amino" refers to a group of the formula —$NR^1R^2$, wherein $R^1$ and $R^2$ are each independently selected from, for example, hydrogen, alkyl, cycloalkyl, heterocyclyl, aryl and heteroaryl, or $R^1$ and $R^2$, together with the nitrogen to which they are attached, may form a ring structure. Examples of amino groups include, but are not limited to, —$NH_2$, alkylamino groups such as —$NHCH_3$, —$NHCH_2CH_3$ and —$NHCH(CH_3)_2$, dialkylamino groups such as —$N(CH_3)_2$ and —$N(CH_2CH_3)_2$, and arylamino groups such as —NHPh. Examples of cyclic amino groups include, but are not limited to, aziridinyl, azetidinyl, pyrrolidinyl, piperidino, piperazinyl, perhydrodiazepinyl, morpholino, and thiomorpholino. The groups $R^1$ and $R^2$ may be optionally substituted, e.g., with one or more substituents.

The term "aryl" refers to an aromatic monocyclic, bicyclic, or tricyclic hydrocarbon ring system, wherein any ring atom capable of substitution can be substituted (e.g., with one or more substituents). Examples of aryl moieties include, but are not limited to, phenyl, naphthyl, and anthracenyl.

The term "arylalkyl" refers to an alkyl moiety in which an alkyl hydrogen atom is replaced with an aryl group. Arylalkyl includes groups in which more than one hydrogen atom has been replaced with an aryl group. Examples of arylalkyl groups include benzyl, 2-phenylethyl, 3-phenylpropyl, 9-fluorenyl, benzhydryl, and trityl groups.

The term "cycloalkyl" as used herein refers to nonaromatic, saturated or partially unsaturated cyclic, bicyclic, tricyclic or polycyclic hydrocarbon groups having 3 to 12 carbons. Any ring atom can be substituted (e.g., with one or more substituents). Cycloalkyl groups can contain fused rings. Fused rings are rings that share one or more common carbon atoms. Examples of cycloalkyl groups include, but are not limited to, cyclopropyl, cyclobutyl, cyclopentyl, cyclohexyl, cyclohexenyl, cyclohexadienyl, methylcyclohexyl, adamantyl, norbornyl and norbornenyl.

The term "cycloalkylalkyl", as used herein, refers to an alkyl group substituted with a cycloalkyl group.

The term "halo" or "halogen" as used herein refers to any radical of fluorine, chlorine, bromine or iodine.

The term "haloalkyl" as used herein refers to an alkyl in which one or more hydrogen atoms are replaced with a halogen, and includes alkyl moieties in which all hydrogens have been replaced with halogens (e.g., perfluoroalkyl such as $CF_3$).

The term "heteroalkyl" refers to an alkyl, alkenyl or alkynyl group as defined herein, wherein at least one carbon atom of the alkyl group is replaced with a heteroatom. Heteroalkyl groups may contain from 1 to 18 non-hydrogen atoms (carbon and heteroatoms) in the chain, or 1 to 12 atoms, or 1 to 6 atoms, or 1 to 4 atoms. Heteroalkyl groups may be straight or branched, and saturated or unsaturated. Unsaturated heteroalkyl groups have one or more double bonds and/or one or more triple bonds. Heteroalkyl groups may be unsubstituted or substituted. Exemplary heteroalkyl groups include but are not limited to alkoxyalkyl (e.g., methoxymethyl), and aminoalkyl (e.g., alkylaminoalkyl and dialkylaminoalkyl). Heteroalkyl groups may be optionally substituted with one or more substituents.

The term "heteralkylenyl" refers to a divalent heteroalkyl group, examples of which include but are not limited to —$CH_2OCH_2$—, —$CH_2NHCH_2$—, polyethyleneglycol groups (e.g., —$(CH_2CH_2O)_n$—), polyethyleneimine groups (e.g., —$(CH_2CH_2NH)_n$—), and the like. A heteroalkylenyl group may be optionally substituted with one or more substituents.

The term "heteroaryl" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P and Si (e.g., carbon atoms and 1-3, 1-6, or 1-9 heteroatoms independently selected from O, N, S, P and Si if monocyclic, bicyclic, or tricyclic, respectively). Any ring atom can be substituted (e.g., with one or more substituents). Heteroaryl groups can contain fused rings, which are rings that share one or more common atoms. Examples of heteroaryl groups include, but are not limited to, radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines and purines.

The term "heteroarylalkyl" refers to an alkyl moiety in which at least one alkyl hydrogen atom is replaced with a heteroaryl group. Heteroarylalkyl includes groups in which more than one hydrogen atom has been replaced with a heteroaryl group. Examples of heteroarylalkyl groups include but are not limited to imidazolylmethyl (e.g., 1H-imidazol-2-ylmethyl and 1H-imidazol-4-ylmethyl), pyridinylmethyl (e.g., pyridin-3-ylmethyl and pyridin-4-ylmethyl), pyrimidinylmethyl (e.g., pyrimidin-5-ylmethyl), furylmethyl (e.g., fur-2-ylmethyl and fur-3-ylmethyl), and thienylmethyl (e.g., thien-2-ylmethyl and thien-3-ylmethyl) groups. Heteroarylalkyl groups may be optionally substituted with one or more substituents, on either the heteroaryl moiety or the alkyl moiety.

The term "heteroatom" as used herein, refers to a non-carbon or hydrogen atom such as a nitrogen, sulfur, oxygen, silicon or phosphorus atom. Groups containing more than one heteroatom may contain different heteroatoms.

The term "heterocyclyl" as used herein refers to a non-aromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocyclyl groups can contain fused rings, which are rings that share one or more common atoms. Examples of heterocyclyl groups include, but are not limited to, radicals of tetrahydrofuran, tetrahydrothiophene, tetrahydropyran, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like.

The term "heterocyclylalkyl", as used herein, refers to an alkyl group substituted with a heterocyclyl group.

The term "hydroxy" refers to an —OH radical. The term "alkoxy" refers to an —O-alkyl radical. The term "aryloxy" refers to an —O-aryl radical.

The term "oxo" refers to an oxygen atom, which forms a carbonyl when attached to carbon, an N-oxide when attached to nitrogen, and a sulfoxide or sulfone when attached to sulfur.

The term "mercapto" or "thiol" refers to an —SH radical. The term "thioalkoxy" or "thioether" refers to an —S-alkyl radical. The term "thioaryloxy" refers to an —S-aryl radical.

The term "substituents" refers to a group "substituted" on an alkyl, alkenyl, alkynyl, cycloalkyl, cycloalkylalkyl, heterocyclyl, heterocyclylalkyl, aryl, arylalkyl, heteroaryl or heteroarylalkyl group at any atom of that group. Any atom can be substituted. Suitable substituents include, without limitation: acyl, acylamido, acyloxy, alkoxy, alkyl, alkenyl, alkynyl, amido, amino, carboxy, cyano, ester, halo, hydroxy, imino, nitro, oxo (e.g., C=O), phosphonate, sulfinyl, sulfonyl, sulfonate, sulfonamino, sulfonamido, thioamido, thiol, thioxo (e.g., C=S), and ureido. In embodiments, substituents on a group are independently any one single, or any combination of the aforementioned substituents. In embodiments, a substituent may itself be substituted with any one of the above substituents.

Any of the above substituents may be abbreviated herein, for example, the abbreviations Me, Et and Ph represent methyl, ethyl and phenyl, respectively. A more comprehensive list of the abbreviations used by organic chemists of ordinary skill in the art appears in the first issue of each volume of the Journal of Organic Chemistry; this list is typically presented in a table entitled Standard List of Abbreviations. The abbreviations contained in said list, and all abbreviations used by organic chemists of ordinary skill in the art, are hereby incorporated by reference.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH$_2$O— optionally also recites —OCH$_2$—.

In accordance with a convention used in the art, the group:

is used in structural formulas herein to depict the bond that is the point of attachment of the moiety or substituent to the core or backbone structure.

It specifically is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

2. Compounds

In one aspect, disclosed is a compound of formula (I), or a pharmaceutically acceptable salt thereof,

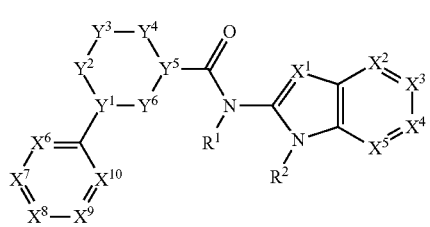

wherein
$X^1$, $X^2$, $X^3$, $X^4$, $X^5$, $X^6$, $X^7$, $X^8$, $X^9$, and $X^{10}$ are each independently selected from the group consisting of N and $C(R^3)$;
$Y^1$ and $Y^5$ are each independently selected from the group consisting of N and $C(R^4)$;
$Y^2$, $Y^3$, $Y^4$, and $Y^6$ are each independently selected from the group consisting of a bond, O, S, $N(R^5)$, and $C(R^6R^7)$, provided no more than one of $Y^2$, $Y^3$, $Y^4$, and $Y^6$ is a bond, and provided that at least two of $Y^2$, $Y^3$, $Y^4$, and $Y^6$ are $C(R^4)$;
$R^1$ is hydrogen, alkyl, haloalkyl, hydroxyalkyl, alkoxyalkyl, haloalkoxyalkyl, aminoalkyl, alkylaminoalkyl, di(alkyl)aminoalkyl, or cyanoalkyl;
$R^2$ is alkyl, haloalkyl, hydroxyalkyl, alkoxyalkyl, haloalkoxyalkyl, aminoalkyl, alkylaminoalkyl, di(alkyl)aminoalkyl, or cyanoalkyl; and
$R^3$, $R^4$, $R^5$, $R^6$, and $R^7$, at each occurrence, are each independently selected from the group consisting of hydrogen, halogen, alkyl, haloalkyl, hydroxyalkyl, alkoxyalkyl, haloalkoxyalkyl, aminoalkyl, alkylaminoalkyl, di(alkyl)aminoalkyl, cyanoalkyl, alkoxy, haloalkoxy, cyano, hydroxy, amino, alkylamino, and di(alkyl)amino.

In certain embodiments, $X^1$ is N.
In certain embodiments, $X^2$, $X^3$, $X^4$, and $X^5$ are each $C(R^3)$.
In certain embodiments, $X^2$ is CH; $X^3$ is CH; $X^4$ is CH; and $X^5$ is CH.
In certain embodiments, $X^6$ is N; $X^7$ is $C(R^3)$; $X^8$ is $C(R^3)$; $X^9$ is N; and $X^{10}$ is $C(R^3)$.
In certain embodiments, $X^6$ is N; $X^7$ is CH; $X^8$ is CH; $X^9$ is N; and $X^{10}$ is CH.
In certain embodiments, $Y^1$ is N; $Y^2$ is $C(R^6R^7)$; $Y^3$ is $C(R^6R^7)$; $Y^4$ is $C(R^6R^7)$; $Y^5$ is $C(R^4)$; and $Y^6$ is $C(R^6R^7)$.
In certain embodiments, $Y^1$ is N; $Y^2$ is $CH_2$; $Y^3$ is $CH_2$; $Y^4$ is $CH_2$; $Y^5$ is CH; and $Y^6$ is $CH_2$.
In certain embodiments, $R^1$ is hydrogen.
In certain embodiments, $R^2$ is $C_1$-$C_{10}$-alkyl.
In certain embodiments, the compound of formula (I) has formula (I-a),

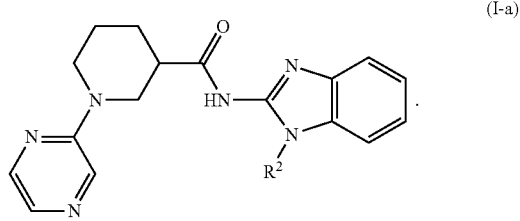

In certain embodiments, $R^2$ is $C_1$-$C_{10}$-alkyl in compounds of formula (I-a).

In certain embodiments, the compound of formula (I) has formula (I-b),

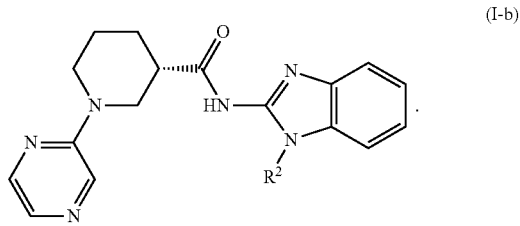

In certain embodiments, $R^2$ is $C_1$-$C_{10}$-alkyl in compounds of formula (I-b).

In certain embodiments, the compound of formula (I) has formula (I-c),

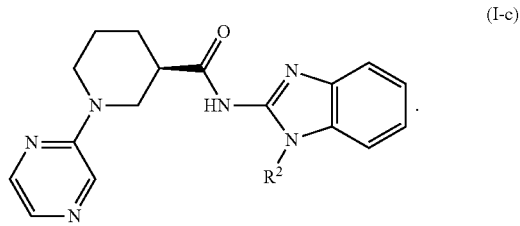

In certain embodiments, $R^2$ is $C_1$-$C_{10}$-alkyl in compounds of formula (I-c).

In certain embodiments, the compound of formula (I) has formula (I-d),

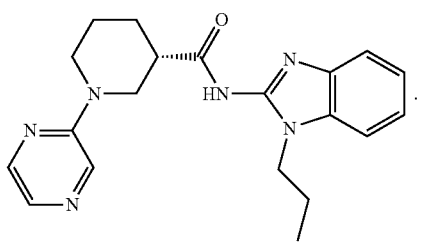

(I-d)

Certain compounds may exist in one or more particular geometric, optical, enantiomeric, diastereomeric, epimeric, atropic, stereoisomer, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; a- and β-forms; axial and equatorial forms; boat-, chair-, twist-, envelope-, and half chair-forms; and combinations thereof, hereinafter collectively referred to as "isomers" (or "isomeric forms").

In one embodiment, a compound described herein may be an enantiomerically enriched isomer of a stereoisomer described herein. For example, the compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%. Enantiomer, when used herein, refers to either of a pair of chemical compounds whose molecular structures have a mirror-image relationship to each other.

In one embodiment, a preparation of a compound disclosed herein is enriched for an isomer of the compound having a selected stereochemistry, e.g., R or S, corresponding to a selected stereocenter. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

In one embodiment, a composition described herein includes a preparation of a compound disclosed herein that is enriched for a structure or structures having a selected stereochemistry, e.g., R or S, at a selected stereocenter. Exemplary R/S configurations can be those provided in an example described herein.

An "enriched preparation," as used herein, is enriched for a selected stereoconfiguration of one, two, three or more selected stereocenters within the subject compound. Exemplary selected stereocenters and exemplary stereoconfigurations thereof can be selected from those provided herein, e.g., in an example described herein. By enriched is meant at least 60%, e.g., of the molecules of compound in the preparation have a selected stereochemistry of a selected stereocenter. In an embodiment it is at least 65%, 70%, 75%, 80%, 85%, 90%, 95%, 96%, 97%, 98%, or 99%. Enriched refers to the level of a subject molecule(s) and does not connote a process limitation unless specified.

Compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

Except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_3$-alkyl or propyl includes n-propyl and iso-propyl; $C_4$-alkyl or butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hydroxyazo, and nitro/aci-nitro.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

A compound described herein can be in the form of a salt, e.g., a pharmaceutically acceptable salt. The term "pharmaceutically acceptable salt" includes salts of the active compounds that are prepared with relatively nontoxic acids or bases, depending on the particular substituents found on the compounds described herein. Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure. Examples of pharmaceutically acceptable salts are discussed in Berge et al, 1977, "Pharmaceutically Acceptable Salts." J. Pharm. Sci. Vol. 66, pp. 1-19.

For example, if the compound is anionic, or has a functional group which may be anionic (e.g., —COOH may be —$COO^-$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations. Examples of suitable organic cations include, but are not limited to, ammonium ion (i.e., $NH_4^+$) and substituted ammonium ions (e.g., $NH_3R_1^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine.

If the compound is cationic, or has a functional group that may be cationic (e.g., —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, gluchep tonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

It may be convenient or desirable to prepare, purify, and/or handle an active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999). Unless otherwise specified, a reference to a particular compound also includes chemically protected forms thereof.

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

A hydroxy group may be protected as an ether (—OR) or an ester (—OC(O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(O)CH₃, —OAc).

An aldehyde or ketone group may be protected as an acetal (RCH(OR)₂) or ketal (R₂C(OR)₂), respectively, in which the carbonyl group (R₂C=O) is converted to a diether (R₂C(OR)₂), by reaction with, for example, a primary alcohol. The aldehyde or ketone group is readily regenerated by hydrolysis using a large excess of water in the presence of acid.

An amine group may be protected, for example, as an amide (—NRC(O)R) or a urethane (—NRC(O)OR), for example, as: a methyl amide (—NHC(O)CH₃); a benzyloxy amide (—NHC(O)OCH₂C₆H₅, —NH-Cbz); as a t-butoxy amide (—NHC(O)OC(CH₃)₃, —NH-Boc); a 2-biphenyl-2-propoxy amide (—NHCO(O)C(CH₃)₂C₆H₄C₆H₅, —NH-Bpoc), as a 9-fluorenylmethoxy amide (—NH-Fmoc), as a 6-nitroveratryloxy amide (—NH—Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N–0<<).

A carboxylic acid group may be protected as an ester, for example, as: an alkyl ester (e.g., a methyl ester; a t-butyl ester); a haloalkyl ester (e.g., a haloalkyl ester); a trialkylsilylalkyl ester; or an arylalkyl ester (e.g., a benzyl ester; a nitrobenzyl ester); or as an amide, for example, as a methyl amide.

A thiol group may be protected as a thioether (—SR), for example, as: a benzyl thioether; an acetamidomethyl ether (—S—CH₂NHC(O)CH₃)

In addition to salt forms, the present disclosure may also provide compounds that are in a prodrug form. Prodrugs of the compounds described herein are those compounds that readily undergo chemical changes under physiological conditions to provide the compounds described herein. Prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

A compound described herein can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom substitution in aromatic rings.

3. Synthetic Methods

The compounds of the present disclosure can be better understood in connection with the following synthetic schemes and methods which illustrate a means by which the compounds can be prepared.

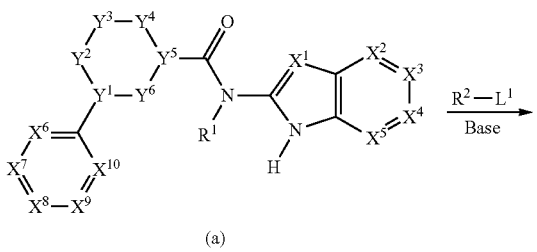

(a)

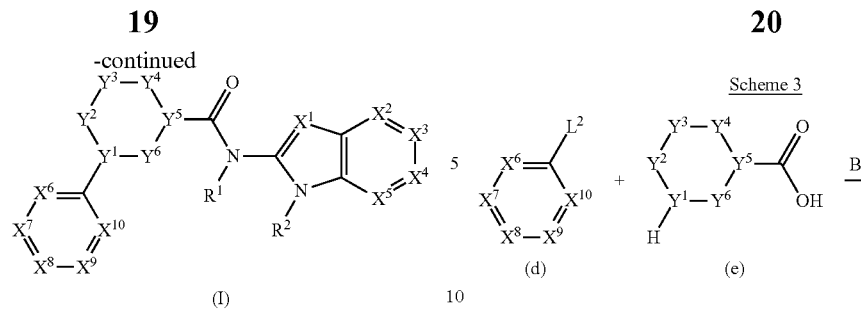

Compounds of formula (I) can be prepared as shown in Scheme 1, wherein $X^1$, $X^2$, $X^3$, $X^4$, $X^5$, $X^6$, $X^7$, $X^8$, $X^9$, $X^{10}$, $Y^1$, $Y^2$, $Y^3$, $Y^4$, $Y^5$, $Y^6$, $R^1$, $R^2$, $R^3$, $R^4$, $R^5$, $R^6$, and $R^7$ are as defined above. A compound of formula (a) can be alkylated with an alkylating agent $R^2$-$L^1$ to provide a compound of formula (I), wherein $R^2$ is alkyl, haloalkyl, hydroxyalkyl, alkoxyalkyl, haloalkoxyalkyl, aminoalkyl, alkylaminoalkyl, di(alkyl)aminoalkyl, or cyanoalkyl, and $L^1$ is a leaving group (e.g., halo such as bromo or chloro, or sulfonate ester such as tosylate or mesylate). The group defined by $R^2$ in $R^2$-$L^1$ can be protected as necessary to affect alkylation, and the protecting group can be removed thereafter.

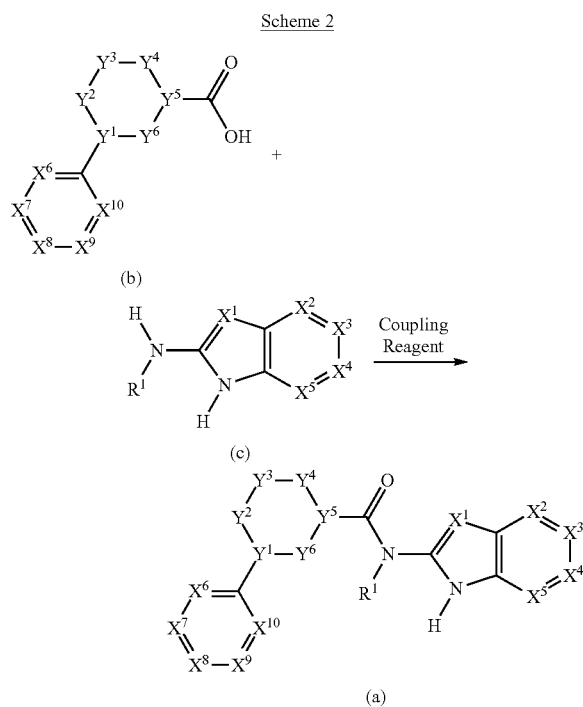

Compounds of formula (a) can be prepared as shown in Scheme 2. A compound of formula (b) can be coupled with a compound of formula (c) to provide a compound of formula (a). The coupling agent may be, for example, 1-ethyl-3-(3-dimethylaminopropyl)carbodiimide (EDCI), 1-[bis(dimethylamino)methylene]-1H-1,2,3-triazolo[4,5-b]pyridinium 3-oxid hexafluorophosphate (HATU), or hydroxybenzotriazole (HOBt). Bases (e.g., Hunig's base) and catalysts (e.g., 4-dimethylaminopyridine (DMAP)) can be used as necessary. In certain embodiments, $R^1$ is preferably hydrogen in formula (c) in order to facilitate smooth coupling between the carboxylic acid and the amine functional groups.

Compounds of formula (b) can be prepared as shown in Scheme 3. A compound of formula (d) can undergo nucleophilic aromatic substitution with a compound of formula (e), provided that $Y^1$ is nucleophilic and $L^2$ is a suitable leaving group (e.g., halo such as chloro or bromo). The substitution can be performed in the presence of a base (e.g., Hunig's base).

In certain embodiments, the products may be further modified, for example, by manipulation of substituents. These manipulations may include, but are not limited to, reduction, oxidation, organometallic cross-coupling, alkylation, acylation, and hydrolysis reactions which are commonly known to those skilled in the art. In some cases, the order of carrying out the foregoing reaction schemes may be varied to facilitate the reaction or to avoid unwanted reaction products.

4. Pharmaceutical Compositions

Also disclosed herein are pharmaceutical compositions comprising a compound of formula (I) and a pharmaceutically acceptable carrier. In certain embodiments, disclosed is a pharmaceutical composition comprising ((S)—N-(1-propyl-1H-benzo[d]imidazol-2-yl)-1-(pyrazin-2-yl)piperidine-3-carboxamide) ("HS-72") and a pharmaceutically acceptable carrier.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions can be administered to subjects (e.g., humans and other mammals) orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Dosage forms for topical or transdermal administration of a compound include ointments, pastes, creams, lotions, gels, powders, solutions, sprays, inhalants or patches. A desired compound is admixed under sterile conditions with a pharmaceutically acceptable carrier and any needed preservatives or buffers as may be required. Ophthalmic formulation, eardrops, eye ointments, powders and solutions are also contemplated as being within the scope of this disclosure.

The ointments, pastes, creams and gels may contain, in addition to an active compound, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds, lactose, talc, silicic acid, aluminum hydroxide, calcium silicates and polyamide powder, or mixtures of these substances. Sprays can additionally contain customary propellants such as chlorofluorohydrocarbons.

Compounds also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds, stabilizers, preservatives, and the like. The preferred lipids are the natural and synthetic phospholipids and phosphatidylcholines (lecithins) used separately or together. Methods to form liposomes are known in the art. See, for example, Prescott, Ed., Methods in Cell Biology, Volume XIV, Academic Press, New York, N.Y., (1976), p 33 et seq.

Dosage forms for topical administration of a compound described herein include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this disclosure. Aqueous liquid compositions may also be useful.

5. Methods of Treatment

Also disclosed are methods of using the disclosed compounds and compositions to treat or prevent disorders associated with heat shock protein 70 ("Hsp70") activity.

In one aspect, disclosed is a method of the inhibiting the inducible form of heat shock protein 70 ("HSP70i"), comprising administering to a subject in need thereof a therapeutically effective amount of a compound of formula (I), or a pharmaceutically acceptable salt thereof.

In another aspect, disclosed is a method of inhibiting tumor growth, comprising administering to a subject in need thereof a therapeutically effective amount of a compound of formula (I), or a pharmaceutically acceptable salt thereof.

In another aspect, disclosed is a method of treating or preventing cancer comprising administering to a subject in need thereof a therapeutically effective amount of a compound of formula (I), or a pharmaceutically acceptable salt thereof. The compounds and compositions described herein can be used to treat a subject having any type of cancer, for example those described by the National Cancer Institute. The cancer can be a carcinoma, a sarcoma, a myeloma, a leukemia, a lymphoma or a mixed type. Exemplary cancers described by the National Cancer Institute include but are not limited to: digestive/gastrointestinal cancers such as anal cancer; bile duct cancer; extrahepatic bile duct cancer; appendix cancer; carcinoid tumor, gastrointestinal cancer; colon cancer; colorectal cancer including childhood colorectal cancer; esophageal cancer including childhood esophageal cancer; gallbladder cancer; gastric (stomach) cancer including childhood gastric (stomach) cancer; hepatocellular (liver) cancer including adult (primary) hepatocellular (liver) cancer and childhood (primary) hepatocellular (liver) cancer; pancreatic cancer including childhood pancreatic cancer; sarcoma, rhabdomyosarcoma; islet cell pancreatic cancer; rectal cancer; and small intestine cancer; endocrine cancers such as islet cell carcinoma (endocrine pancreas); adrenocortical carcinoma including childhood adrenocortical carcinoma; gastrointestinal carcinoid tumor; parathyroid cancer; pheochromocytoma; pituitary tumor; thyroid cancer including childhood thyroid cancer; childhood multiple endocrine neoplasia syndrome; and childhood carcinoid tumor; eye cancers such as intraocular melanoma; and retinoblastoma; musculoskeletal cancers such as Ewing's family of tumors; osteosarcoma/malignant fibrous histiocytoma of the bone; childhood rhabdomyosarcoma; soft tissue sarcoma including adult and childhood soft tissue sarcoma; clear cell sarcoma of tendon sheaths; and uterine sarcoma; breast cancer such as breast cancer including childhood and male breast cancer and breast cancer in pregnancy; neurologic cancers such as childhood brain stemglioma; brain tumor; childhood cerebellar astrocytoma; childhood cerebral astrocytoma/malignant glioma; childhood ependymoma; childhood medulloblastoma; childhood pineal and supratentorial primitive neuroectodermal tumors; childhood visual pathway and hypothalamic glioma; other childhood brain cancers; adrenocortical carcinoma; central nervous system lymphoma, primary; childhood cerebellar astrocytoma; neuroblastoma; craniopharyngioma; spinal cord tumors; central nervous system atypical teratoid/rhabdoid tumor; central nervous system embryonal tumors; and childhood supratentorial primitive neuroectodermal tumors and pituitary tumor; genitourinary cancers such as bladder cancer including childhood bladder cancer; renal cell (kidney) cancer; ovarian cancer including childhood ovarian cancer; ovarian epithelial cancer; ovarian low malignant potential tumor; penile cancer; prostate cancer; renal cell cancer including childhood renal cell cancer; renal pelvis and ureter, transitional cell cancer; testicular cancer; urethral cancer; vaginal cancer; vulvar cancer; cervical cancer; Wilms tumor and other childhood kidney tumors; endometrial cancer; and gestational trophoblastic tumor; Germ cell cancers such as childhood extracranial germ cell tumor; extragonadal germ cell tumor; ovarian germ cell tumor; head and neck cancers such as lip and oral cavity cancer; oral cancer including childhood oral cancer (e.g., oral squamous cell carcinoma); hypopharyngeal cancer; laryngeal cancer including childhood laryngeal cancer; metastatic squamous neck cancer with occult primary; mouth cancer; nasal cavity and paranasal sinus cancer; nasopharyngeal cancer including childhood nasopharyngeal cancer; oropharyngeal cancer; parathyroid cancer; pharyngeal cancer; salivary gland cancer including childhood salivary gland cancer; throat cancer; and thyroid cancer; Hematologic/blood cell cancers such as a leukemia (e.g., acute lymphoblastic leukemia including adult and childhood acute lymphoblastic leukemia; acute myeloid leukemia including adult and childhood acute myeloid leukemia; chronic lymphocytic leukemia such as B Cell chronic lymphocytic leukemia; chronic myelogenous leukemia; and hairy cell leukemia); a lymphoma (e.g., AIDS-related lymphoma; cutaneous T-cell lymphoma; Hodgkin's lymphoma including adult and childhood Hodgkin's lymphoma and Hodgkin's lymphoma during pregnancy; non-Hodgkin's lymphoma including adult and childhood non-Hodgkin's lymphoma and non-Hodgkin's lymphoma during pregnancy; mycosis fungoides; Sezary syndrome; Waldenstrom's macroglobulinemia; primary mediastinal large B cell lymphoma; mantle cell lymphoma; diffuse large B cell lymphoma; and primary central nervous system lymphoma); and other hematologic cancers (e.g., chronic myeloproliferative disorders; multiple myeloma/plasma cell neoplasm; myelodysplastic syndromes; and myelodysplastic/myeloproliferative disorders); lung cancer such as non-small cell lung cancer; and small cell lung cancer; respiratory cancers such as adult malignant mesothelioma; childhood malignant mesothelioma; malignant thymoma; childhood thymoma; thymic carcinoma; bronchial adenomas/carcinoids including childhood bronchial adenomas/carcinoids; pleuropulmonary blastoma; non-small cell lung cancer; and small cell lung cancer; skin cancers such as Kaposi's sarcoma; Merkel cell carcinoma; melanoma; and childhood skin cancer; AIDS-related malignancies; other childhood cancers, unusual cancers of childhood and cancers of unknown primary site; and metastases of the aforementioned cancers can also be treated or prevented in accordance with the methods described herein.

In another aspect, disclosed is a method of treating or preventing breast cancer, prostate cancer, colon cancer, or a combination thereof, comprising administering to a subject in need thereof a therapeutically effective amount of a compound of formula (I), or a pharmaceutically acceptable salt thereof.

In another aspect, disclosed is a method of treating or preventing breast cancer, prostate cancer, non-small cell lung cancer, colorectal cancer, pancreatic cancer, ovarian cancer, melanoma, or a combination thereof, comprising administering to a subject in need thereof a therapeutically effective amount of a compound of formula (I), or a pharmaceutically acceptable salt thereof.

Dosage levels of the disclosed compounds can range from about 0.001 mg to about 5,000 mg per kilogram body weight. An effective amount of the active agent may range from about 0.001 mg to about 100 mg per kilogram of patient body weight per day. Dosage of active agent can be administered in a single unit or in multiple dosage units to provide the desired therapeutic effect. It will be appreciated that appropriate dosages of the compounds, and compositions comprising the compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician. In general, a suitable dose of the compound may be in the range of about 100 µg to about 250 mg per kilogram body weight of the subject per day.

The composition may be administered once, on a continuous basis (e.g. by an intravenous drip), or on a periodic/intermittent basis, including about once per hour, about once per two hours, about once per four hours, about once per eight hours, about once per twelve hours, about once per day, about once per two days, about once per three days, about twice per week, about once per week, and about once per month. The composition may be administered until a desired reduction of symptoms is achieved.

The present compounds, compositions, and methods may be administered as part of a therapeutic regimen along with other treatments appropriate for the particular injury or disease being treated.

In certain embodiments, the disclosed compounds and compositions can be used in combination with an additional pharmaceutical agent or dosage form. The disclosed compounds and compositions may be administered as part of a regimen additionally including any other pharmaceutical agent and/or pharmaceutical dosage form (e.g., an additional active agent that is effective for the treatment of a cancer, malignancy, or proliferative disorder). An additional pharmaceutically active ingredient or additional pharmaceutical dosage form can be administered to a patient either directly or indirectly, and concomitantly or sequentially, with the compounds and compositions disclosed herein. In certain embodiments, the disclosed compounds and compositions can be used in combination with one or more Hsp90 inhibitors (e.g., 2-(((1r,4r)-4-hydroxycyclohexyl)amino)-4-(3,6,6-trimethyl-4-oxo-4,5,6,7-tetrahydro-1H-indazol-1-yl)benzamide).

In certain embodiments, the disclosed compounds and compositions can be used in combination with an anti-cancer/chemotherapeutic agent. Exemplary agents include, but are not limited to, alkylating agents (including, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), bendamustine (Treakisym®, Ribomustin®, Treanda®) chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexylen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), estramustine (Emcyt®, Estracit®), fotemustine, irofulven, mannosulfan, mitobronitol, nimustine, procarbazine, ranimustine, semustine, triaziquone, treosulfan, and Dacarbazine (DTIC-Dome®); anti-EGFR antibodies (e.g., cetuximab (Erbitux®), panitumumab (Vectibix®), and gefitinib (Iressa®)); anti-Her-2 antibodies (e.g., trastuzumab (Herceptin®) and other antibodies from Genentech); antimetabolites (including, without limitation, folic acid antagonists (also referred to herein as antifolates), pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), carmofur, cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), mercaptopurine (Puri-Nethol®), capecitabine (Xeloda®), nelarabine (Arranon®), azacitidine (Vidaza®), decitabine (Dacogen®), enocitabine (Sunrabin®), sapacitabine, tegafur-uracil, tiazofurine, tioguanine, trofosfamide, and gemcitabine (Gemzar®); vinca alkaloids: vinblastine (Velban®, Velsar®), vincristine (Vincasar®, Oncovin®), vindesine (Eldisine®), vinorelbine (Navelbine®), vinflunine (Javlor®); platinum-based agents: carboplatin (Paraplat®, Paraplatin®), cisplatin (Platinol®), oxaliplatin (Eloxatin®), nedaplatin, satraplatin, triplatin; anthracyclines: daunorubicin (Cerubidine®, Rubidomycin®), doxorubicin (Adriamycin®), epirubicin (Ellence®), idarubicin (Idamycin®), mitoxantrone (Novantrone®), valrubicin (Valstar®), aclarubicin, amrubicin, liposomal doxorubicin, liposomal daunorubicin, pirarubicin, pixantrone, zorubicin; topoisomerase inhibitors: topotecan (Hycamtin®), irinotecan (Camptosar®), etoposide (Toposar®, VePesid®), teniposide (Vumon®), lamellarin D, SN-38, camptothecin (e.g., IT-101), belotecan, rubitecan; taxanes: paclitaxel (Taxol®), docetaxel (Taxotere®), larotaxel, cabazitaxel, ortataxel, tesetaxel; antibiotics: actinomycin (Cosmegen®), bleomycin (Blenoxane®), hydroxyurea (Droxia®, Hydrea®), mitomycin (Mitozytrex®, Mutamycin®); immunomodulators: lenalidomide (Revlimid®), thalidomide (Thalomid®); immune cell antibodies: alemtuzamab (Campath®), gemtuzumab (Myelotarg®), rituximab (Rituxan®), tositumomab (Bexxar®); interferons (e.g., IFN-alpha (Alferon®, Roferon-A®, Intron®-A) or IFN-gamma (Actimmune®)); interleukins: IL-1, IL-2 (Proleukin®), IL-24, IL-6 (Sigosix®), IL-12; HSP90 inhibitors (e.g., geldanamycin, 17-alkylamino-17-desmethoxygeldanamycin ("17-AAG") or 17-(2-dimethylaminoethyl)amino-17-desmethoxygeldanamycin ("17-DMAG"); anti-androgens which include, without limitation nilutamide (Nilandron®) and bicalutamide (Caxodex®); antiestrogens which include, without limitation tamoxifen (Nolvadex®), toremifene (Fareston®), letrozole (Ferrara®), testolactone (Teslac®), anastrozole (Arimidex®), bicalutamide (Casodex®), exemestane (Aromasin®), flutamide (Eulexin®), fulvestrant (Faslodex®), raloxifene (Evista®, Keoxifene®) and raloxifene hydrochloride; anti-hypercalcaemia agents which include without limitation gallium (III) nitrate hydrate (Ganite®) and pamidronate disodium (Aredia®); apoptosis inducers which include without limitation ethanol, 2-[[3-(2, 3-dichlorophenoxy)propyl]amino]-(9Cl), gambogic acid, elesclomol, embelin and arsenic trioxide (Trisenox®); Aurora kinase inhibitors which include without limitation binucleine 2; Bruton's tyrosine kinase inhibitors which include without limitation terreic acid; calcineurin inhibitors which include without limitation cypermethrin, deltamethrin, fenvalerate and tyrphostin 8; CaM kinase II inhibitors which include without limitation 5-Isoquinolinesulfonic acid, 4-[{2S)-2-[(5-isoquinolinylsulfonyl)methylamino]-3-oxo-3-{4-phenyl-1-pipe-razinyl)propyl]phenyl ester and benzenesulfonamide; CD45 tyrosine phosphatase inhibitors which include without limitation phosphonic acid; CDC25 phosphatase inhibitors which include without limitation 1,4-naphthalene dione, 2,3-bis[(2-hydroxyethyl)thio]-(9Cl); CHK kinase inhibitors which include without limitation debromohymenialdisine; cyclooxygenase inhibitors which include without limitation 1H-indole-3-acetamide, 1-(4-chlorobenzoyl)-5-methoxy-2-methyl-N-(2-phenylethyl)-(9Cl), 5-alkyl substituted 2-arylaminophenylacetic acid and its derivatives (e.g., celecoxib (Celebrex®), rofecoxib (Vioxx®), etoricoxib (Arcoxia®), lumiracoxib (Prexige®), valdecoxib (Bextra®) or 5-alkyl-2-arylaminophenylacetic acid); cRAF kinase inhibitors which include without limitation 3-(3,5-dibromo-4-hydroxybenzylidene)-5-iodo-1,3-dihydroindol-2-one and benzamide, 3-(dimethylamino)-N-[3-[(4-hydroxybenzoyl)amino]-4-methylphenyl]-(9Cl); cyclin dependent kinase inhibitors which include without limitation olomoucine and its derivatives, purvalanol B, roascovitine (Seliciclib®), indirubin, kenpaullone, purvalanol A and indirubin-3'-monooxime; cysteine protease inhibitors which include without limitation 4-morpholinecarboxamide, N-[(1S)-3-fluoro-2-oxo-1-(2-phenylethyl)propyl]amino]-2-oxo-1-(phenylmeth-yl)ethyl]-(9Cl); DNA intercalators which include without limitation plicamycin (Mithracin®) and daptomycin (Cubicin®); DNA strand breakers which include without limitation bleomycin (Blenoxane®); E3 ligase inhibitors which include without limitation N-((3,3,3-trifluoro-2-trifluoromethyl)propionyl)sulfanilamide; EGF Pathway Inhibitors which include, without limitation tyrphostin 46, EKB-569, erlotinib (Tarceva®), gefitinib (Iressa®), lapatinib (Tykerb®) and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980; farnesyltransferase inhibitors which include without limitation a-hydroxyfarnesylphosphonic acid, butanoic acid, 2-[(2S)-2-[[(2S,3S)-2-[[(2R)-2-amino-3-mercaptopropyl]amino]-3-methylpent-yl]oxy]-1-oxo-3-phenylpropyl]amino]-4-(methylsulfonyl)-1-methylethylester (2S)-(9Cl), tipifarnib (Zarnestra®), and manumycin A; Flk-1 kinase inhibitors which include without limitation 2-propenamide, 2-cyano-3-[4-hydroxy-3,5-bis(1-methylethyl)phenyl]-N-(3-phenylpropyl)-(2E-)-(9Cl); glycogen synthase kinase-3 (GSK3) inhibitors which include without limitation indirubin-3'-monooxime; histone deacetylase (HDAC) inhibitors which include without limitation suberoylanilide hydroxamic acid (SAHA), [4-(2-amino-phenylcarbamoyl)-benzyl]-carbamic acid pyridine-3-ylmethylester and its derivatives, butyric acid, pyroxamide, trichostatin A, oxamflatin, apicidin, depsipeptide, depudecin, trapoxin, vorinostat (Zolinza®), and compounds disclosed in WO 02/22577; I-kappa B-alpha kinase inhibitors (IKK) which include without limitation 2-propenenitrile, 3-[(4-methylphenyl)sulfonyl]-(2E)-(9Cl); imidazotetrazinones which include without limitation temozolomide (Methazolastone®, Temodar® and its derivatives (e.g., as disclosed generically and specifically in U.S. Pat. No. 5,260,291) and Mitozolomide; insulin tyrosine kinase inhibitors which include without limitation hydroxyl-2-naphthalenylmethylphosphonic acid; c-Jun-N-terminal kinase (JNK) inhibitors which include without limitation pyrazoleanthrone and epigallocatechin gallate; mitogen-activated protein kinase (MAP) inhibitors which include without limitation benzenesulfonamide, N-[2-[[[3-(4-chlorophenyl)-2-propenyl]methyl]amino]methyl]phenyl]-N-(2-hydroxyethyl)-4-methoxy-(9Cl); MDM2 inhibitors which include without limitation trans-4-iodo, 4'-boranyl-chalcone; MEK inhibitors which include without limitation butanedinitrile, bis[amino[2-aminophenyl)thio]methylene]-(9Cl); MMP inhibitors which include without limitation Actinonin, epigallocatechin gallate, collagen peptidomimetic and non-peptidomimetic inhibitors, tetracycline derivatives marimastat (Marimastat®), prinomastat, incyclinide (Metastat®), shark cartilage extract AE-941 (Neovastat®), Tanomastat, TAA211, MMI270B or AAJ996; mTor inhibitors which include without limitation rapamycin (Rapamune®), and analogs and derivatives thereof, AP23573 (also known as ridaforolimus, deforolimus, or MK-8669), CCI-779 (also known as temsirolimus) (Torisel®) and SDZ-RAD; NGFR tyrosine kinase inhibitors which include without limitation tyrphostin AG 879; p38 MAP kinase inhibitors which include without limitation Phenol, 4-[4-(4-fluorophenyl)-5-(4-pyridinyl)-1H-imidazol-2-yl]-(9Cl), and benzamide, 3-(dimethylamino)-N-[3-[(4-hydroxybenzoyl)amino]-4-methylphenyl]-(9Cl); p56 tyrosine kinase inhibitors which include without limitation damnacanthal and tyrphostin 46; PDGF pathway inhibitors which include without limitation tyrphostin AG 1296, tyrphostin 9, 1,3-butadiene-1,1,3-tricarbonitrile, 2-amino-4-(1H-indol-5-yl)-(9Cl), imatinib (Gleevec®) and gefitinib (Iressa®) and those compounds generically and specifically disclosed in European Patent No.: 0 564 409 and PCT Publication No.: WO 99/03854; phosphatidylinositol 3-kinase inhibitors which include without limitation wortmannin, and quercetin dehydrate; phosphatase inhibitors which include without limitation cantharidic acid, cantharidin, and L-leucinamide; protein phosphatase inhibitors which include without limitation cantharidic acid, cantharidin, L-P-bromotetramisole oxalate, 2(5H)-furanone, 4-hydroxy-5-(hydroxymethyl)-3-(1-oxohexadecyl)-(5R)-(9Cl) and benzylphosphonic acid; PKC inhibitors which include without limitation 1-H-pyrollo-2,5-dione,3-[1-3-(dimethylamino)propyl]-1H-indol-3-yl]-4-(1H-indol-3-yl)-(9Cl), Bis-indolylmaleimide IX, Sphinogosine, staurosporine, and Hypericin; PKC delta kinase inhibitors which include without limitation rottlerin; polyamine synthesis inhibitors which include without limitation DMFO; PTP1B inhibitors which include without limitation L-leucinamide; protein tyrosine kinase inhibitors which include, without limitation tyrphostin Ag 216, tyrphostin Ag 1288, tyrphostin Ag 1295, geldanamycin, genistein and 7H-pyrrolo[2,3-d]pyrimidine derivatives as generically and specifically described in PCT Publication No.: WO 03/013541 and U.S. Publication No.: 2008/0139587; SRC family tyrosine kinase inhibitors which include without limitation PP1 and PP2; Syk tyrosine kinase inhibitors which include without limitation piceatannol; Janus (JAK-2 and/or JAK-3) tyrosine kinase inhibitors which include without limitation tyrphostin AG 490 and 2-naphthyl vinyl ketone; retinoids which include without limitation isotretinoin (Accutane®, Amnesteem®, Cistane®, Claravis®, Sotret®) and tretinoin (Aberel®, Aknoten®, Avita®, Renova®, Retin-A®, Retin-A MICRO®, Vesanoid®); RNA polymerase II elongation inhibitors which include without limitation 5,6-dichloro-1-beta-D-ribofuranosylbenzimidazole; serine/Threonine kinase inhibitors which include without limitation 2-aminopurine; sterol biosynthesis inhibitors which include without limitation squalene epoxidase and CYP2D6; VEGF pathway inhibitors, which include without limitation anti-VEGF antibodies, e.g., bevacizumab, and small molecules, e.g., sunitinib (Sutent®), sorafinib (Nexavar®), ZD6474 (also known as vandetanib) (Zactima™), SU6668, CP-547632 and AZD2171 (also known as cediranib) (Recentin™).

Examples of chemotherapeutic agents are also described in the scientific and patent literature, see, e.g., Bulinski (1997) J. Cell Sci. 110:3055-3064; Panda (1997) Proc. Natl. Acad. Sci. USA 94:10560-10564; Muhlradt (1997) Cancer Res. 57:3344-3346; Nicolaou (1997) Nature 387:268-272; Vasquez (1997) Mol. Biol. Cell. 8:973-985; Panda (1996) J. Biol. Chem. 271:29807-29812.

Other exemplary anti-cancer agents include alitretinon, altretamine, aminopterin, aminolevulinic acid, amsacrine (Amsidine®), asparaginase (crisantaspase, Erwinase®), atrasentan, bexarotene (Targretin®), carboquone, demecolcine, efaproxiral, elsamitrucin, etoglucid, ferrocene, Gliadel implants, hydroxycarbamide, leucovorin, lonidamine, lucanthone, masoprocol, methyl aminolevulinate, mitoguazone, mitotane (Lysodren®), oblimersen, omacetaxine (Genasense®), pegaspargase (Oncaspar®), porfimer sodium (Photofrin®), prednimustine, sitimagene ceradenovec (Cerepro®), talaporfin, temoporfin, trabectedin (Yondelis®), and verteporfin.

6. Examples

The compounds, compositions, processes, and methods of the invention will be better understood by reference to the following examples, which are intended as an illustration of and not a limitation upon the scope of the invention.

A. Synthetic Methods

Example 1

(S)-1-(pyrazin-2-yl)piperidine-3-carboxylic acid

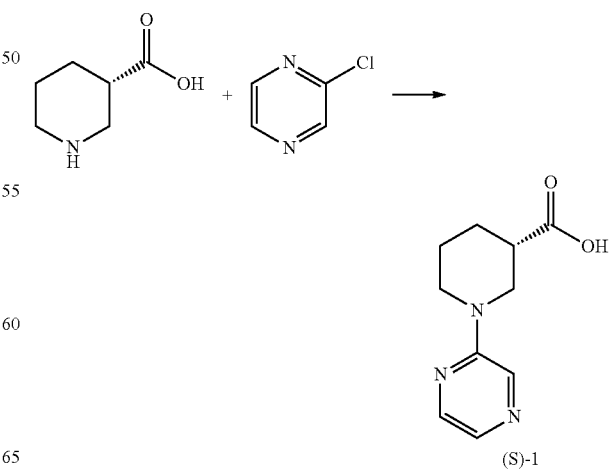

(S)-1-(pyrazin-2-yl)piperidine-3-carboxylic acid (S)-1. (S)-(+)-3-Piperidinecarboxylic acid (250 mg, 1.94 mmol) and chloropyrazine (441 mg, 3.87 mmol) were heated together with Hunig's base (500 mg, 3.87 mmol) and ethanol (300 uL) at 120° C. for 16 h. TLC (4/1/1: nBuOH/AcOH/H₂O) showed a new product and only a trace of starting material. The reaction mixture was concentrated, dissolved in DMSO and purified by prep HPLC (5 to 100% methanol w/0.2% formic acid, 20 mL/m, Agilent C-18, 21.1×25 cm) to give product (S)-1 (291 mg, 72%) as a white powder. MS (ESI) [M+H]⁺ m/z=208.0.

Example 2

(S)—N-(1H-benzo[d]imidazol-2-yl)-1-(pyrazin-2-yl)piperidine-3-carboxamide

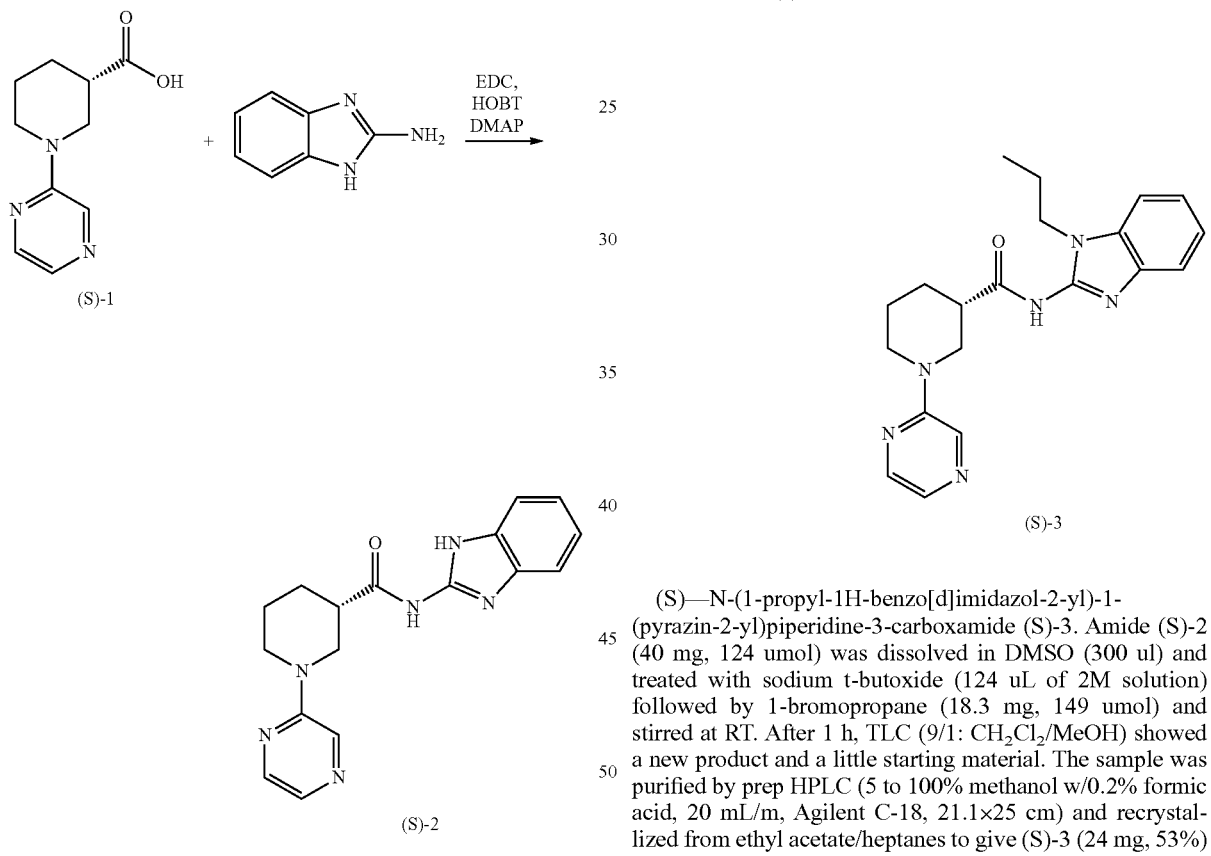

(S)—N-(1H-benzo[d]imidazol-2-yl)-1-(pyrazin-2-yl)piperidine-3-carboxamide (S)-2. Compound (S)-1 (147 mg, 709 umol) and 2-aminobenzimidazole (189 mg, 1.42 mmol) were mixed with EDC (204 mg, 1.06 mmol), HOBT (96 mg, 0.71 mmol) and DMAP (9 mg, 71 mmol) and Hunig's base (183 mg, 247 mL, 1.4 mmol) and dissolved in DMF (2 mL). TLC (9/1: CH₂Cl₂/MeOH) showed the slow formation of product and loss of starting material. After 2 h, the reaction mixture was concentrated to remove DMF and chromatographed (gradient CH₂Cl₂ to 9/1: CH₂Cl₂/MeOH). The product was triturated overnight in ethyl acetate/hexanes to give (S)-2 (77.8 mg, 34%) as a white solid. MS (ESI) [M+H]⁺ m/z=323.2.

Example 3

(S)—N-(1-propyl-1H-benzo[d]imidazol-2-yl)-1-(pyrazin-2-yl)piperidine-3-carboxamide

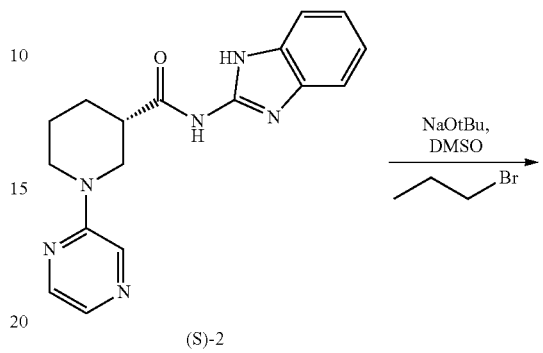

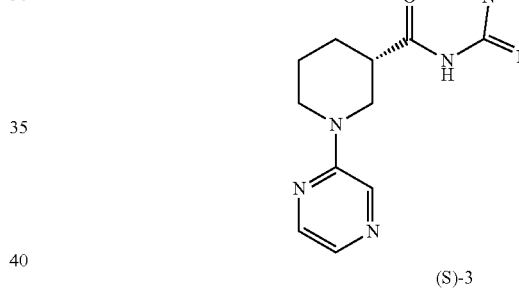

(S)—N-(1-propyl-1H-benzo[d]imidazol-2-yl)-1-(pyrazin-2-yl)piperidine-3-carboxamide (S)-3. Amide (S)-2 (40 mg, 124 umol) was dissolved in DMSO (300 ul) and treated with sodium t-butoxide (124 uL of 2M solution) followed by 1-bromopropane (18.3 mg, 149 umol) and stirred at RT. After 1 h, TLC (9/1: CH₂Cl₂/MeOH) showed a new product and a little starting material. The sample was purified by prep HPLC (5 to 100% methanol w/0.2% formic acid, 20 mL/m, Agilent C-18, 21.1×25 cm) and recrystallized from ethyl acetate/heptanes to give (S)-3 (24 mg, 53%) as a white powder. (S)-3 was identical to commercial racemic 3 by TLC and LC/MS. MS (ESI) [M+H]⁺ m/z=365.3.

Example 4

(R)—N-(1-propyl-1H-benzo[d]imidazol-2-yl)-1-(pyrazin-2-yl)piperidine-3-carboxamide HS-71, (R)—N-(1-propyl-1H-benzo[d]imidazol-2-yl)-1-(pyrazin-2-yl)piperidine-3-carboxamide, (R)-3, was prepared in an analogous manner from (R)-(−)-3-piperidinecarboxylic acid.

Example 5

Synthesis of HS-72 affinity resin (S)-9

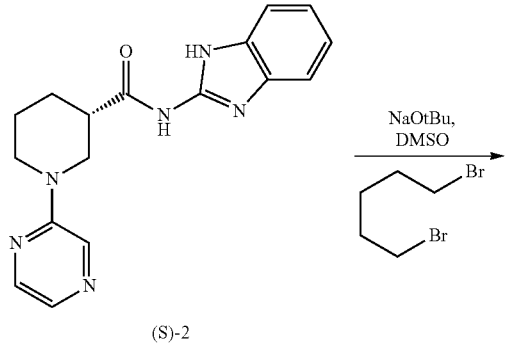

(S)-2

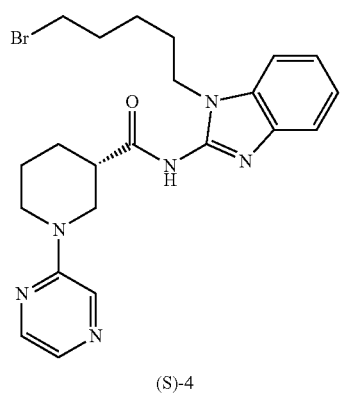

(S)-4

(S)—N-(1-(5-bromopentyl)-1H-benzo[d]imidazole-2-yl)-1-(pyrazin-2-yl)piperidine-3-carboxamide (S)-4. Amide (S)-2 (20 mg, 62 µmol) was dissolved in DMSO (300 µL) and treated with sodium t-butoxide (62 µl of 2 M solution) followed by 1,5-dibromopentane (17 mg, 74 µmol) and stirred at room temperature. After about 1 h, TLC (9/1: CH$_2$Cl$_2$/MeOH) and LC/MS showed a new product (m/z=471.6). The product was purified by prep HPLC (5 to 100% methanol with 0.2% formic acid, 20 mL/m, Agilent C-18, 21.1×25 cm) to give (S)-4 as a yellow solid. The product was then used for the next reaction.

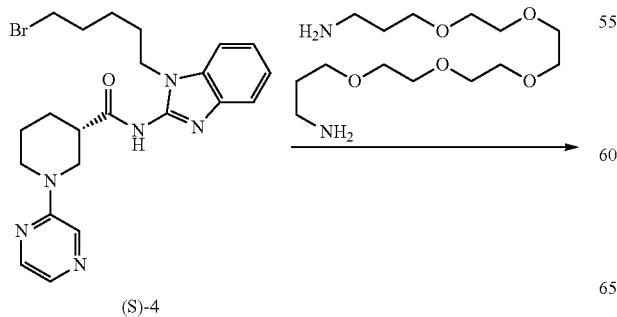

(S)-4

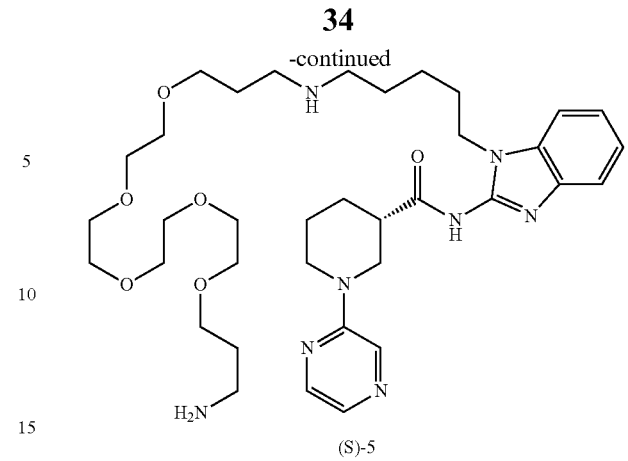

(S)-5

(S)—N-(1-(1-amino-4,7,10,13,16-pentaoxa-20-azapentacosan-25-yl)-1H-benzo[d]imidazole-2-yl)-1-(pyrazin-2-yl)piperidine-3-carboxamide (S)-5. Bromide (S)-4 (20 mg, 62 µmol) was dissolved in ethanol (2 mL) and treated with 1,19-diamino-4,7,10,13,17-pentaoxanonadecane (60 mg, 195 µmol) followed by DMSO (100 µL) and CH$_2$Cl$_2$ (1 mL) and stirred at room temperature for 3 days. The reaction mixture was concentrated and injected onto the prep HPLC (5 to 100% methanol, 20 mL/m, Agilent C-18, 21.1×25 cm) to give purified (S)-5 (12.9 mg, 30% from (S)-2) as a glass. LC/MS gives m/z=669.4 [M+H]$^+$.

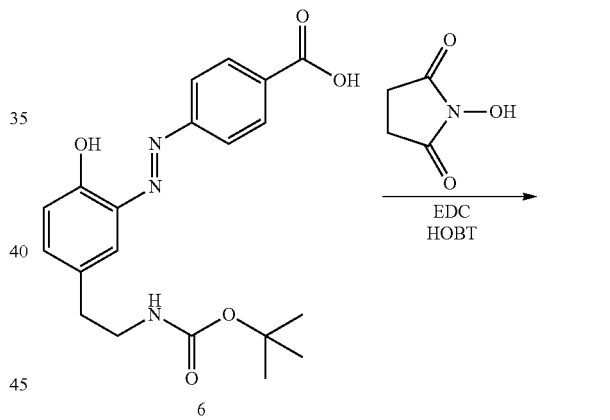

6

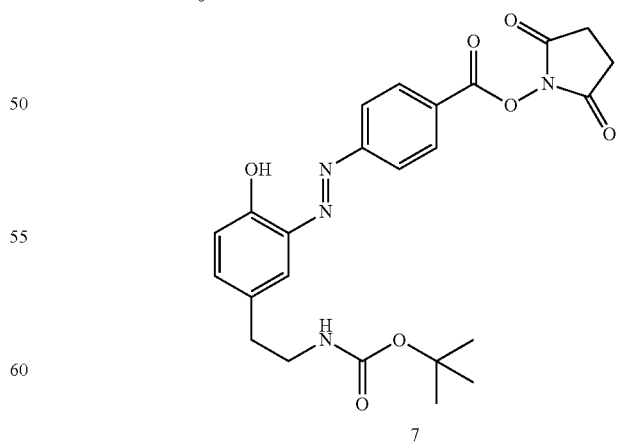

7

Active cleavable linker 7. The cleavable linker acid [Hughes et al., 2012] 6 (541 mg, 1.4 mmol), EDC (540 mg, 2.8 mmol) and N-hydroxysuccinimide (243 mg, 2.1 mmol)

and a chip of DMPA were slurried in dichloromethane (10 mL) and DMF (1.5 mL). After 16 hour, TLC (70% ethyl acetate in hexanes) showed complete reaction. The reaction mixture was added to a column and chromatographed (silica gel, 18×3.5 cm, CH$_2$Cl$_2$ (200 mL), 25% EtOAc in CH$_2$Cl$_2$ (600 mL). The active fractions were combined and concentrated then triturated with hexanes/ethyl acetate and filtered off to give the 7 (353 mg, 52%) as an orange powder.

Hunig's base (10 µL). After stirring overnight, TLC showed mostly one product and LC/MS showed a big peak in the TIC with the right mass. UV showed nothing at 254 nm as usual. The sample was concentrated to an oil and chromatographed on silica gel eluting with a CH$_2$Cl$_2$ to 4/0.9/0.1: CH$_2$Cl$_2$/MeOH/NH$_3$ gradient. The product was concentrated to give an orange glass. The sample was then dissolved in methylene chloride (1 mL) and TFA (1 mL). After

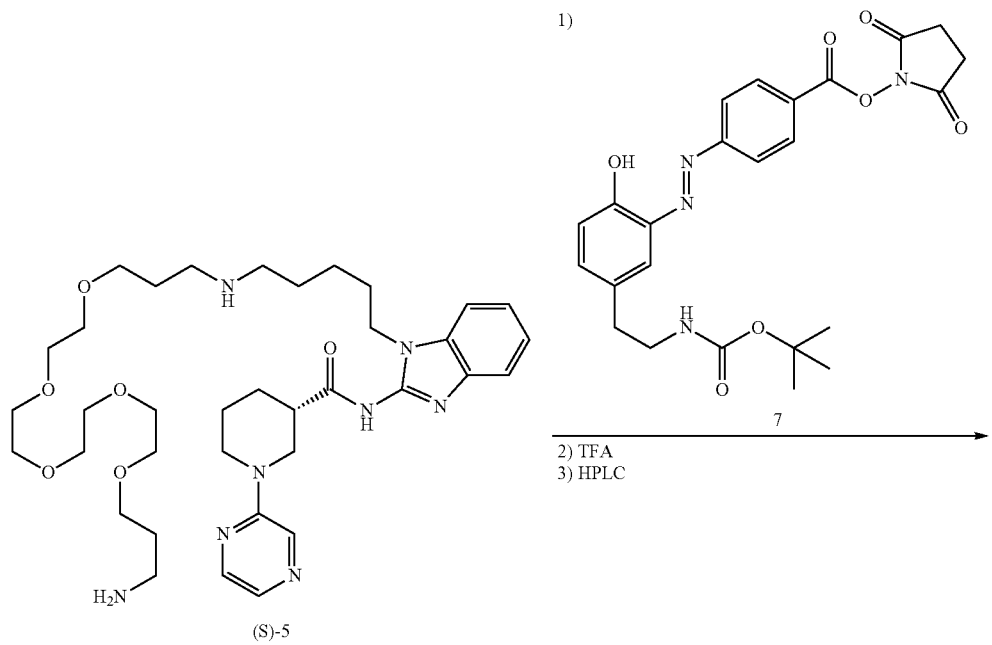

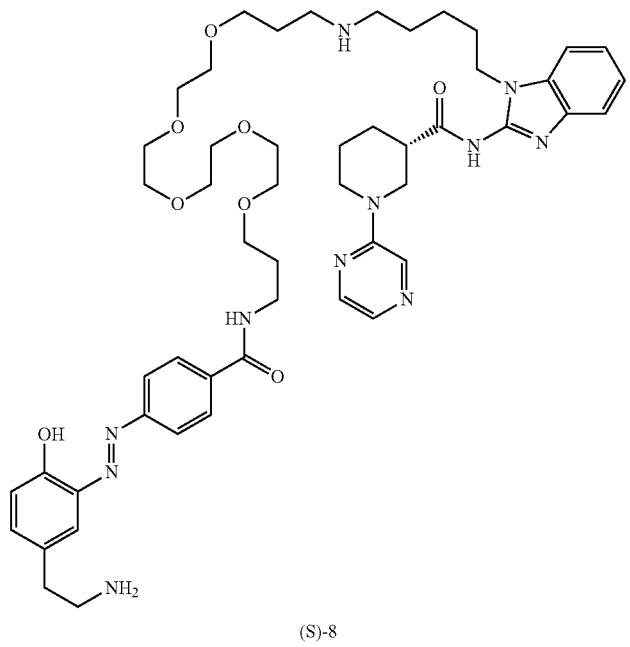

Amine (S)-8. Amine (S)-5 (12.9 mg, 18.5 µmol) was dissolved 9/1: DCM/MeOH (1 mL) and treated with solid activated cleavable linker 7 (25 mg, 52 µmol), followed by 1 h, TLC (4/0.9/0.1: CH$_2$Cl$_2$/MeOH/NH$_3$) showed a new product. The mixture was concentrated, diluted with ethanol and concentrated again and then purified by HPLC (5 to 100% methanol, 20 mL/m, Agilent C-18, 21.1×25 cm) to give amine (S)-8 (5.5 mg, 31% overall) as an orange glass. LC/MS showed a single peak with m/z=966.6 [M+H]$^+$.

Affinity resin (S)-9. In a 300 mL column, CNBr-activated Sepharose™ 4B (2 g) was swelled in 1 mM HCl (20 ml) and then washed with 1 mM HCl (400 mL). The resin was

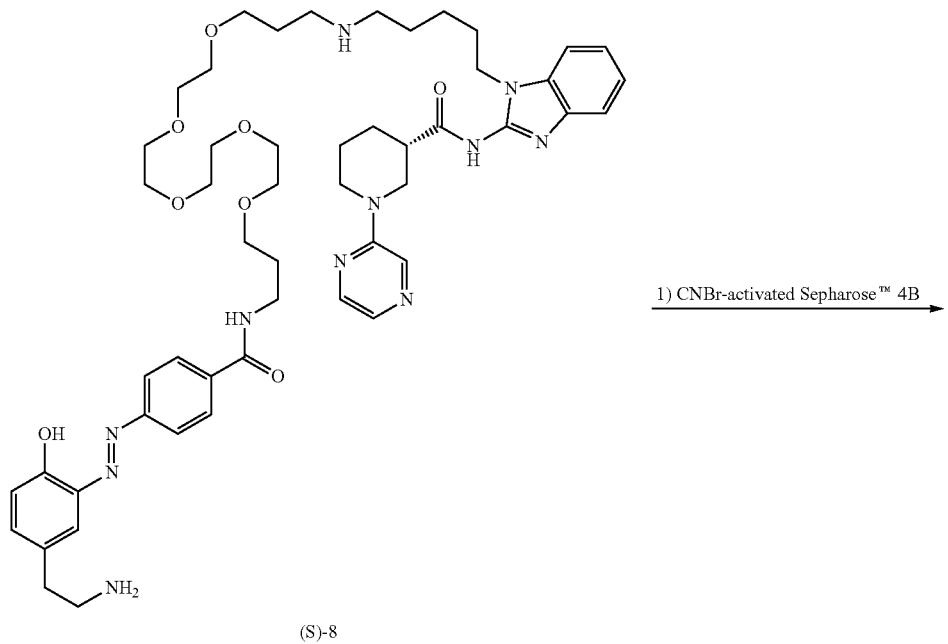

(S)-8

1) CNBr-activated Sepharose™ 4B

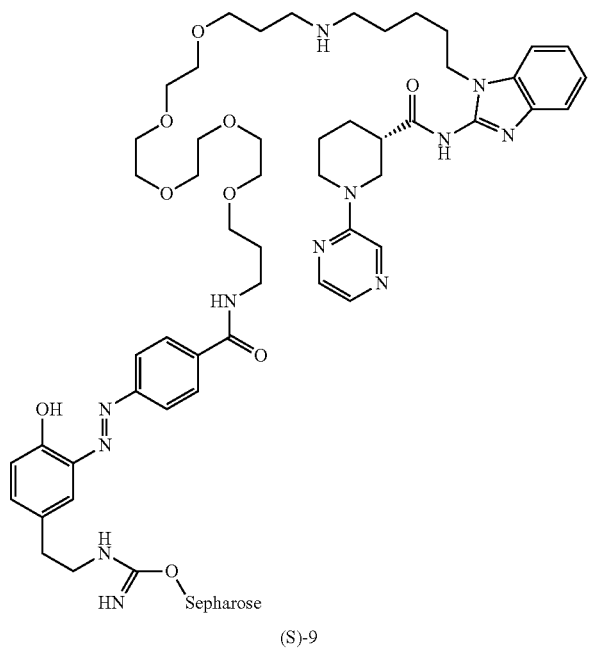

(S)-9

Buffers and Solutions:

| | |
|---|---|
| Swelling solution | 1 mM HCl; |
| Coupling buffer | 0.1M NaHCO$_3$, 0.5M NaCl, pH = 8.3; |
| Capping solution | 1M ethanolamine; |
| Low buffer | 0.1M AcOH/NaAcOH, 0.5M NaCl pH = 4; |
| High buffer | 0.1M TRIS-HCl, 0.5M NaCl pH = 8; |
| Storage buffer | 0.1M KH$_2$PO$_4$, pH = 7.4 w/200 mg NaN$_3$/L. | washed with coupling buffer (20 mL) and then slurried with coupling buffer (10 mL). The mixture was then treated with amine (S)-8 (5.5 mg) in ethanol (1 mL) and tumbled at room temperature for 16 h. The resin was then drained (no color eluted) and washed with coupling buffer (5×10 mL), diluted with more coupling buffer (~10 mL) and treated with capping solution (200 μL) and rotated for 2 h. The solution was drained and the resin (S)-9 washed with 3 rounds of high buffer/low buffer (20 mL each) and finally washed with water (20 mL) and transferred in storage buffer (10 mL) to a 40 mL EPA vial and stored at 4° C.

B. Biological Data

Materials and Methods

Cell Lines: HEK-293T (ATCC® ACS-4500™), MCF7 (ATCC® HTB-22™), HeLa (ATCC® CCL-2™), HepG2 (ATCC® HB-8065™), T47D (ATCC® CRL-2865™) and NF639 (ATCC® CRL-3090™) cell lines were obtained from ATCC and are grown in DMEM medium supplemented with 10% FBS. BT474, SkBr3, LNCaP, and RWPE1 cell lines were obtained and were grown in RPMI-1640 medium supplemented with 10% FBS and non-essential amino acids. MCF-10A cell line was obtained and was grown in DMEM/F12 medium supplemented with 5% horse serum, 0.02% EGF, 0.05% Hydrocortisone, 0.01% Cholera Toxin, 0.1% Insulin, and 1% penicillin/streptomycin. PC12 cell line expressing httQ74-GFP was obtained was grown in DMEM supplemented with 5% FBS, 10% horse serum, 100 ug/ml G418, 75 ug/ml Hygromycin B, and 100 U/ml penicillin/streptomycin plus supplements [Neef, D. W., Turski, M. L., and Thiele, D. J. (2010). Modulation of heat shock transcription factor 1 as a therapeutic target for small molecule intervention in neurodegenerative disease. PLoS biology 8, e1000291]. All cell lines were grown at 37° C. in an atmosphere of 5% $CO_2$.

Western Blotting: SDS-PAGE was carried out using Criterion™ Cell system using pre-casted 4-20% or 4-15% Criterion™ Tris-HCl gels (BioRad, Hercules, Calif.). For Western blotting gels were run at 200V for 1 hour using the PowerPac basic power supply (BioRad, Hercules, Calif.). Next, gels were transferred to nitrocellulose for blotting at 100V for 1 hour (Fisher Scientific, Waltham, Mass.). Nitrocellulose membranes were blocked with 5% dry non-fat milk in phosphate-buffered saline (PBS) with 0.01% Tween-20 for 1 hour at room temperature. Membranes were incubated with primary antibodies (1:1000 dilution) overnight at 4° C. The next day membranes were washed 3× in PBS-Tween, incubated for 1 hour at room temperature with secondary antibodies, and further washed 3× in PBS-Tween. ECL Plus Western blotting reagent (Pierce Biotechnology, Rockford, Ill.) was used to detect antibodies. GFP, Her2, Akt, Hsp70, Hsc70, Grp78, Grp75, and Hsp90 primary antibodies and all associated secondary antibodies were purchased from Cell Signaling Technology (Danvers, Mass.).

Protein Purification: Plasmids were provided for human HSPA1A, HSPA8, and HSPA1A C306D. Plasmids were transformed in Rosetta competent cells and single colonies were picked from streaked LB/ampicillin/chloramphenicol plates. Cultures were grown at 37° C. for 4-6 hours, were cooled to 15° C. and expression was induced overnight with 200 uM isopropyl 1-thio-β-D-galactopyranoside. Cells were pelleted and resuspended in Ni-lysis buffer (50 mM $Na_2HPO_4$, 300 mM NaCl, 10 mM Imidazole, 0.05% Tween-20) supplemented with Complete Mini protease inhibitor tablets (Roche, Mannheim, Germany) and 1M DTT, and then sonicated. The cells were again pelleted and the supernatant was incubated with complete His-Tag purification resin (Roche, Mannheim, Germany) for 5 hours at 4° C. The resin was washed with Ni-wash buffer (50 mM $Na_2HPO_4$, 300 mM NaCl, 20 mM Imidazole, 0.05% Tween-20) and eluted with Ni-elution buffer (50 mM $Na_2HPO_4$, 300 mM NaCl, 250 mM Imidazole, 0.05% Tween-20). The elution was then incubated with tobacco etch virus protease overnight at 4° C. The following day the elution was incubated with the γ-phosphate ATP sepharose resin for 30 minutes at 4° C. Next the resin was washed with ATP-wash buffer (50 mMTris-HCl, 60 mM $MgCl_2$, 60 mM KCl, 10 mM Citrate) supplemented with 1 mM DTT and then ATP-wash buffer supplemented with 2 mM ATP was added to the resin to elute the protein. The final elutions were concentrated in Amicon Ultra-15 Centrifugal Filter Units (EMD Millipore, Billerica, Mass.) and buffer exchanged into 25 mM HEPES, 5 mM $MgCl_2$, 10 mM KCl (pH 7.5) and stored at −80° C. until use.

Endogenous Hsp70 elution: Pig bladder tissue was used for eluting endogenous Hsp70 from the γ-phosphate ATP sepharose resin. Tissue was homogenized in liquid nitrogen and stored at −80° C. until further use. Tissue mass was measured (g) and then 2.5× volume (mL) of tissue lysis buffer (50 mM HEPES, 60 mM $MgCl_2$, 60 mM KCl, 1 mM DTT) was added and homogenized on a laboratory blender. A total of 25 grams of homogenized tissue was typically used for each experiment. Subsequent to lysis, the tissue was centrifuged at 35,000 RPM in a Beckman Type 45 Ti rotor (Brea, Calif.) for 45 minutes at 4° C., and then filtered over silica wool. The filtered supernatant was then added to the γ-phosphate ATP sepharose resin and washed as previously described in the FLECS screen. Compounds were used to elute Hsp70 and the elutions were then separated by SDS-PAGE and analyzed by Western blot or the gels were visualized by silver stain.

Degradation Assay: The specified cells were seeded overnight and then treated with the indicated concentration of compound for 24 hours. The cells were then harvested and subjected to analysis by Western blot.

Cell Proliferation: Cell proliferation was determined using a Hoechst stain (Sigma, St. Louis, Mo.) to quantify DNA. 5,000 cells of the designated cell line were plated in 96 well plates and treated the next day, designated as time point 0, with the indicated concentration of the specified compound maintained for the duration of the assay. At the indicated time points the media was removed and plated frozen at −80° C. Double distilled $H_2O$ was then added and the plates were incubated at 37° C. for 1 hour. After 1 hour the plates were frozen at −80° C. After freezing the plates were thawed and Hoechst stain was diluted 1:1000 in THE buffer (10 mM Tris, 2M NaCl, 1 mM $Na_2EDTA$). The final fluorescence was measured on the Victor X2 plate reader at 355/460 nm, and cell proliferation was determined with the formula: % Cell Proliferation=100×(Sample fluorescence−background fluorescence)/(Control fluorescence−background fluorescence).

Mass Spectrometry: Tryptic peptides were subjected to matrix-assisted laser desorption-ionization mass spectrometry (MALDI-MS) on an ABSCIEX TOF/TOF 5800 mass spectrometer. Positive mode time of flight was used to identify peptides, and individual peptides were sequenced by MS/MS. All sequence and peptide fingerprint data was searched using the UniProt database.

ATPase Assay: Single turnover assays were performed as previously described [Fewell et al. (2004). Small molecule modulators of endogenous and co-chaperone-stimulated Hsp70 ATPase activity. The Journal of biological chemistry 279, 51131-51140]. Briefly, Hsp70 was incubated with $^{32}P$-ATP and cold ATP in single turnover buffer (1M KCl, 250 mM HEPES, 110 mM MgOAc) for 30 minutes on ice. $^{32}P$-ATP-Hsp70 complex was purified from a Nick Column-Sephadex G-50 (Amersham, Piscataway, N.J.). Glycerol was added and the complexes were stored at −80° C. To determine ATP hydrolysis, a sample was thawed and added to single turnover buffer containing Hlj1 and compound added after 60 seconds. At the specified time points an aliquot of the reaction is removed, added to stop solution (2M LiCl, 4M formic acid, 36 mM ATP) and spotted on a TLC plate. The percentage of ATP hydrolyzed to ADP and P, was then calculated.

Limited Proteolysis: Limited proteolysis was performed as previously described [Seguin, S. P., Ireland, A. W., Gupta, T., Wright, C. M., Miyata, Y., Wipf, P., Pipas, J. M., Gestwicki, J. E., and Brodsky, J. L. (2012). A screen for modulators of large T antigen's ATPase activity uncovers novel inhibitors of Simian Virus 40 and BK virus replication. Antiviral research 96, 70-81]. Briefly, 4 ug of purified Hsp70i was incubated with HS-72, DMSO, and/or the indicated nucleotide for 20 minutes on ice. 1.8 ng of Proteinase K was added and incubated at 37° C. for 5 minutes. The reaction was quenched with 100% TCA and incubated for 10 minutes on ice. Reactions were centrifuged for 10 minutes at 13,000 rpm at 4° C. and the supernatants were removed. The pellets were resuspended in TCA sample buffer (80 mM Tris HCl pH 8, 8 mM EDTA, 120 mM DTT, 3.5% SDS, 0.29% glycerol, 0.08% Tris base, 0.01% bromophenol blue), separated by SDS-PAGE, and visualized by silver stain.

HS-72 in vivo MTD and blood workup: The 5 cohorts consisted of 3 mice each given HS-72 BiW and administered IP in DMSO at 1, 5, 10, 20 and 30 mpk using female FVBs aged to 10 weeks. Body Mass was measured weekly and the mice were monitored for signs of toxicity as per MP1U standard protocol. For blood analysis, 4 mice were injected IP with HS-72 on day 1 and 4, with blood drawn on day 5. 4 mice receiving no treatment were used as controls.

HS-72 PK: Wild-type mice were injected IP with HS-72 and sacrificed 5 minutes, 1 hour, 4 hours, 8 hours, and 24 hours post injection. Untreated animals were included as control and called 0 minutes. Each time point consisted of 3 animals. At the indicated time points liver, kidney, and blood was harvested from each animal. Whole blood was centrifuged and only the plasma was retained. Whole liver and kidneys were frozen and stored at −80° C. until processing. Before quantifying HS-72 in the plasma and tissue a standard curve was made using HS-72 and N-(1-methyl-1H-benzo[d]imidazol-2-yl)-1-(pyrazin-2-yl)piperidine-3-carboxamide ("HS-156"), as the internal standard. HS-72 and HS-156 were diluted in water and were further diluted 1:4 in acetonitrile. The resulting solution was then filtered through a 0.2 μm PTFE membrane (VWR, Radnor, Pa.). 15 uL of the solution was run through an Eclipse Plus C18 column (Agilent, Santa Clara, Calif.) and analyzed by an Agilent Ion Trap 6130 LC-MS (Agilent, Santa Clara, Calif.). The total ion chromatogram (TIC), extracted ion chromatogram (EIC), UV chromatogram, and mass spectra (MS) were obtained for each run. The area under the curve from the EIC for HS-72 at 364-366 and for HS-156 at 337 was determined. The EIC area ratio for HS-72 compared to HS-156 was calculated and this ratio was used to plot a standard curve based on the known concentrations of HS-72. The plasma samples were processed in the same manner as in the standard curve and analyzed by LC-MS. The resulting EIC ratios from HS-72 compared to HS-156 were then determined, which was used to calculate the concentration of HS-72 in the diluted sample. The concentration in solution of HS-72 was adjusted for the 1:4 dilution that occurs during sample preparation. The final concentration of HS-72 in plasma was calculated per mL of plasma. The liver and kidney samples were weighed and homogenized in tissue lysis buffer. The resulting homogenate was then processed in the same manner as the plasma samples. The resulting EIC ratios from HS-72 compared to HS-156 were then determined, which was used to calculate the concentration of HS-72 in the diluted sample. The concentration in solution of HS-72 was adjusted for the 1:4 dilution that occurs during sample preparation. Final concentration of HS-72 in the kidney and liver was calculated per gram of tissue using the weight of each tissue measured before sample processing.

Statistical analysis: All statistical analysis were performed using GraphPad Prisim4 (La Jolla, Calif.). Significance determined as p<0.05. Thermofluor data was analyzed using a one-way ANOVA with a Newman-Keuls posttest. All proliferation data was analyzed using a two-way ANOVA with a Bonferroni posttest. Linear regression analysis was used to compare the slope of the lines between the HS-72 treated animals and control animals.

FLECS Screen: A pEGFP-tagged Hsp70i was (plasmid 15215, Addgene, Cambridge, Mass.) used in the FLECS assay and was originally cloned according to [Zeng et al. (2004). Hsp70 dynamics in vivo: effect of heat shock and protein aggregation. Journal of cell science 117, 4991-5000]. ATP used in the assay was purchased from Sigma (St. Louis, Mo.) and a 200 mM stock was prepared with low salt buffer (150 mM NaCl, 25 mM Tris, pH 7.5, 60 mM $MgCl_2$). The γ-phosphate ATP sepharose was synthesized as previously described and stored in low salt buffer [Haystead et al. (1993). Gamma-phosphate-linked ATP-sepharose for the affinity purification of protein kinases. Rapid purification to homogeneity of skeletal muscle mitogen-activated protein kinase kinase. European journal of biochemistry/FEBS 214, 459-467]. FuGENE 6 transfection reagent (Roche, Mannheim, Germany) was used for transfection of GFP-Hsp70i into HEK 293T cells, following the manufacturer protocol. The transfection ensued for 48 hours, upon which time the cells were harvested and lysed in cell lysis buffer (150 mM NaCl, 50 mM Tris, pH 7.5, 1% Triton X-100, 1 mM EDTA, 1 mM DTT, and 1 tablet Complete Mini protease inhibitor (Roche)). Cell lysates were stored at −80° C. until further use. Upon binding the resin lysates were washed 3× with high stringency wash buffer (1 M NaCl, 25 mM Tris, pH 7.5, 60 mM MgCl2, 1 mM DTT) and 3× with low stringency wash buffer (150 mM NaCl, 25 mM Tris, pH 7.5, 60 mM MgCl2, 1 mM DTT). Next the lysates were transferred to 0.2 μm PVDF filter 96-well plate (Corning, Corning, N.Y.) sitting on top of a black flat-bottomed 96-well catch plate (Corning). The plates were spun down using an Eppendorf Centrifuge 5810 (Hamburg, Germany) at 2000 rpm for 2 min.

Caspase 3/7 Assay: The Amplite™ Fluorimetric Caspase3/7 assay kit (AAT Bioquest, Sunnyvale, Calif.) was used per the manufacturer's instructions. Briefly, a fluorometric indicator, Ac-DEVD-AMC, was used to determine caspase activity. Cleavage of AMC by caspases resulted in a fluorescent signal that can be assessed at 440-460 nm with an excitation of 340-350 nm. Cells were seeded at 60,000 cells/well in a 96 well plate and treated with compound for the indicated period of time. Diluted caspase 3/7 assay solution was added to each well and incubated at room temperature for 2 hours protected from light, upon which time fluorescence was measured on the Victor X2 plate reader (Perkin Elmer, Waltham, Mass.).

Aggregation Assay: The PC12 rat neuronal cell line, which expresses Huntingtin exon 1 containing 74 glutamine repeats is fused to GFP and under the control of a doxycycline promoter was used [Wyttenbach et al. (2001). Polyglutamine expansions cause decreased CRE-mediated transcription and early early gene expression changes prior to cell death in an inducible cell model of Huntington's disease. Human molecular genetics 10, 1829-1845]. Cells were treated with HS-72 for 18 hours prior to a doxycycline addition for 48 hours. The soluble and pellet fraction were then separated by centrifugation at 14,000 rpm for 15 minutes and both fractions were assayed for httQ-GFP by solubilizing with SDS followed by western blotting with antibodies against GFP.

Thermofluor Assay: SYPRO orange (Molecular Probes, Eugene, Oreg.) was diluted 1:1000 in 25 mM HEPES, 5 mM $MgCl_2$, 10 mM KCl (pH 7.5) and purified Hsp70i, Hsc70, Hsp70i C306, or Hsp90, was then added to a final dilution of 0.04 mg/ml. Where indicated 0.001% or 0.01% Triton X-100 (Sigma) was also added. The indicated compound or DMSO was then added at the specified concentration and each sample was added as 5 replicates to a 384 well plate (BioRad, Hercules, Calif.). A melt curve protocol (25° C. to 90° C., increasing 0.5° C. and a plate reading every 30 seconds) was run on a CFX384 Touch™ Real-Time PCR Detection System (BioRad). To determine the midpoint of the protein unfolding transition or $T_m$, GraphPad Prisim4 (La Jolla, Calif.) was used to normalize the melt curve and to calculate the first derivate of the melt curve, with the steepest point of the slope being the $T_m$.

Docking Studies: HS-72 was docked into the crystal structure of the Hsp70i NDB bound to AMP-pnp (PDB: 2E8A) using the SwissDock program [Grosdidier et al. (2011). Fast docking using the CHARMM force field with EADock DSS. Journal of computational chemistry; Grosdidier et al. (2011). SwissDock, a protein-small molecule docking web service based on EADock DSS. Nucleic acids research 39, W270-277]. The returned clusters were distributed between two binding sites. Chimera was used to visualize the putative binding sites of HS-72 on the Hsp70i NBD [Pettersen et al. (2004). UCSF Chimera—a visualization system for exploratory research and analysis. Journal of computational chemistry 25, 1605-1612].

Partial Proteolysis: Hsp70i (8 µg for SDS-PAGE analysis, 2 µg for mass spec analysis) was incubated with 1 mM ATP, 1 mM ADP, 100 uM HS72, 100 uM HS72+1 mM ATP, or 100 uM HS72+1 mM ADP for 30 min. at room temperature. Hsp70i was digested by adding 0.1 µg of trypsin (Promega, Madison, Wis.) per 2 µg of protein and was quenched by addition of 25% TFA for mass spec analysis or addition of 5×SDS loading buffer and boiling for SDS-PAGE analysis at 2 hours, or 24 hours. Gels were visualized by silver stain.

HS-72 in vivo Efficacy Studies: MMTV-neu mice, a HER2 overexpression breast cancer mouse model in which HER2 is under the transcriptional control of the mouse mammary tumor virus promoter/enhancer, were treated with the indicated doses and dosing schedule [Taneja et al., 2009]. All doses were delivered through IP injections using DMSO and their tumors were calipered once weekly. The mice were culled upon reaching tumor burden or if they expressed signs of toxicity as per MP1U standard protocol.

Results

FLECS Screening Yields Highly Selective Hsp70i Interactors. For screening of Hsp70i inhibitors by FLECS, GFP-Hsp70i was expressed in HEK293 cells, extracts prepared, incubated directly with γ-phosphate-linked ATP-Sepharose and then eluted with ATP or ADP (FIG. 1A). These studies demonstrated that the GFP-fusion protein has a fully functional nucleotide binding pocket and that binding occurs in a reversible manner. Based on the crystal structure of the Hsp70 homologue DnaK with bound ATP, showing limited solvent accessibility, recovery of the fusion protein on γ-linked ATP resin was at first surprising (FIG. 1B). This is because the γ-phosphate oxygen on the immobilized ATP is tethered to PEG, which is expected to sterically hinder Hsp70i binding. It is believed that the fusion protein is recovered through binding Hsp70 in the apo or ADP-bound form, which is subsequently driven into the ATP-bound conformation when exposed to the γ-linked ATP resin (FIG. 1C). Once bound, the protein is retained because of an inability to hydrolyze the PEG linked phosphate. The dramatic differences in elution between ATP compared to ADP shown in FIG. 1A are consistent with this hypothesis. Once bound, exposure to low µM [$Mg^{2+}$ ATP] enables the protein to turn over and be released. In contrast, mM [ADP] were required to compete the bound fusion protein from the immobilized nucleotide. These findings suggested an opportunity to use the FLECS approach to identify selective inhibitors of Hsp70i that either act competitively at the ATP binding site or allosterically to regulate nucleotide binding.

Figure 2:
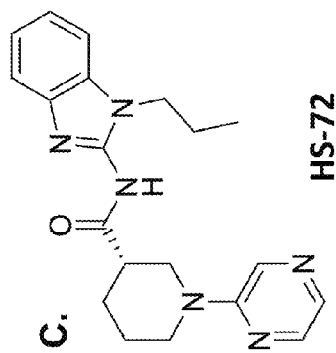
FIG. 2 shows heat maps showing summary of results of screening of Hsp70i by FLECS and the relative selectivity of hits against other purinome members. In (A) FLECS identified 197 primary hits from a collection 3379 purine like molecules (color scale dark red=strong signal to light yellow=background). In (B), the relative selectivity of all hits against Hsp70i is shown compared with other distinct members of the broader purinome screened against the same library by FLECS including ACCT, DAPK3, PIMK 1, 2, 3, Hsp90, TRAP 1, FASN, IRAK 2, PfPK9, NEK9, DENV NS5, AMPK γ and α subunit (Color scale light blue=selective, Dark red=non-selective). (C) Structure of lead molecule HS-72. See also FIGS. 8 and 9.
Figure 2:
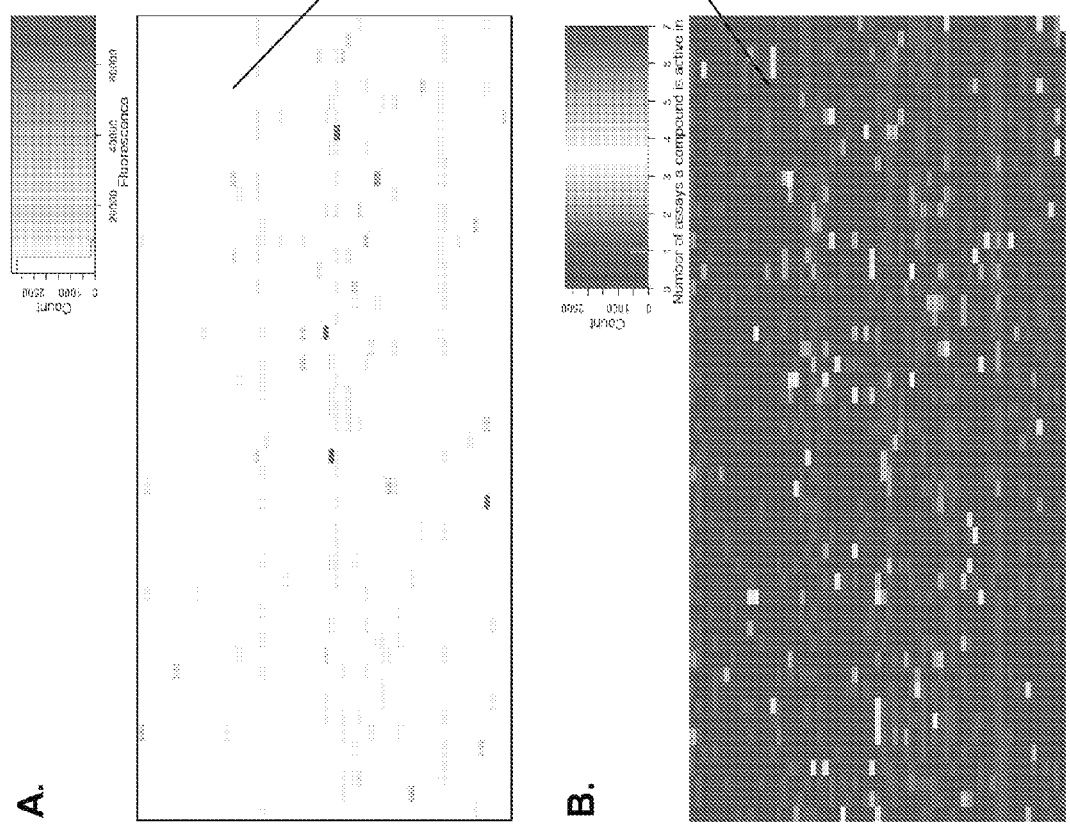
Figure 8:
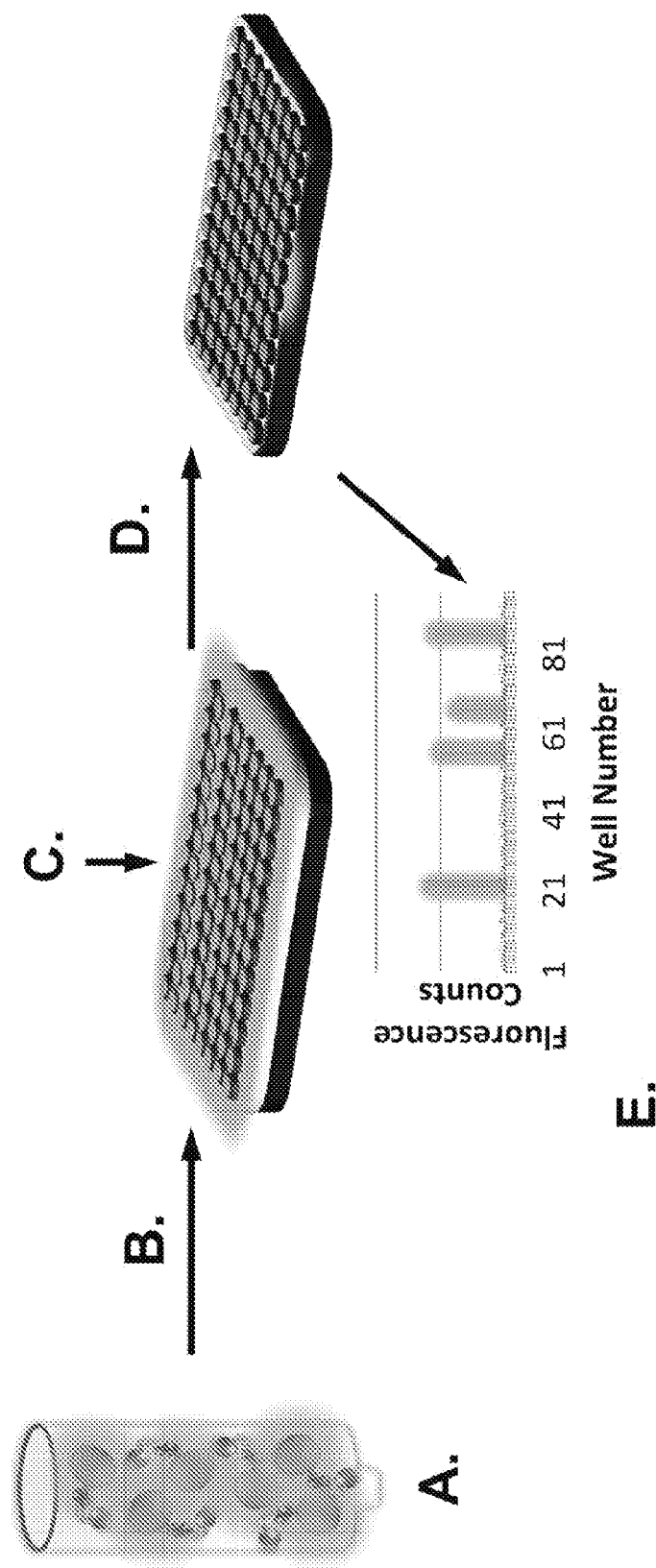
FIG. 8 shows (A) ATP resin is mixed with cell lysate containing GFP-Hsp70. (B) Washed beads are distributed into 96-well filter plates. (C) Drug candidates or ATP controls were added to each well. (D) Eluates were separated into a catch plate by centrifugation. (E) The fluorescence of each eluate was determined, and a fluorescence histogram was generated. All wells containing >2.5 fluorescence counts above background were considered to contain potential hits. Soluble ATP was used as a positive control.
Figure 9:
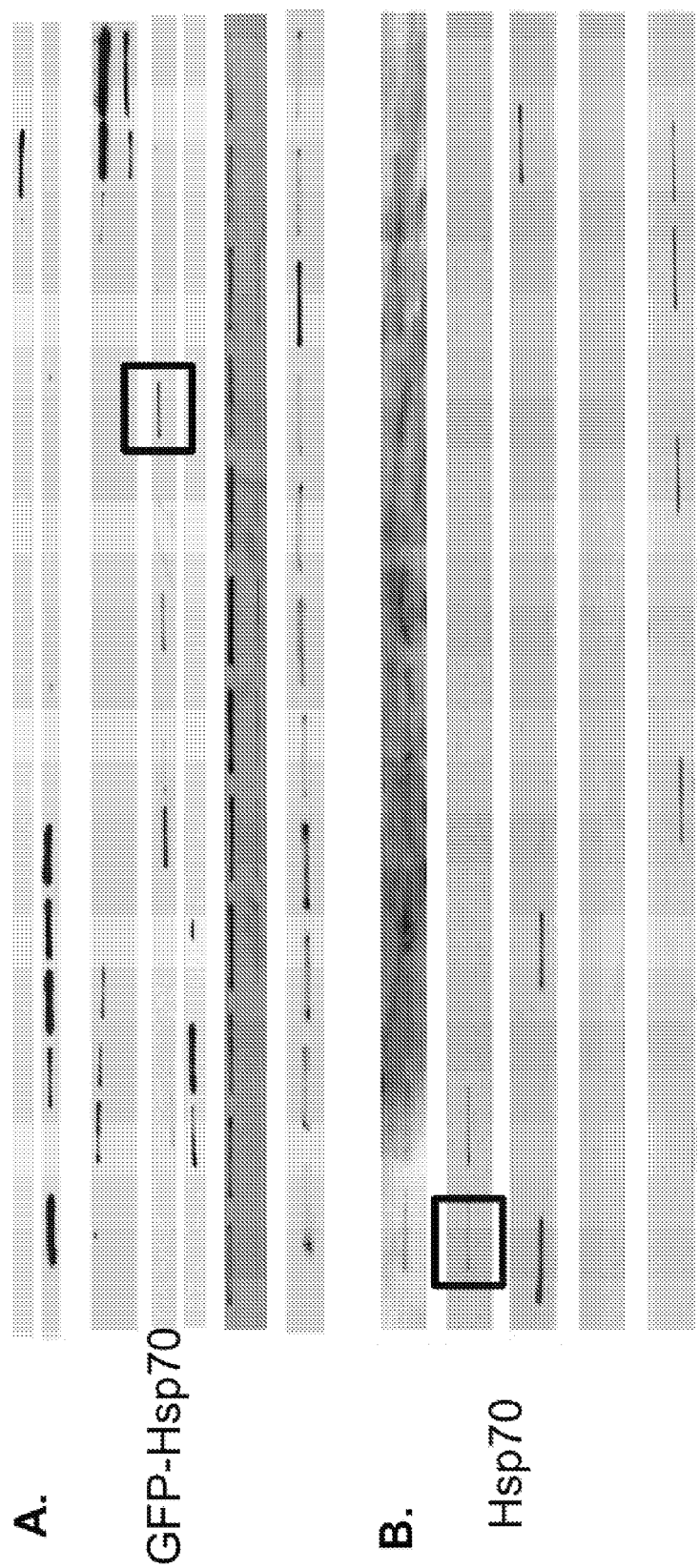
FIG. 9 shows (A) presence of Hsp70 in elutions from 197 hits based on fluorescence were analyzed by Western blotting, 60 hits confirmed. HS-72 highlighted by box. (B) Hits confirmed by Western blot eluting endogenous Hsp70 from pig bladder tissue, 22 hits confirmed. HS-72 highlighted by box. (C) Structures of 22 compounds that were identified from FLECS screen based on fluorescence, GFP-Hsp70 elution, as well as endogenous Hsp70 elution from the ATP resin. HS-72 listed as HS-207146.
Figure 9:
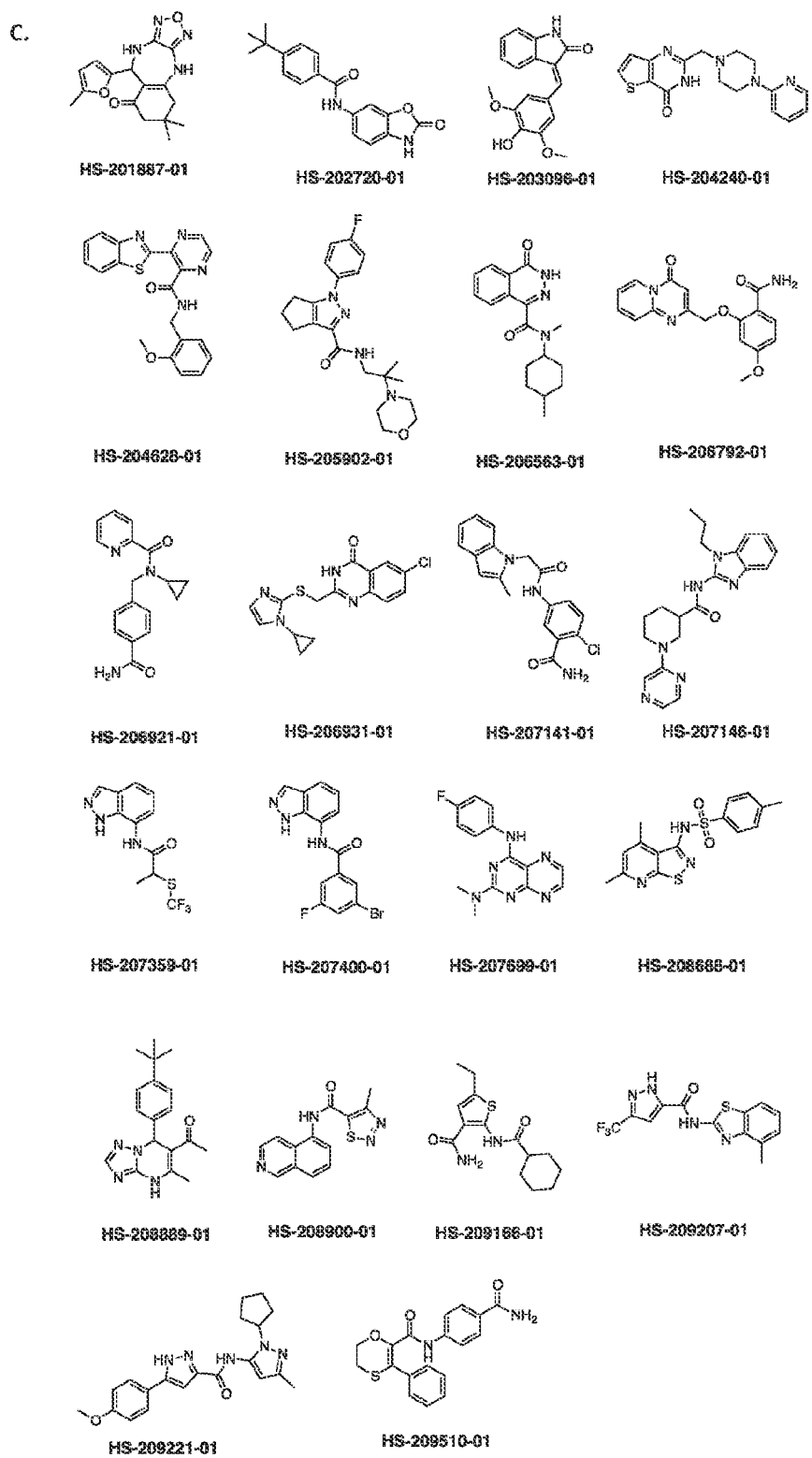
Figure 9:
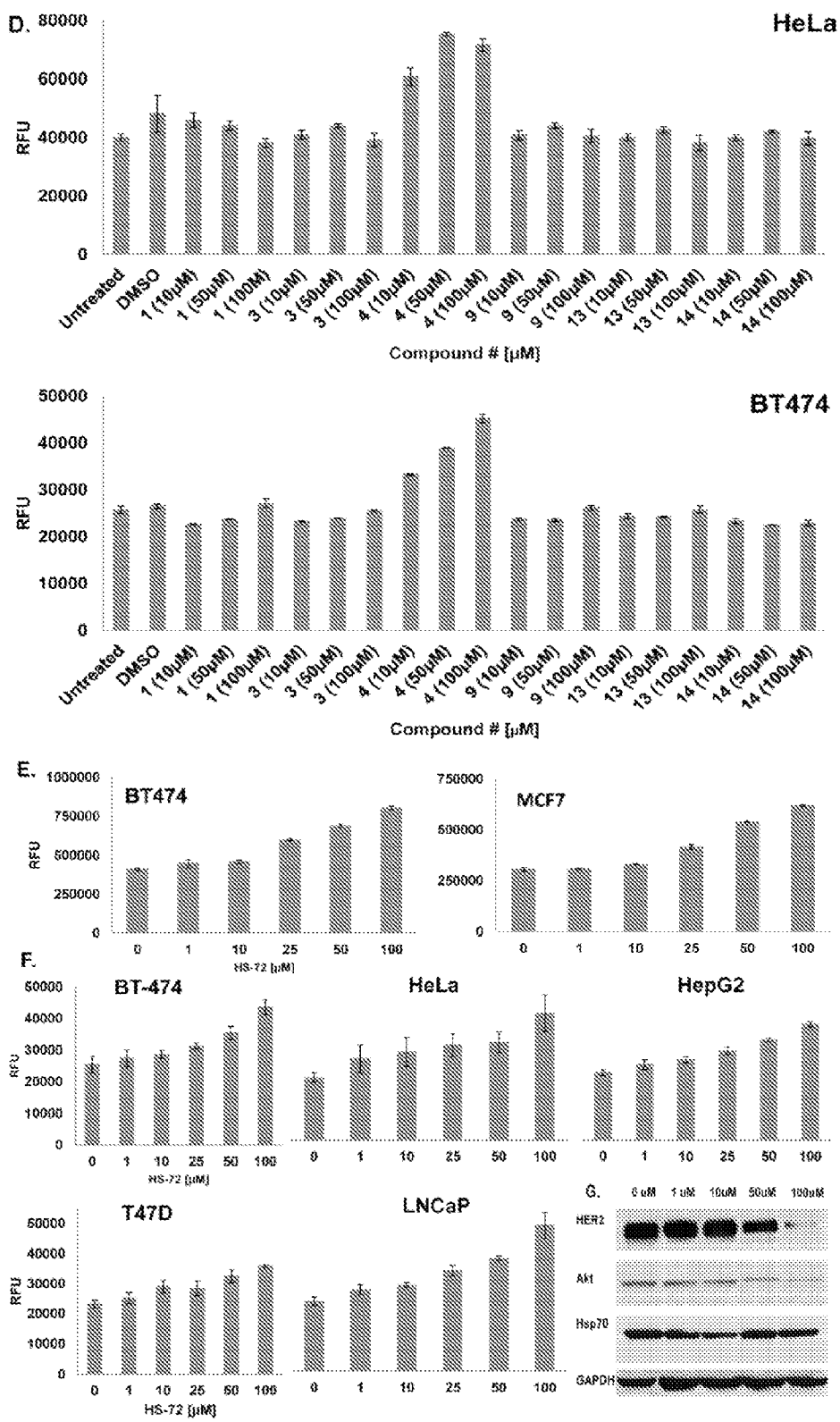

Assembly of a focused library, consisting of 3379 purine like compounds, was described previously [Carlson et al. (2013). Fluorescence Linked Enzyme Chemoproteomic Strategy for Discovery of a Potent and Selective DAPK1 and ZIPK Inhibitor. ACS chemical biology]. FIG. 8 describes FLECS, illustrating how individual compounds are screened in parallel against the ATP medium charged with GFP-Hsp70i. Briefly, GFP-Hsp70i is expressed in HEK 293T cells and crude cell lysate is then added to the ATP resin. Following several wash steps the bound GFP-Hsp70i is plated along with the compounds from the library in 96-well filter plates with ATP serving as a positive control, or with buffer to serve as a negative control. The lysates were eluted from the filter plate onto a catch plate by centrifugation and the fluorescence of the eluates was measured. Those compounds that disrupted the Hsp70i-ATP association resulted in an increased fluorescence signal over the buffer only samples. The primary screen identified 197 hits from the library, which were then sorted by their specificity towards GFP-Hsp70i over other purinome members that had also been screened against the same chemical library by FLECS (FIG. 2A-B). The compounds that were active in multiple assays were removed from consideration. Next, the presence of GFP-Hsp70i in the eluates from the 197 primary hits was determined by Western blot. This reduced the collection to 60 compounds and also eliminated auto fluorescent false positive molecules (FIG. 9A). Next the ability of the 60 compounds were tested for elution of native Hsp70 from the ATP resin using pig bladder extracts, a rich source of native Hsp70i (FIG. 9B). This reduced the final collection to 22 diverse structures (0.65% of the library), showing selectivity towards both recombinant human and native mammalian Hsp70i (FIG. 9C).

Identification of a caspase-activating cell-permeable compound that targets Hsp70i. To further narrow the number of compounds, 22 hits were tested for their ability to activate caspase-3/7 in various cancer cells, which is a hallmark of Hsp70i inhibition [Beere, H. M. (2001). Stressed to death: regulation of apoptotic signaling pathways by the heat shock proteins. Science's STKE: signal transduction knowledge environment 2001, re1]. Of the compounds tested, HS-72 ((S)—N-(1-propyl-1H-benzo[d]imidazol-2-yl)-1-(pyrazin-2-yl)piperidine-3-carboxamide) was most robust, inducing caspase activation in a dose dependent manner (FIG. 9D). Other compounds were either less potent in this assay, or were cell impermeable and were not pursued herein. Furthermore, caspase activation by HS-72 was reproducible across several cancer cell lines at 6 hours and 24 hours in a dose dependent manner (FIG. 9E-F). As a second test, the effect of HS-72 on the expression of Akt and Her2 was examined, two known client proteins of Hsp70i [Tan et al. (2011). GRP78 up-regulation is associated with androgen receptor status, Hsp70-Hsp90 client proteins and castrate-resistant prostate cancer. The Journal of pathology 223, 81-87], in BT474 breast cancer cells. FIG. 9G shows dose dependent reduction in Akt and Her2 with HS-72.

Figure 3:
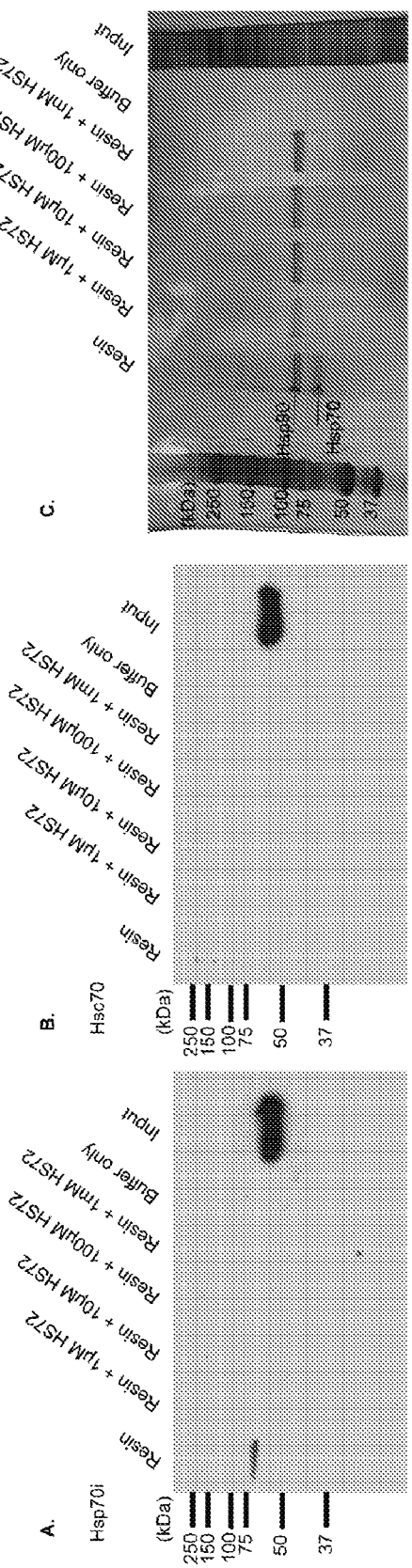
FIG. 3 shows that the HS-72 scaffold is highly selective for Hsp70i over the constitutively active Hsc70 and the wider purinome. (A-B) Cleavable HS-72 affinity resin was synthesized and mixed with HEK293T crude cell lysate±free HS-72. Following washing, sodium dithionite (25 mM) was used to cleave the ligand and the eluted proteins subjected to SDS-PAGE. (A) Western blot analysis for Hsp70i reveals Hsp70i binding to the affinity resin and this interaction is blocked by free HS-72. (B) Western blot against Hsc70 shows no binding to the resin. (C) Silver staining also demonstrates selectivity of the immobilized ligand for Hsp70i. Hsp90 recovery was non-competitive with respect to HS-72 and therefore nonspecifically bound to the media. See also FIG. 10.
Figure 10:
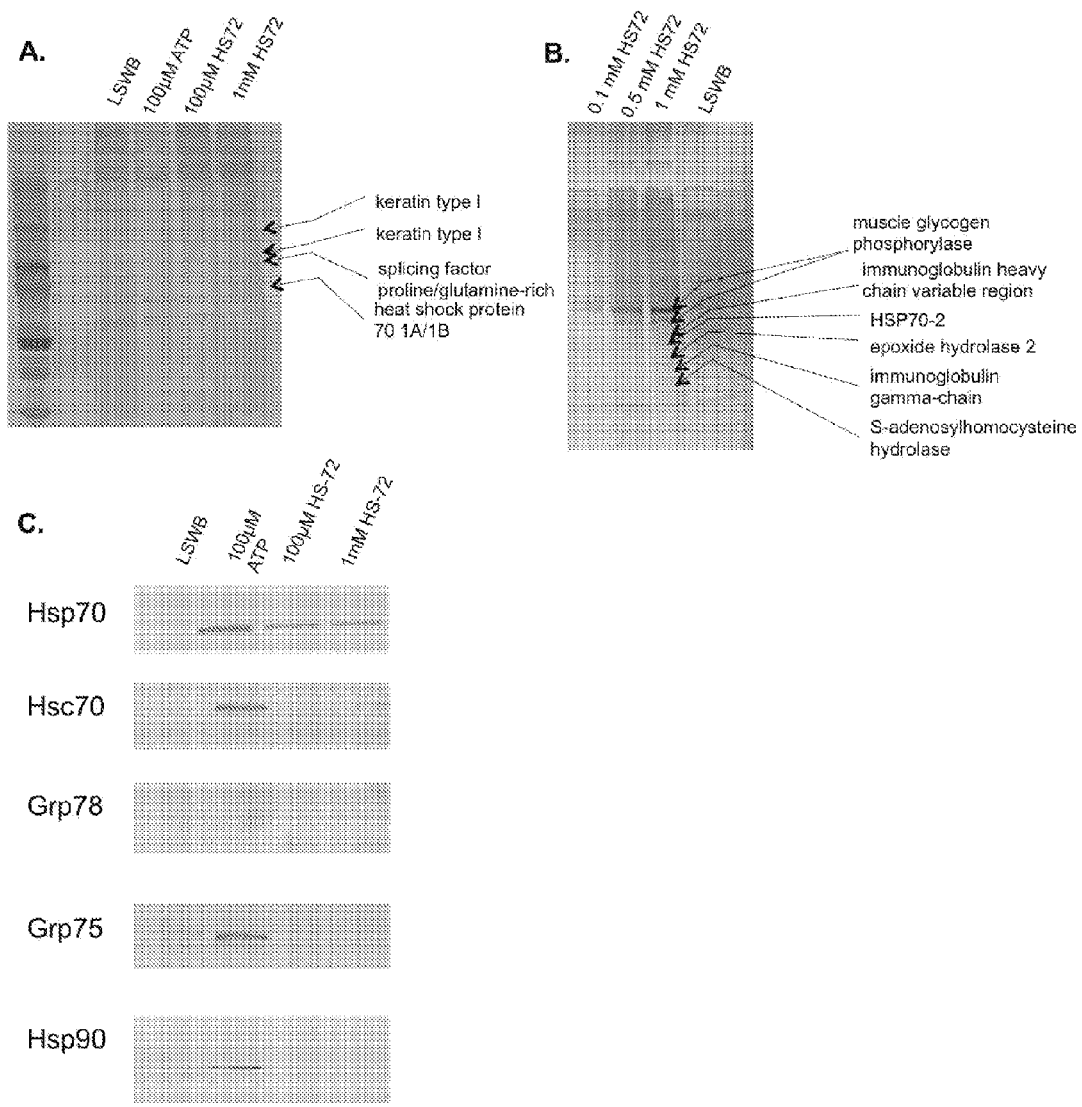
FIG. 10 shows (A) HS-72 the S enantiomer was more effective at eluting GFP-Hsp70 from the ATP resin than the R enantiomer, HS-71. (B-C) Purification of (B) Hsp70i and (C) Hsc70 shown by silver stain with the final product in the "final elution" sample. (D) The observed decrease in the $T_m$ of Hsp70 by HS-72 is not due to aggregation of the protein as shown using the thermofluor assay in the presence and absence of detergent. There is no difference in the $T_m$ of Hsp70 when comparing 100 uM HS72 alone vs. 100 uM HS72+0.001% Triton or 100 uM HS72+0.01% Triton. Furthermore, the decrease in $T_m$ in the presence of ATP is observed in the presence of 0.001% Triton and 0.01% Triton.

HS-72 specifically targets Hsp70i over other members of the Hsp70 superfamily. To test the selectivity of the HS-72 scaffold against the broader purinome, HEK 293T cell extracts or pig bladder tissue lysates were applied to the ATP resin and eluted with HS-72, as described for FLECS. The eluates were characterized by SDS-PAGE, silver stain, and MS analysis. Silver stain analysis for both HEK 293T cells and pig bladder lysates, confirmed elution of native Hsp70i and showed only a few non-specifically eluted proteins, indicating that HS-72 has a high degree of specificity within the wider purinome (FIG. 10A-B). To more thoroughly determine the specificity of HS-72 for Hsp70i, the HEK 293T eluates were also analyzed for other Hsp70 family members Hsc70, Grp78, and Grp75, as well as Hsp90 by Western blot. This showed selective elution of Hsp70i by HS-72, with ATP serving as a positive control, showing elution of Hsp70 family members and Hsp90 (FIG. 10C). Next, an affinity resin was synthesized using the HS-72 scaffold, similar to a previously described affinity resin targeting Hsp90 [Hughes et al. (2012). A highly selective Hsp90 affinity chromatography resin with a cleavable linker. Bioorganic & medicinal chemistry 20, 3298-3305]. HEK 293T cell lysate was applied to the resin and subjected to several washes. To confirm selectivity of the HS-72 affinity resin for Hsp70i, free HS-72 was incubated with lysate to inhibit Hsp70i binding to the affinity resin. The linker on the resin was cleaved using sodium dithionite and the samples were subjected to SDS-PAGE and analyzed by Western blot, silver stain, and mass spectrometry. When probing for Hsp70i by Western blot, the HS-72 affinity resin binds Hsp70i and free HS-72 is able to block this interaction (FIG. 3A). When probing for the closely related Hsp70 family member, Hsc70, the HS-72 affinity resin does not pull down Hsc70 (FIG. 3B). This indicates that the HS-72 scaffold is highly selective for the inducible Hsp70 over the constitutively active Hsc70. Furthermore, silver stain and MS analysis reveals the HS-72 affinity resin pulls down Hsp70i, and this association is blocked with free HS-72, with very few non-specific interactions (FIG. 3C). While Hsp90 is also pulled down, as shown in FIG. 3C, this is a non-specific interaction with the media itself because the association is not blocked by free HS-72. These studies identified HS-72 as the first example of a small molecule that can selectively discriminate Hsp70i from other members of the Hsp70 superfamily.

Figure 4:
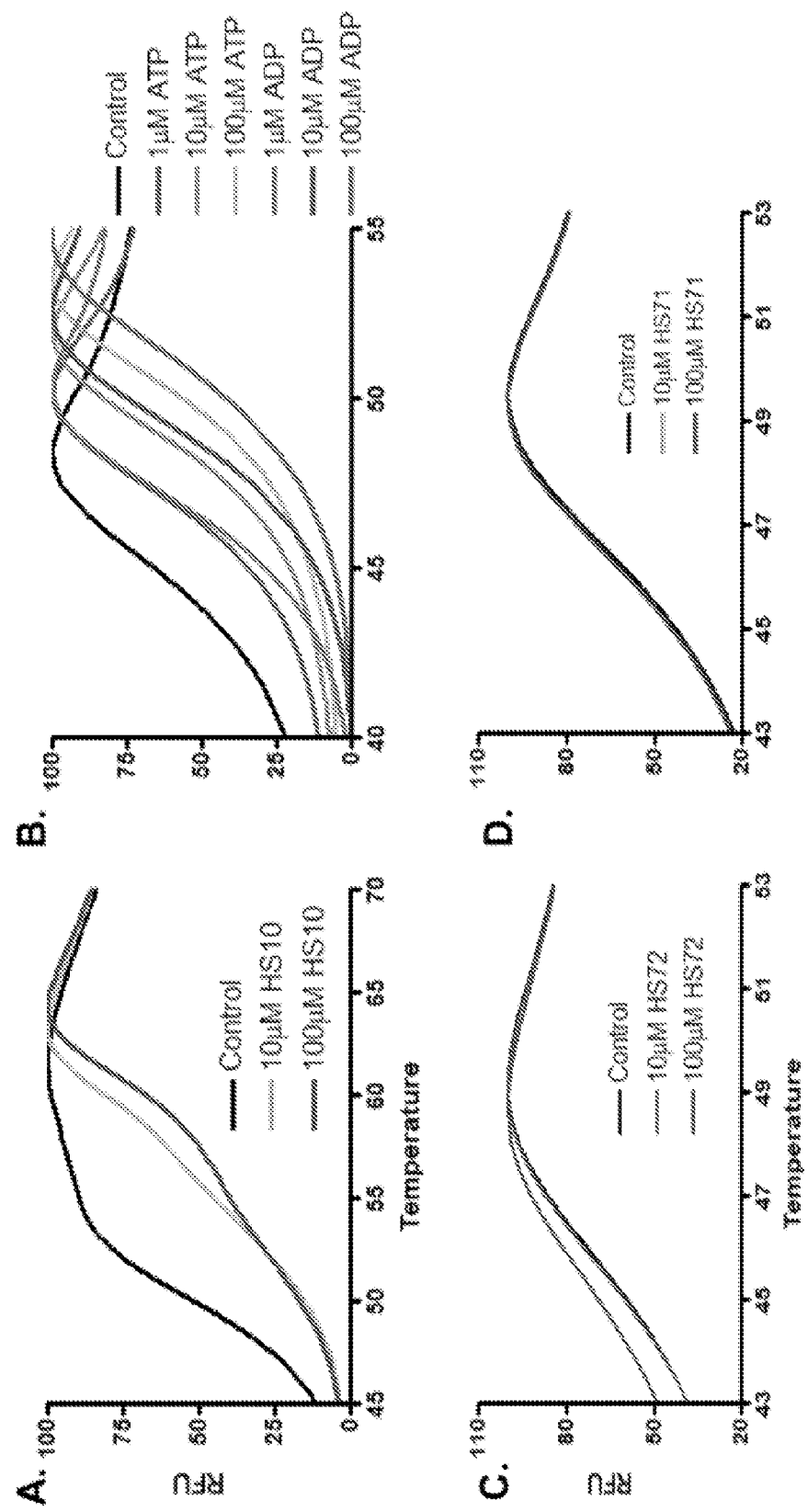
FIG. 4 shows that the thermal stability and single turnover assays reveal HS-72 is an allosteric inhibitor of Hsp70i. (A) Control study with HS-10, (Hsp90 inhibitor), increases the $T_m$ of Hsp90 by 10.5° C. (B) ATP and ADP increase the $T_m$ of Hsp70i in a dose dependent manner. (C) HS-72 decreases the $T_m$ of Hsp70i by 0.1° C. and 0.5° C. at 10 uM and 100 uM respectively, indicating an allosteric effect (p<0.001 versus control). (D) HS-71 does not change Hsp70i $T_m$. (E) ATP increases the $T_m$ of Hsp70i by 3° C., while HS-72 decreases ATP bound Hsp70i $T_m$ 0.5° C. and 1° C. at 10 uM and 100 uM respectively (p<0.001 versus ATP). (F) HS-71 does not change the $T_m$ of the ATP bound Hsp70i. (G) ADP increases the $T_m$ of Hsp70i by 2.5° C., while HS-72 does not change the $T_m$ of ADP Hsp70i. (H and I) HS-72 does not change $T_m$ of Hsc70±ATP. (J) HS-72 does not reduce Hsp70 ATPase activity in the presence or absence of co-chaperone, Hlj1. Hsp70+DMSO and Hsp70+Hlj1+DMSO indicated by dashed lines. Hsp70+HS-72 is in green, and Hsp70+Hlj1+HS-72 is in red. Hlj1+DMSO is indicated by dashed lines with squares. (K and L) HS-72 does not change $T_m$ of the Hsp70i C306D mutant.±ATP. RFU, Relative Fluorescence Units. See also FIG. 11.
Figure 4:
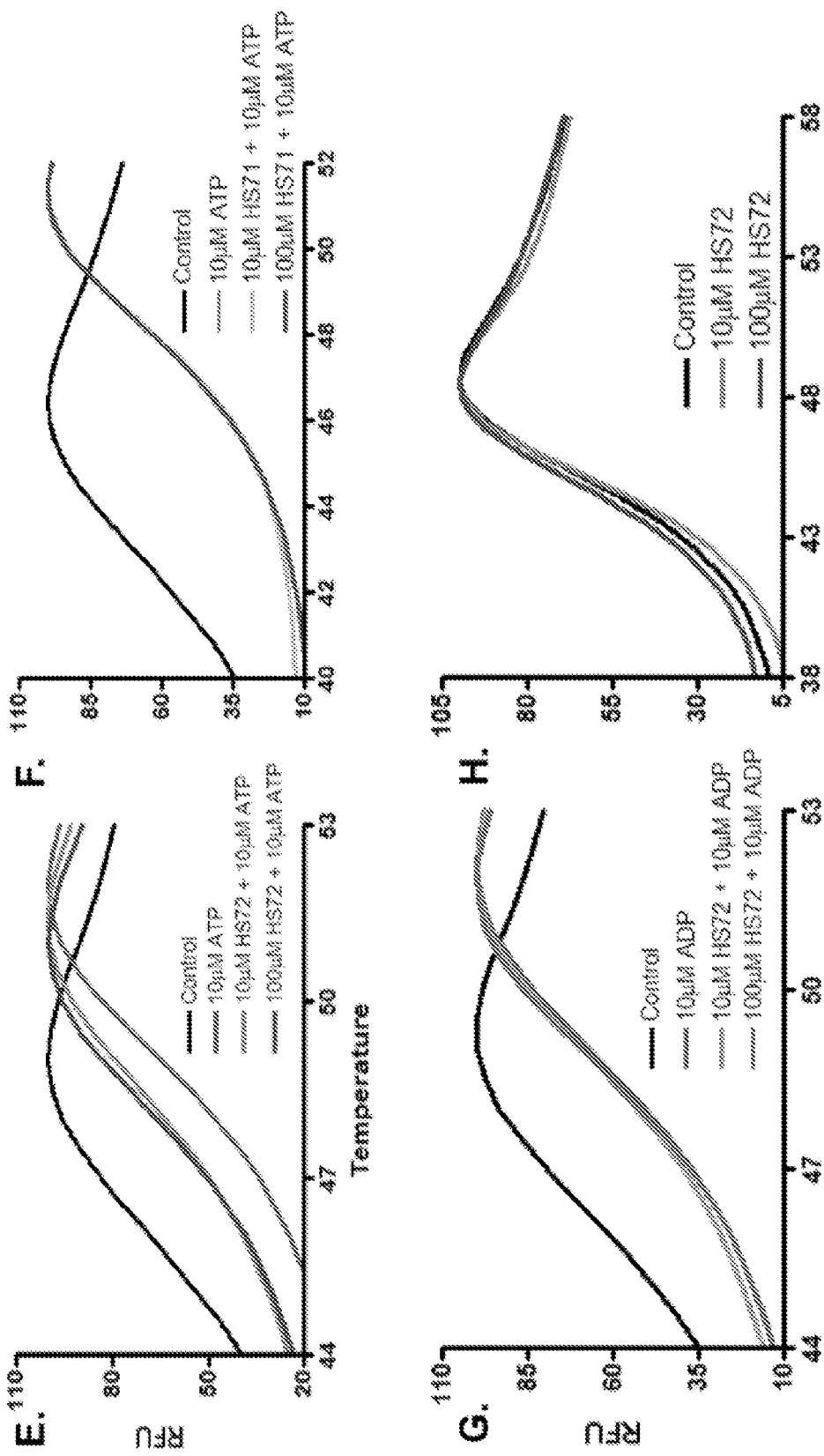
Figure 4:
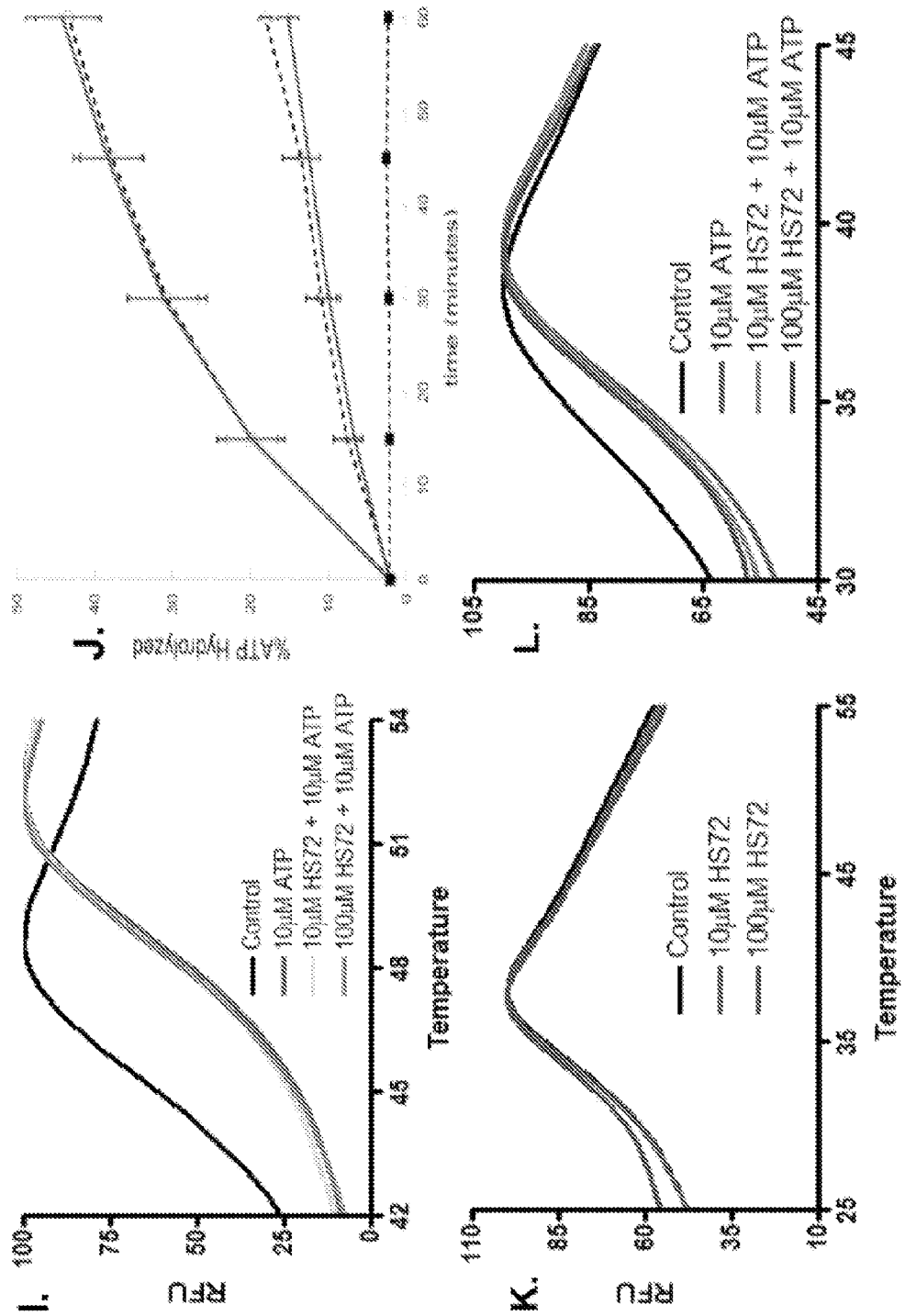
Figure 11:
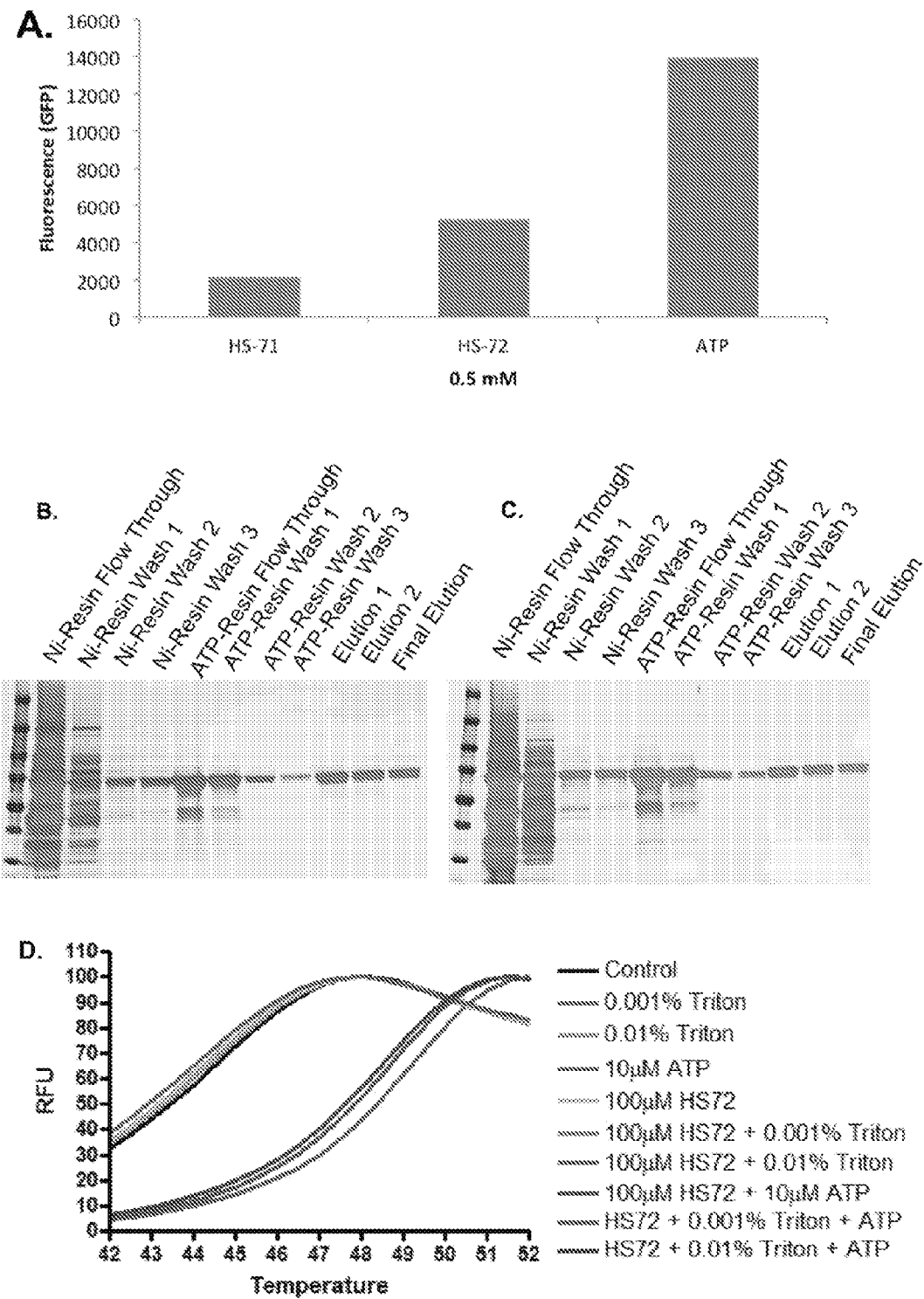
FIG. 11 shows (A) HS-72 elutes Hsp70 from HEK 293T cell lysate bound to the ATP resin, as described for FLECS, with few non-specific eluted proteins. (B) HS-72 elutes Hsp70 from pig bladder lysate bound to the ATP resin, as described for FLECS, with few non-specific eluted proteins. (C) HEK 293T cell lysate was eluted from the ATP resin as described in the FLECS assay and subjected to analysis by Western blot. All the Hsp70 family members and Hsp90 are eluted with ATP, while only inducible Hsp70 was eluted with HS-72.

HS-72 is an allosteric inhibitor of Hsp70. Because the initial isolate of HS-72 was a racemic mixture, the molecule was resynthesized in its R and S enantiomeric forms. FIG. 11A shows the S enantiomer more effectively elutes GFP-Hsp70i from ATP resin than the R enantiomer (referred to herein as HS-71). To characterize the S and R enantiomers in more detail their effects on the thermal stability of purified Hsp70i and Hsc70 were tested (FIG. 4 and FIG. 11B-C). The Thermoflour assay is used to show direct binding of a small molecule as measured by a change in melting temperature ($T_m$), [Cummings et al. (2006). Universal screening methods and applications of ThermoFluor. Journal of biomolecular screening 11, 854-863]. In general, ATP competitive inhibitors impart a large degree of thermal stability to purine binding proteins because of the number of potential contacts within the nucleotide-binding pocket [Cummings et al., 2006; Niesen et al. (2007). The use of differential scanning fluorimetry to detect ligand interactions that promote protein stability. Nature protocols 2, 2212-2221]. For example, FIG. 4A shows that 2-(((1r,4r)-4-hydroxycyclohexyl)amino)-4-(3,6,6-trimethyl-4-oxo-4,5,6,7-tetrahydro-1H-indazol-1-yl) benzamide ("HS-10"), an inhibitor of Hsp90, increases the $T_m$ of this chaperone from 50° C. to 60.5° C. [Barrott et al. (2013). Optical and radioiodinated tethered hsp90 inhibitors reveal selective internalization of ectopic hsp90 in malignant breast tumor cells. Chemistry & biology 20, 1187-1197; Hughes et al. (2012). A highly selective Hsp90 affinity chromatography resin with a cleavable linker. Bioorganic & medicinal chemistry 20, 3298-3305]. Similarly, incubation of purified Hsp70i with ATP or ADP increased the $T_m$ by 4-5° C. (FIG. 4B). However, when the study was repeated with HS-72, the $T_m$ of Hsp70i decreased in a dose dependent manner (FIG. 4C). Conversely, HS-71 had no effect on $T_m$ of Hsp70i, indicating that any effects observed with HS-72 cannot be explained by artifacts in the Thermofluor assay, such as non-specific ionic interactions or hydrophobic binding or fluorophore quenching (FIG. 4D). The effect of HS-72 on thermal stability was more apparent when the experiment was repeated in the presence of ATP, while HS-71 had no effect on $T_m$ (FIG. 4E-F). Significantly, HS-72 had no destabilizing effect on the ADP bound form (FIG. 4G). Moreover, detergents had no effect on the ability of HS-72 to destabilize Hsp70i, eliminating the possibility of non-specific protein aggregation (FIG. 11D). Furthermore, when HS-72 was tested with purified Hsc70 in the Thermofluor assay, the compound failed to trigger a significant shift in Hsc70 $T_m$ in the presence or absence of ATP (FIG. 4H-I). This further supports the selective nature of HS-72 for Hsp70i. Taken together these data suggest that although HS-72 is directly binding and selective for Hsp70i, its site(s) of interaction are unlikely to be in the ATP binding pocket. This hypothesis is consistent with data showing that HS-72 does not directly inhibit ATP hydrolysis in single turnover assays with Hsp70i (FIG. 4J). Based on the Thermofluor data the most likely mechanism of HS-72 destabilization is via allosteric binding, which reduces the protein's affinity for ATP. To explain HS-72's action in this context, it is believed that upon binding to the ATP bound state the molecule induces large conformational changes, breaking a number of internal stabilizing contacts between the NBD and C terminal domain. This mechanism of action is also reminiscent of a small molecule allosteric inhibitor that decreases the $T_m$ of RGS4 [Blazer et al. (2010). Reversible, allosteric small-molecule inhibitors of regulator of G protein signaling proteins. Molecular pharmacology 78, 524-533].

Hsp70i C306D mutation perturbs HS-72 binding. Miyata et al., using site directed mutagenesis, showed that Hsp70i C306 is a potential allosteric regulatory site within the NBD [Miyata et al. (2012). Cysteine reactivity distinguishes redox sensing by the heat-inducible and constitutive forms of heat shock protein 70. Chemistry & biology 19, 1391-1399]. Interestingly, C306 is not conserved amongst other Hsp70 family members, including Hsc70. Consistent with this earlier work, FIG. 4K-L show that the $T_m$ of the Hsp70i C306D mutant was insensitive to HS-72, either in the presence or absence of ATP. The lack of effect of HS-72 on the thermal stability of Hsp70i C306D suggests that the molecule interacts either directly with C306 or that mutation of this residue results in a conformational change that renders the HS-72 binding site inaccessible.

Figure 5:
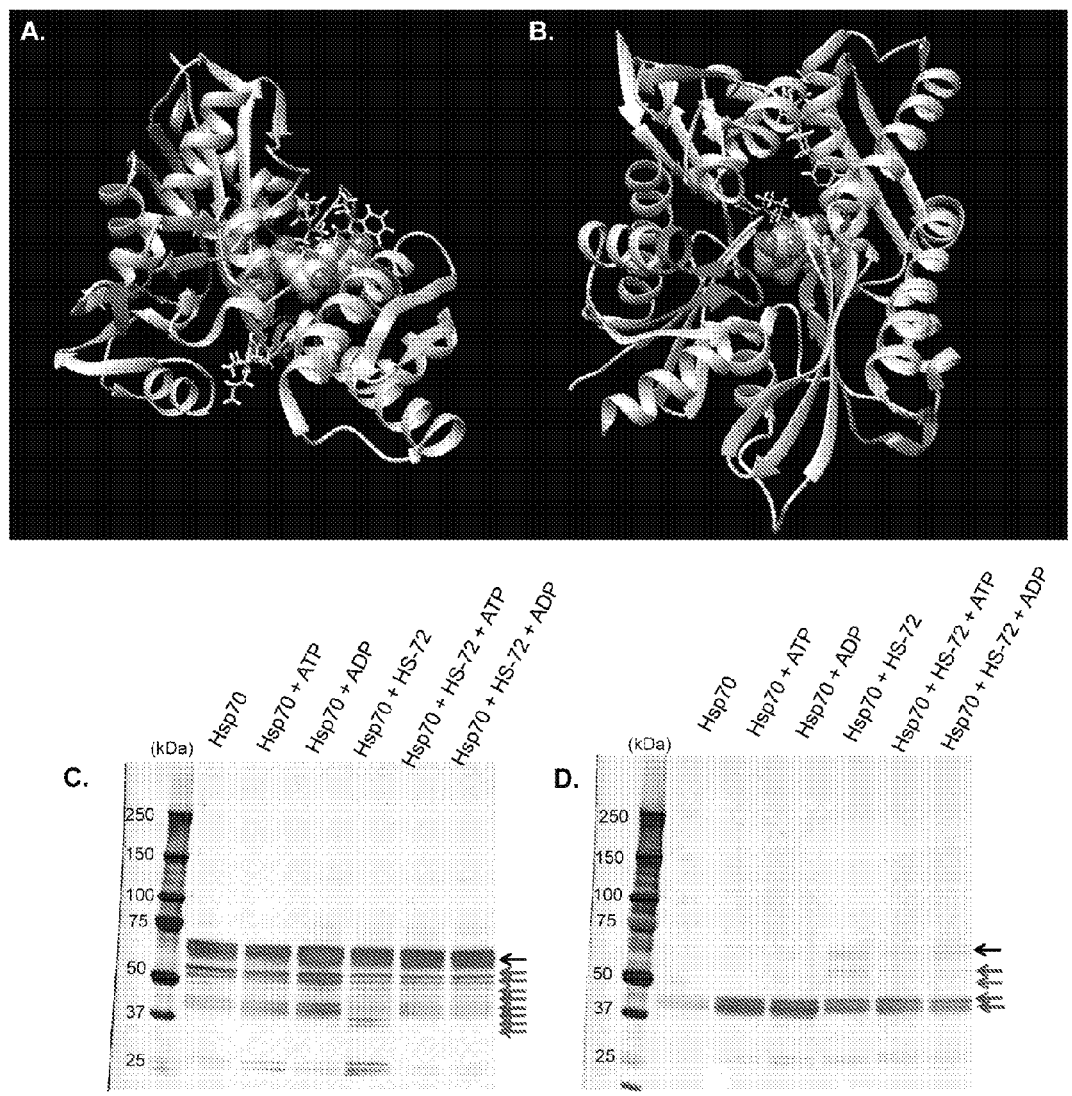
FIG. 5 shows that the molecular modeling and native protein digestion studies supports HS-72 as an allosteric inhibitor of Hsp70i. (A and B) showing two 180° views of Hsp70i NBD (PDB: 2E8A) highlighting two potential binding sites of HS-72 (sticks) form docking studies. Views also show residues identified that are protected from trypsin digestion (highlighted in red). AMP-pnp is shown as a space-filling molecule in the center. (A-B) (Visualized using Chimera). (C and D) SDS-PAGE and silver stain showing results of native digests of Hsp70i±HS-72 and ATP or ADP at 2 hours (C) and (D) 24 hours, revealing differences in digestion patterns. Full length Hsp70 (black arrow) and tryptic fragments (blue arrows). See also FIG. 12.

HS-72 allosteric interaction induces a conformational change in Hsp70i. In an attempt to gain some insight how HS-72 might be interacting with Hsp70i, a docking study was conducted of HS-72 with the crystal structure of the human NBD of Hsp70i containing AMP-pnp using the SwissDock program [Grosdidier et al., 2011]. Docking revealed 37 clusters, which were distributed between two binding sites on either side of the bound ATP analogue, further supporting an allosteric mechanism of action (FIG. 5A-B). Along with the docking partial proteolysis was used to identify potential sites of interactions. Partial proteolysis, visualized through silver stain, reveals a profound difference in the proteolytic pattern of Hsp70i in the presence of HS-72, which indicates that HS-72 induces a conformational change in Hsp70i over several time points (FIG. 5C-D and FIG. 5SA). Furthermore, MS analysis of the proteolytic pattern revealed specific residues that are protected from trypsin digestion upon inhibitor binding. Specifically, after 24 hours, peptides 141-155, 326-342, and 518-533, were all present in the samples treated with HS-72, but absent in the samples lacking HS-72 (FIG. 5D and FIG. 12B-D). It is believed that the conformational change induced by HS-72 results in sequences 141-155, 326-342, and 518-533 to be protected from digestion.

Collectively, these studies yield insight as to the potential mode of HS-72 interaction with Hsp70i. The molecular docking studies reveal two putative binding sites that are distinct from the sequences that were protected from trypsin digestion (FIG. 5A-B). Therefore it is likely that HS-72 is inducing a conformational change in Hsp70i that alters surface exposure to trypsin and therefore protects the identified sequences from trypsin digestion.

Figure 12:
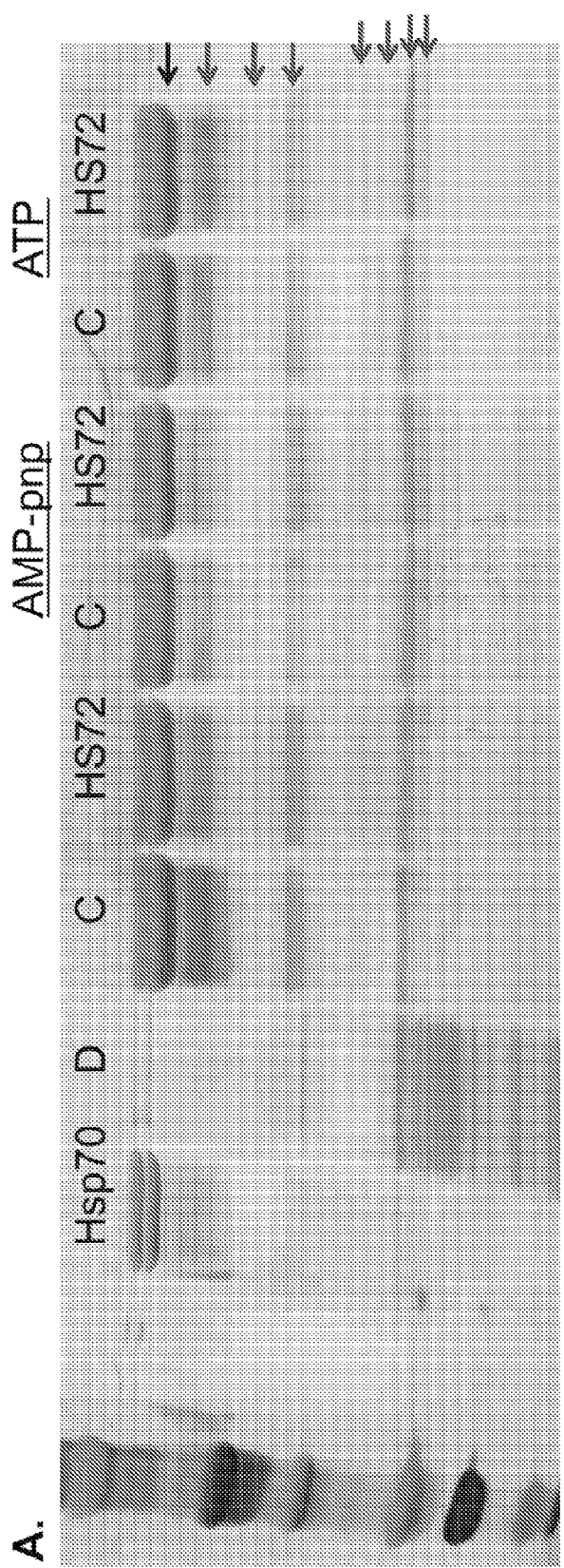
FIG. 12 shows (A-C) mass spectra of residues identified in partial proteolysis analysis, (A) residues 326-342, (B) residues 141-155, and (C) residues 518-533. Hsp70 spectra in blue, HS-72 spectra in pink and arrows highlight indicated residues showing differences in spectra. (D) Limited proteolysis reveals a differential digestion pattern in Hsp70 in the presence of HS-72 as compared to Hsp70 in the absence of HS-72. Reactions were incubated with DMSO (C) or HS-72 and the indicated nucleotide. A sample of Hsp70 was denatured (D) by heating in SDS prior to addition of Proteinase K. Undigested Hsp70 (Hsp70) was included for comparison. Full length Hsp70 indicated with black arrow and fragments resulting from proteolysis indicated with blue arrows. (E-H) HS-72 does not bind Hsp70 in the same site as VER-15508 (VER) or pifithrin-μ (PES). HS-72 in combination with VER shows no synergistic or additive interactions between the molecules when tested using thermofluor in the absence (E) or presence (F) of ATP. HS-72 in combination with PES shows no synergistic or additive interactions between the molecules when tested using thermofluor in the absence (G) or presence (H) of ATP.
Figure 12:
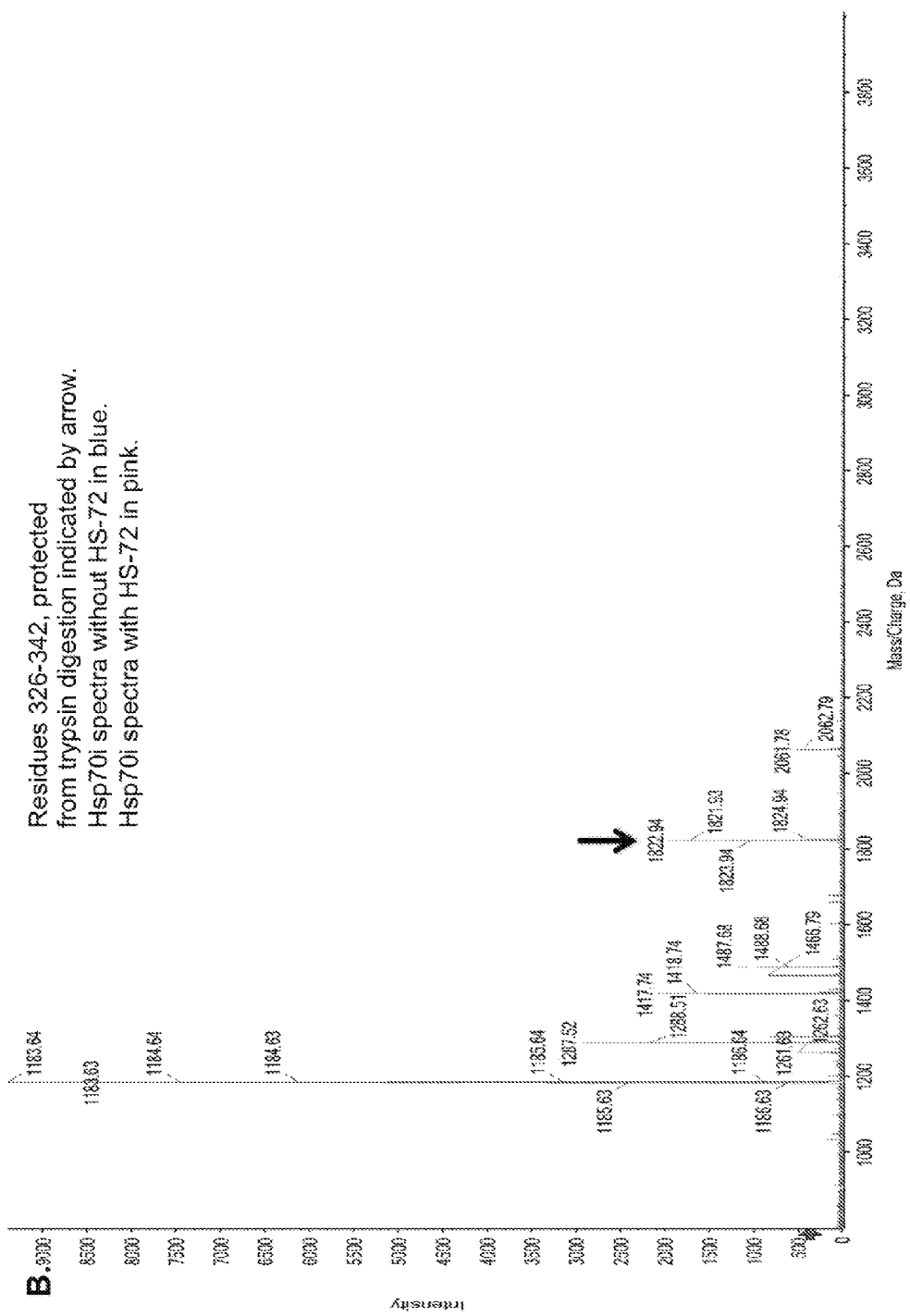
Figure 12:
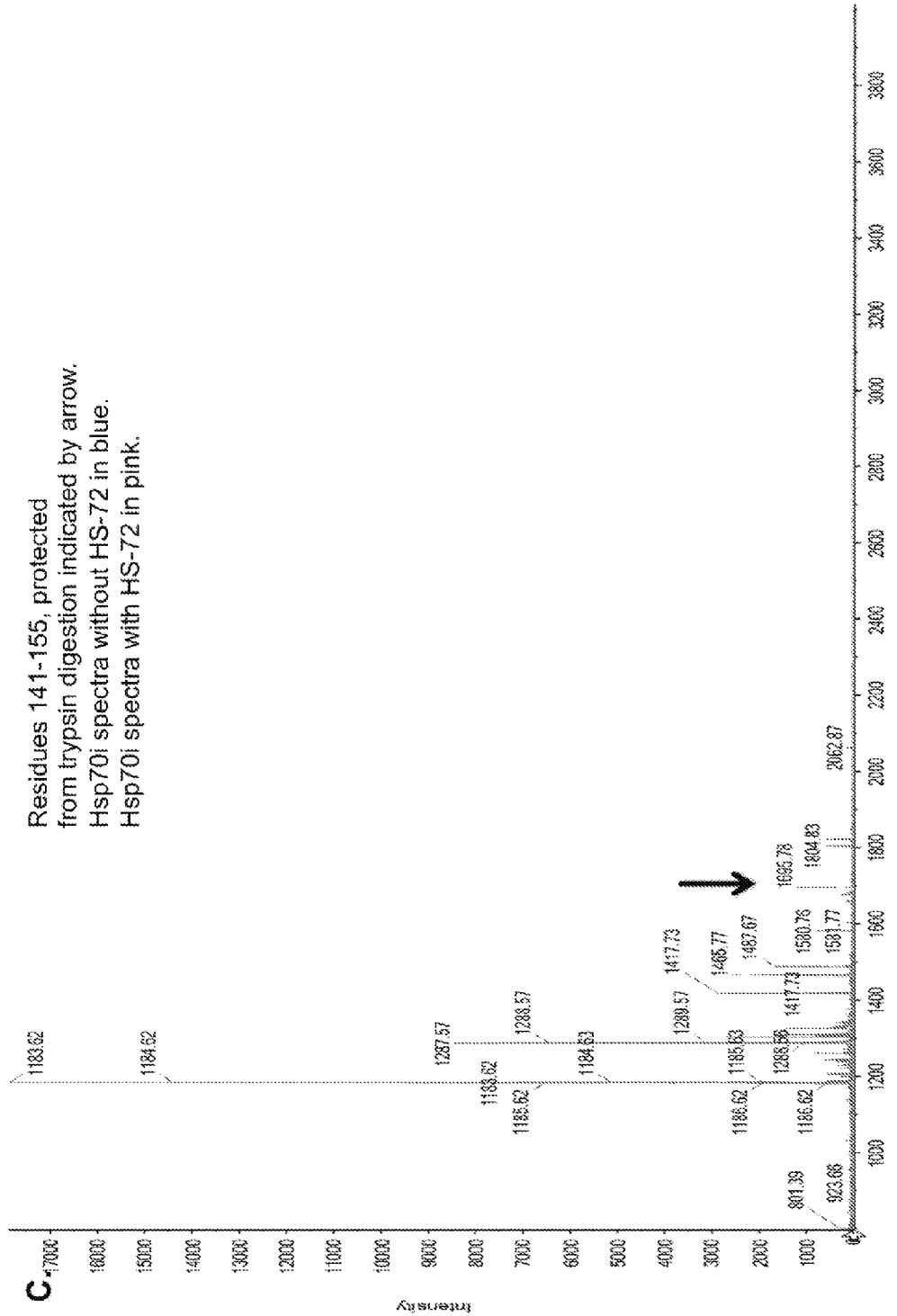
Figure 12:
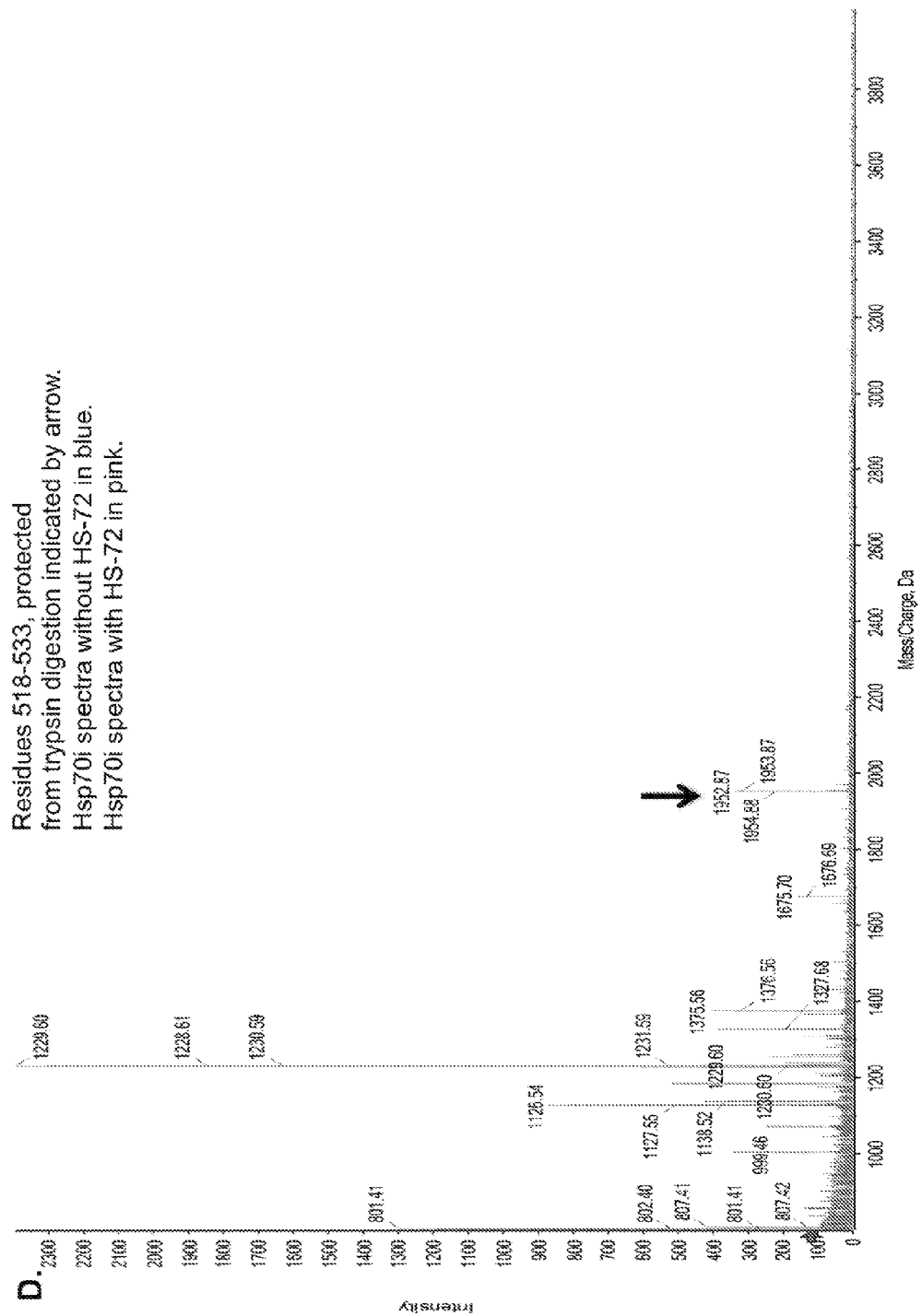
Figure 12:
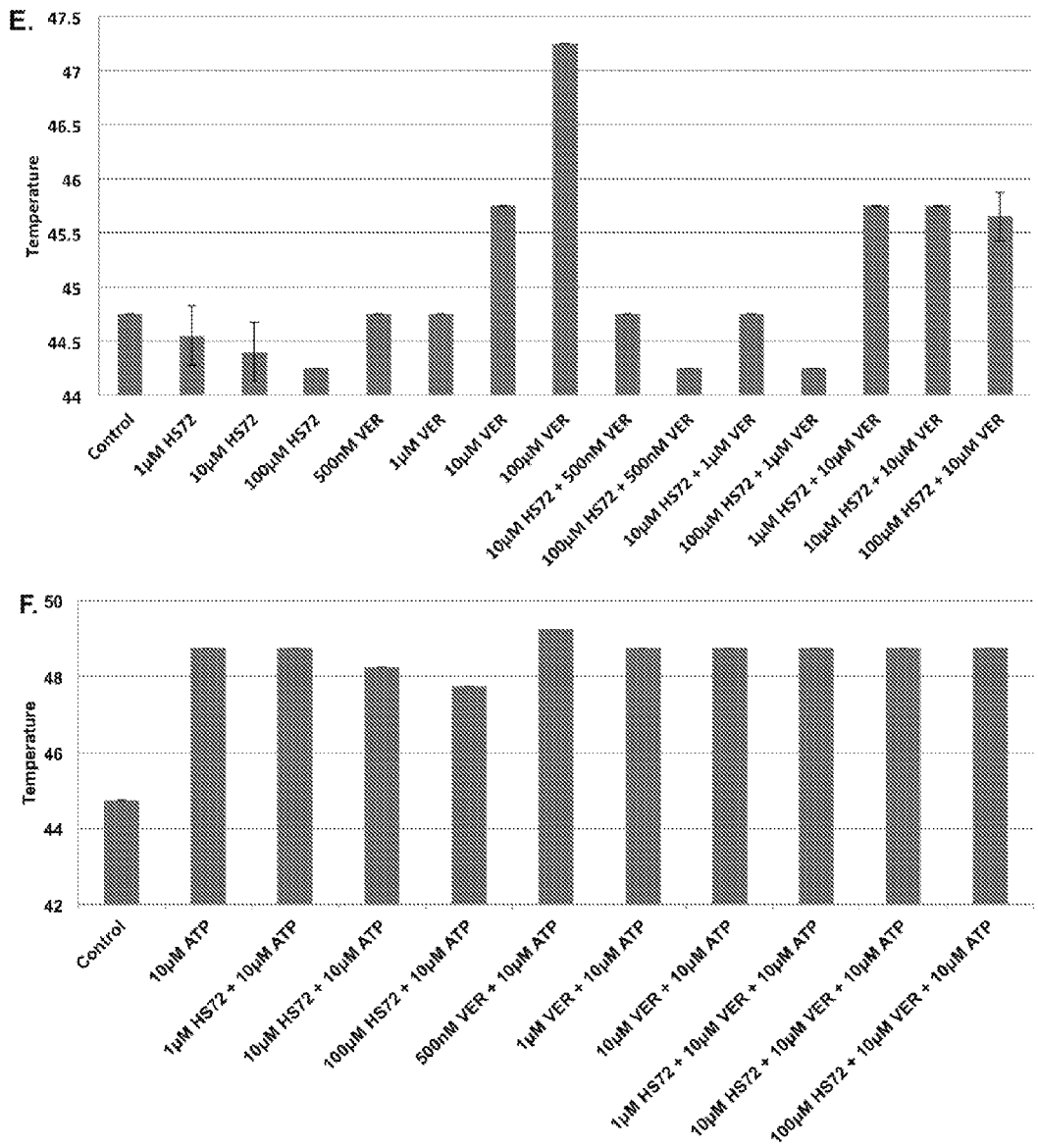
Figure 12:
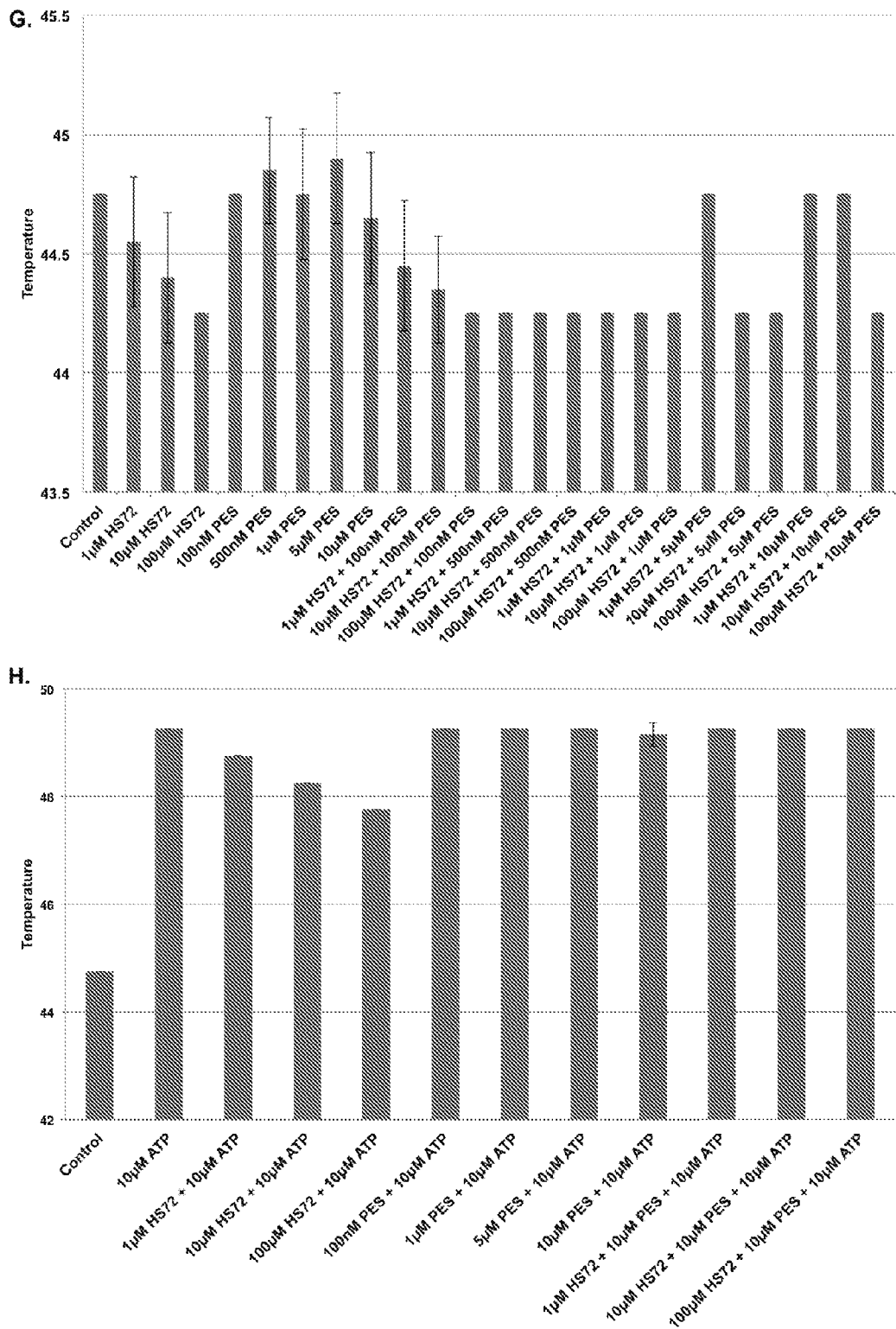

To further investigate HS-72 sites of interaction, HS-72 was tested in combination with VER-15508 (VER) or pifithrin-μ (PES) by Thermofluor. There was an increase in Hsp70i $T_m$ with VER, consistent with previous work by Massey et al. showing binding of this compound in the active site of the NBD [Massey et al. (2010). A novel, small molecule inhibitor of Hsc70/Hsp70 potentiates Hsp90 inhibitor induced apoptosis in HCT116 colon carcinoma cells. Cancer chemotherapy and pharmacology 66, 535-545]. When testing HS-72 and VER in combination there was no observed synergistic or additive effect on Hsp70i $T_m$ in the absence or presence of ATP, indicating that these molecules do not target Hsp70i at the same sites (FIG. 12E-F). This further supports an allosteric binding site of HS-72, since VER is known to bind the active site in the NBD. When testing PES alone there was no dose dependent effect on Hsp70i $T_m$ (FIG. 12G). Furthermore there was no synergistic or additive effect when testing HS-72 and PES in combination, indicating different binding sites on Hsp70i (FIG. 12G-H). This indicates that HS-72 is not targeting the Hsp70i SBD, the primary site of PES binding [Leu et al. (2009). A small molecule inhibitor of inducible heat shock protein 70. Molecular cell 36, 15-27].

Figure 6:
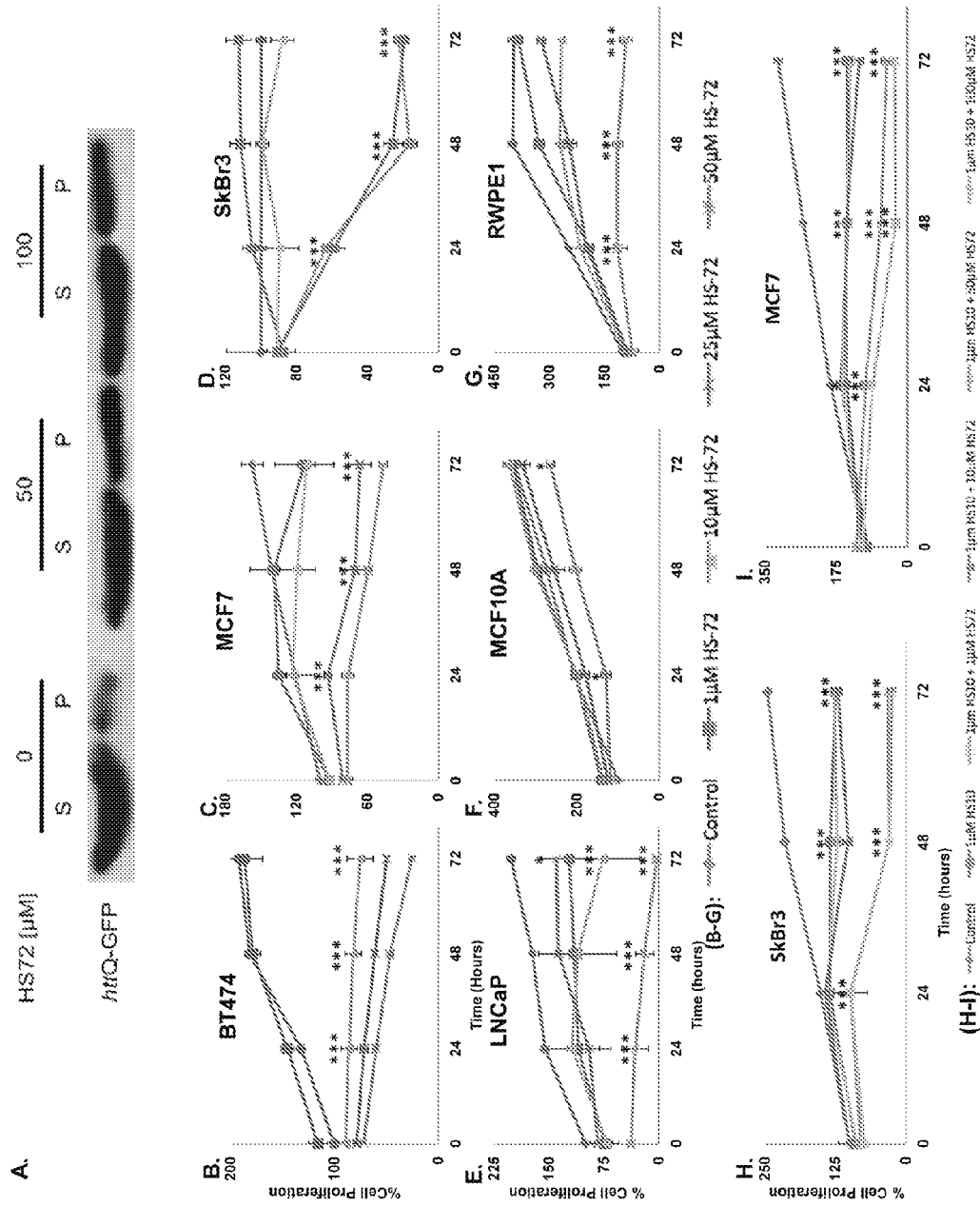
FIG. 6 shows that HS-72 inhibits Hsp70i activity in a Huntington's cell model and across multiple tumorigenic cell lines. (A) HS-72 induces protein aggregation in a cell culture model of Huntington's disease, as shown by an increase in httQ-GFP protein associated with the insoluble, pellet (P), fraction compared to the soluble (S) fraction. (B-G) HS-72 inhibits proliferation of (B) BT474, (C) MCF7, (D) SkBr3 breast cancer cell lines and (E) LnCaP prostate cancer cell lines. In contrast, non tumorigenic (F) MCF10A and (G) RWPE1 cells are insensitive to HS-72. (H and I) HS72 and the Hsp90 inhibitor HS10 show synergism in inhibiting cancer cell proliferation in (H) SkBr3 and (I) MCF7 cells. (*, p<0.05. ***, p<0.001). See also FIG. 13.
Figure 13:
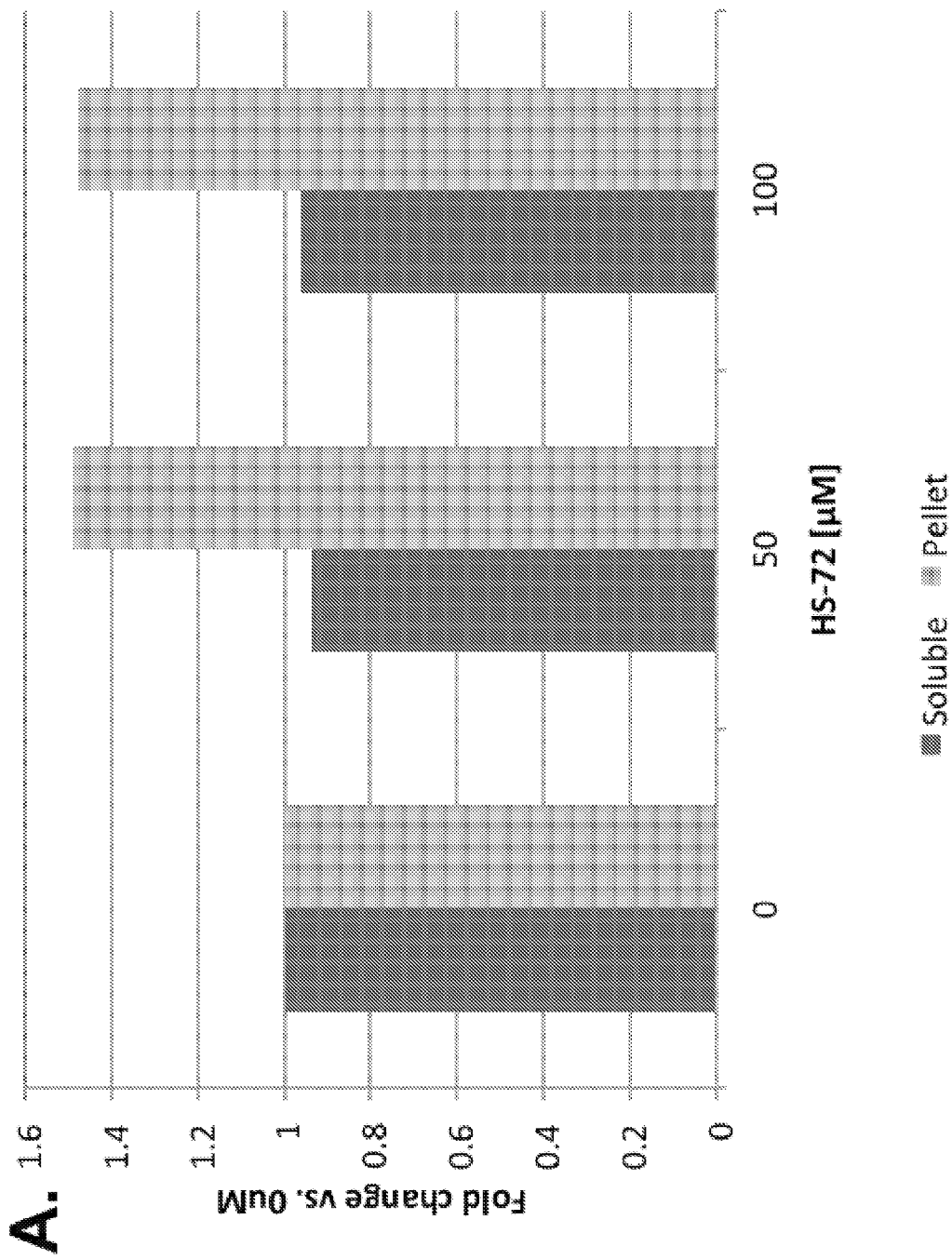
FIG. 13 shows (A) HS-72 induces the formation of HttQ-GFP aggregates in a PC12 cell culture model of Huntington's disease. Quantification of bands from western blot shown in FIG. 6A, illustrating a 50% increase of HttQ-GFP in the insoluble fraction in the presence of HS-72. (B-C) HS-71 minimally inhibits cell proliferation and has no effect on cell proliferation at 24 hours. (B) In SkBr3 cells there is an inhibition in proliferation at 48 and 72 hours at 25 uM and 50 uM. (C) In MCF7 cells there is inhibition at 48 hours at 25 uM and 50 uM, while at 72 hours significant inhibition is proliferation is observed in 50 uM alone. (*, p<0.05. ***, p<0.001). (D) Combination treatment with HS72 and HS10 induces degradation of Her2 and Akt more efficiently than either HS72 or HS10 alone in MCF7 and BT474 cells.
Figure 13:
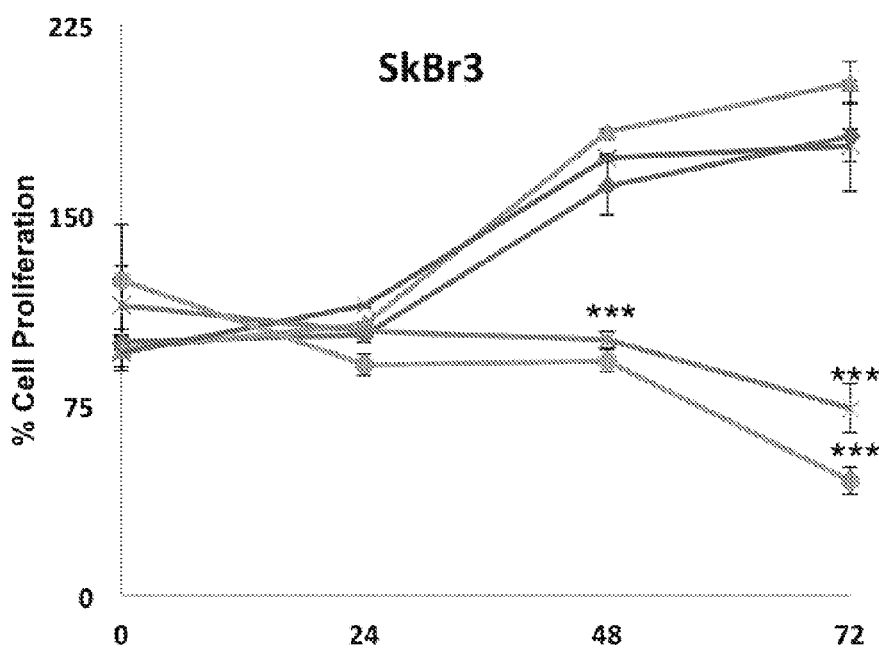
Figure 13:
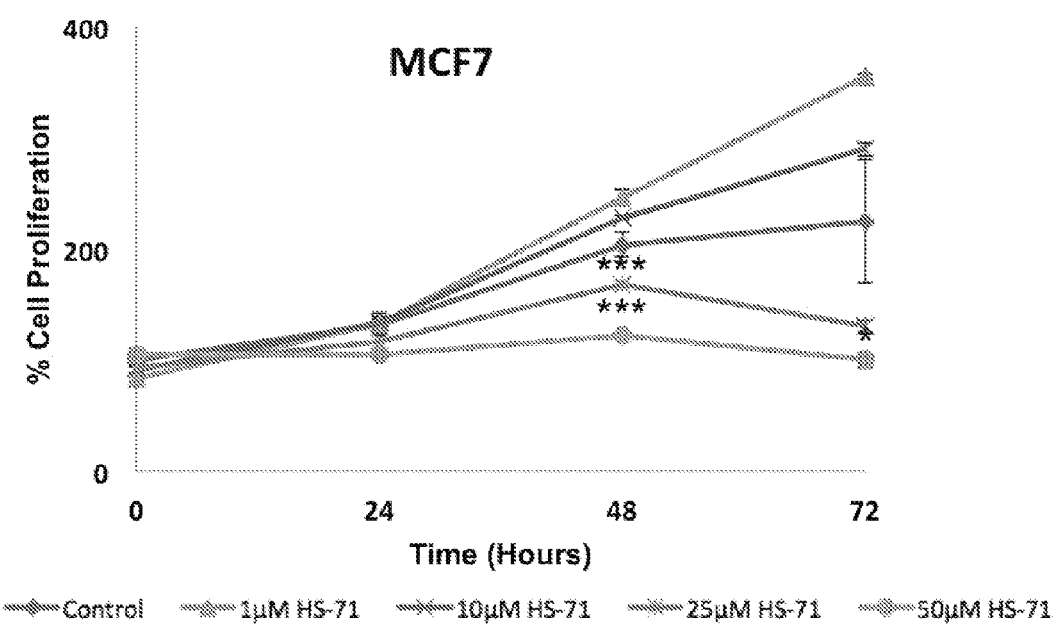
Figure 13:
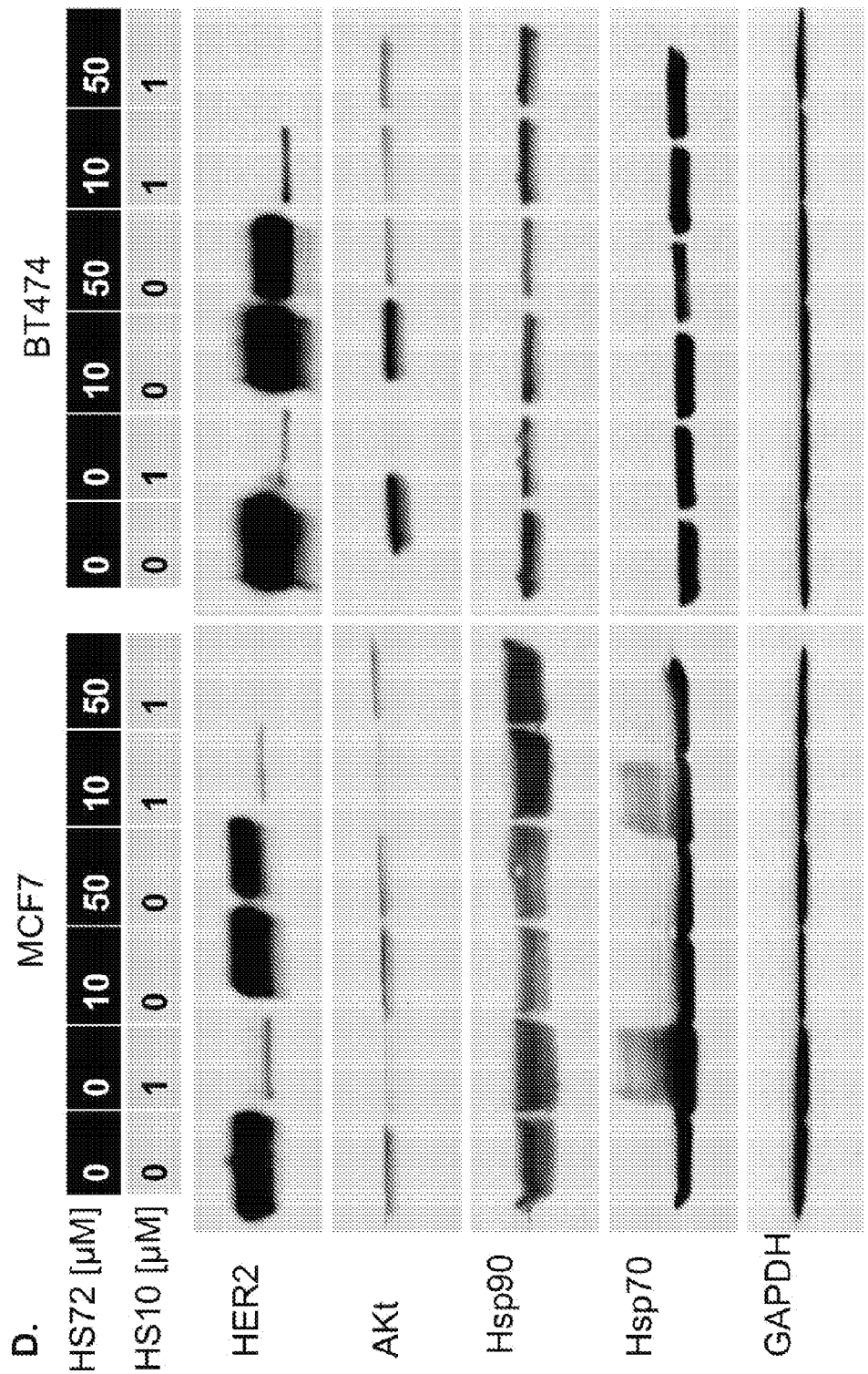

HS-72 induces cellular protein aggregation. A hallmark of Hsp70i inhibition in cells is induction of protein aggregation, which was assayed using a cell culture model of Huntington's disease. In this model, the PC12 rat neuronal cell line contains 74-glutamine repeats from exon 1 of human Huntington, fused to GFP (httQ74-GFP) [Wyttenbach et al., 2001]. The httQ74-GFP is expressed stably and is inducible through a doxycycline-regulated promoter. An induction in protein aggregates was found in the presence of HS-72 compared with untreated controls, shown by an increase in the insoluble associated pellet fraction (FIG. 6A). Quantification of these bands shows a 50% increase in the insoluble associated pellet fraction in the HS-72 treated samples compared to untreated controls (FIG. 13A).

HS-72 inhibits cancer cell proliferation. Upregulation of Hsp70i has been implicated in tumorigenicity in breast and prostate cancers [Goloudina et al. (2012); Shu et al. (2008)]. To determine if HS-72 discriminates between various cell lines proliferation assays were performed. FIG. 6B-G shows that the inhibitor has potent anti-proliferative activity against the tumorigenic breast and prostate lines while the non-tumorigenic lines continued to proliferate in the presence of HS-72. There was a significant inhibition (p<0.001) of proliferation in all tumorigenic cell lines tested (FIG. 6B-E). In contrast, the non-tumorigenic MCF10A cells continue to grow at all concentrations, while the RWPE1 cells were only inhibited at the highest concentration tested (FIG. 6F-G). HS-71 treatment results in a less potent effect on proliferation compared to HS-72, consistent with biochemical studies (FIG. 13B-C).

To test if HS-72 acts synergistically with Hsp90 inhibitors, the effect of the Hsp90 inhibitor HS-10 in combination with HS-72 was evaluated on the degradation of Her2 and Akt, which are classified as substrates or clients of Hsp70i and Hsp90, respectively [She et al. (2008). Breast tumor cells with PI3K mutation or HER2 amplification are selectively addicted to Akt signaling. PloS one 3, e3065; Tan et al. (2011)]. In the presence of HS-72, there is degradation of Her2 and Akt that is consistent with previous results (FIG. 9G). HS-10 alone also induced degradation of Her2 and Akt, as well as increased Hsp70 protein levels as expected, due to the negative regulatory role that Hsp90 has on Heat Shock Transcription Factor 1. In combination, the levels of Her2 were completely abolished and there was significant Akt degradation (FIG. 13D). Next the effect of inhibitor combination on SkBr3 and MCF7 cell proliferation was determined. Increasing amounts of HS-72 in addition to the HS-10 treatment resulted in an additive effect, potently inhibiting the proliferation of both cell lines more so than HS-72 or HS-10 alone (FIG. 6H-I). These results indicate that Hsp90 and Hsp70i inhibitor combinations are likely to have great therapeutic utility in the clinic [Guo et al. (2005). Abrogation of heat shock protein 70 induction as a strategy to increase antileukemia activity of heat shock protein 90 inhibitor 17-allylamino-demethoxy geldanamycin. Cancer research 65, 10536-10544; Powers et al. (2008). Dual targeting of HSC70 and HSP72 inhibits HSP90 function and induces tumor-specific apoptosis. Cancer cell 14, 250-262; Powers et al. (2009). Death by chaperone: HSP90, HSP70 or both? Cell Cycle 8, 518-526)].

Figure 7:
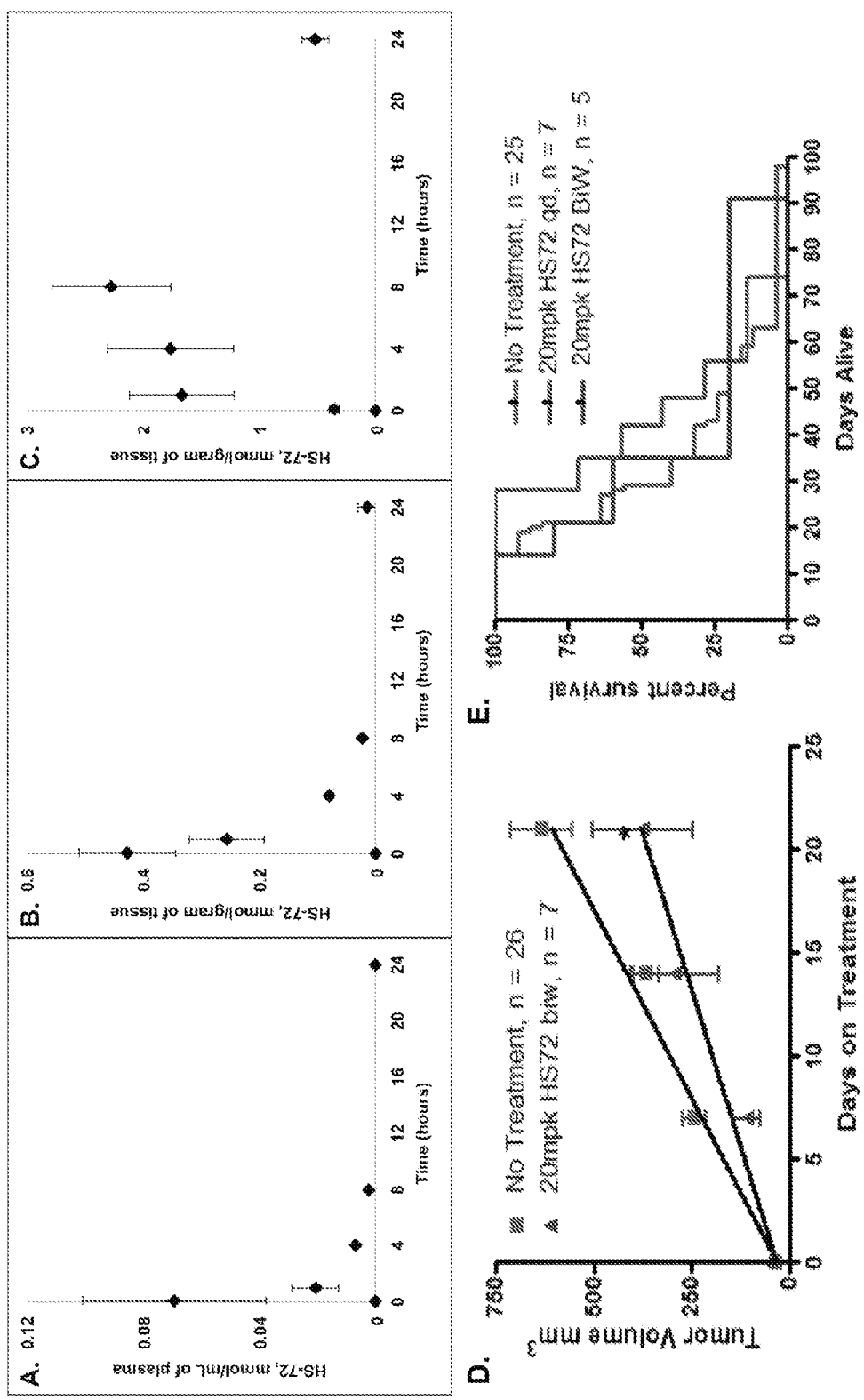
FIG. 7 shows pharmacokinetic, distribution and efficacy studies with HS-72 in healthy mice and MMTV-neu mice. (A-C) LC-MS analysis of plasma, kidney and liver following I.P. injection, 20 mg/Kg (mpk), at the indicated time points over 24 hours show HS-72 has high degree of bioavailability in health mice. In (D) HS-72 promotes reduction in tumor volume in MMTV-neu mice treated I.P. with HS72 BiW (biweekly) at 20 mpk (n=7), compared to animals receiving no treatment (n=26) with a significant decrease in tumor volume (p<0.05) at 21 days. Linear regression analysis comparing the slopes of the HS-72 tumor volume vs. no treatment tumor volume is trending towards significance (p=0.08). (E) The median survival of animals treated I.P. with HS-72 20 mpk BiW or HS-72 20 mpk qd increased by 6 days and 13 days, respectively, than animals receiving no treatment. One set of control animals was used for multiple treatments, yielding more control animals than treated animals. See also FIG. 14.
Figure 14:
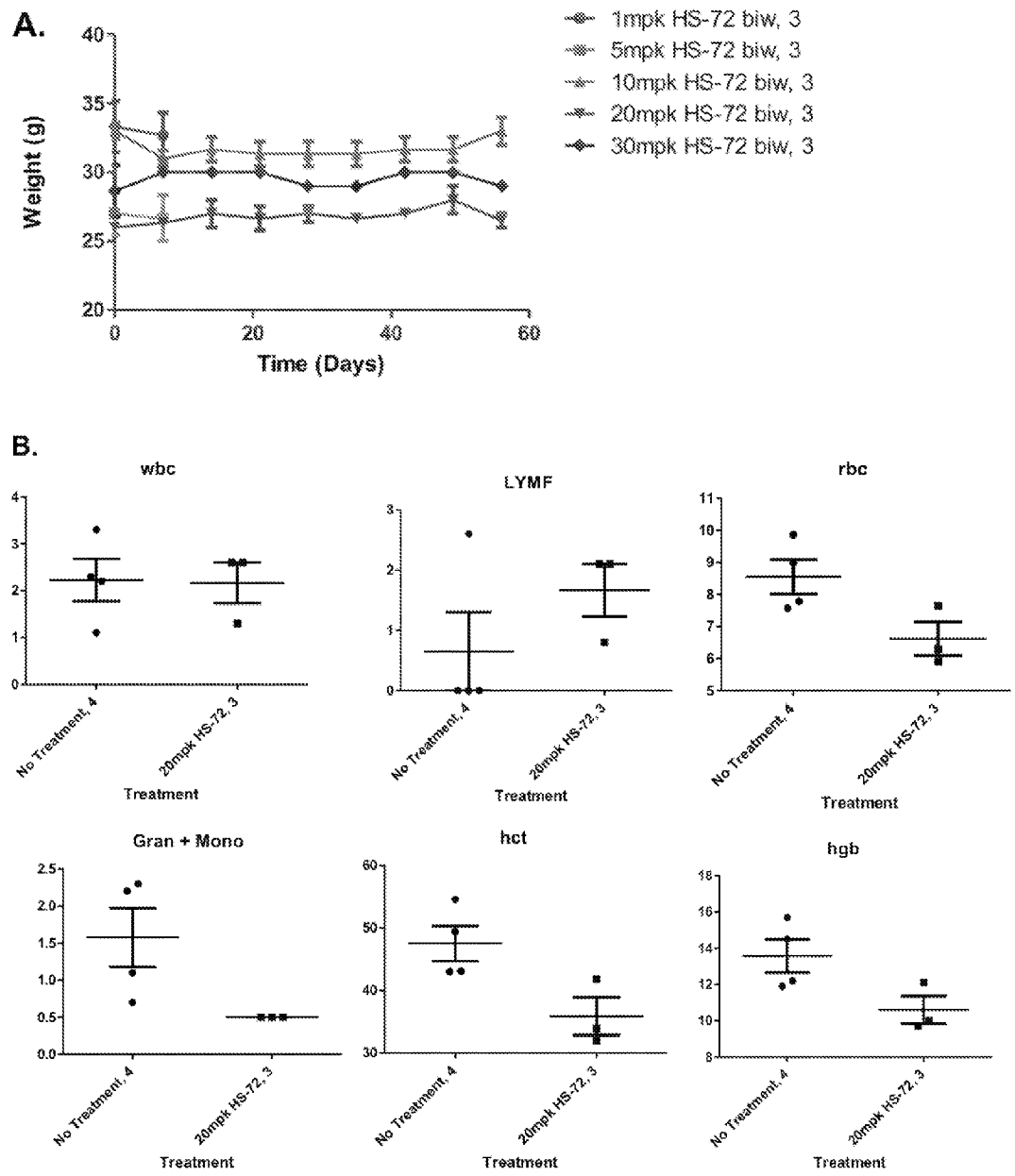
FIG. 14 shows (A) MTD shows that HS72 is well tolerated by wild-type mice and is not toxic at any of the doses tested. The 1 mpk and 5 mpk doses were abandoned after no immediate toxicity at the higher doses. (B) Complete blood count (CBC) analysis following HS-72 treatment shows no adverse effect of HS-72. wbc—White blood cell count. LYMF—lymphocytes. rbc—red blood cell count. Gran+Mono—Granuloctye+Monocyte count. hct—hematocrit. hgb—hemoglobin. (C) Liver test following HS-72 treatment showing no adverse effects. ast—aspartate transaminase. alt—alanine transaminase. alb—albumin. alkp—alkaline phosphatase. (D) Kidney test following HS-72 treatment showing no adverse effects. bun—blood urea nitrogen. cl—chloride. na—sodium. k—potassium. crea—creatinine. (E) Structure of HS-156 that was used an the internal standard for the PK study of plasma, liver, and kidney. (F) Plasma samples plotted on standard curve, which was used to calculate concentration of HS-72 in each sample. (G) Kidney samples plotted on standard curve, which was used to calculate concentration of HS-72 in each sample. (H) Liver samples plotted on standard curve, which was used to calculate concentration of HS-72 in each sample. (F-H) Ratio of area under the curve from EIC of HS-72 compared to HS-156 was plotted on the standard curve, which was used to determine concentration of HS-72 in plasma samples. Concentration in solution for all samples adjusted for a 1:4 dilution factor that was used when processing the samples. Final concentration of HS-72 in plasma was calculated per mL of plasma. Final concentration of HS-72 in the kidney and liver was calculated per gram of tissue using the weight of each tissue measured before sample processing. (I) HS-72 inhibits proliferation of a MMTV-neu derived cell line, NF639, at 25 uM and 50 uM at 24, 48, and 72 hours. (J) Combination treatment of HS-72 and HS-10 shows synergistic inhibition of NF639 cell proliferation. (***, p<0.001).
Figure 14:
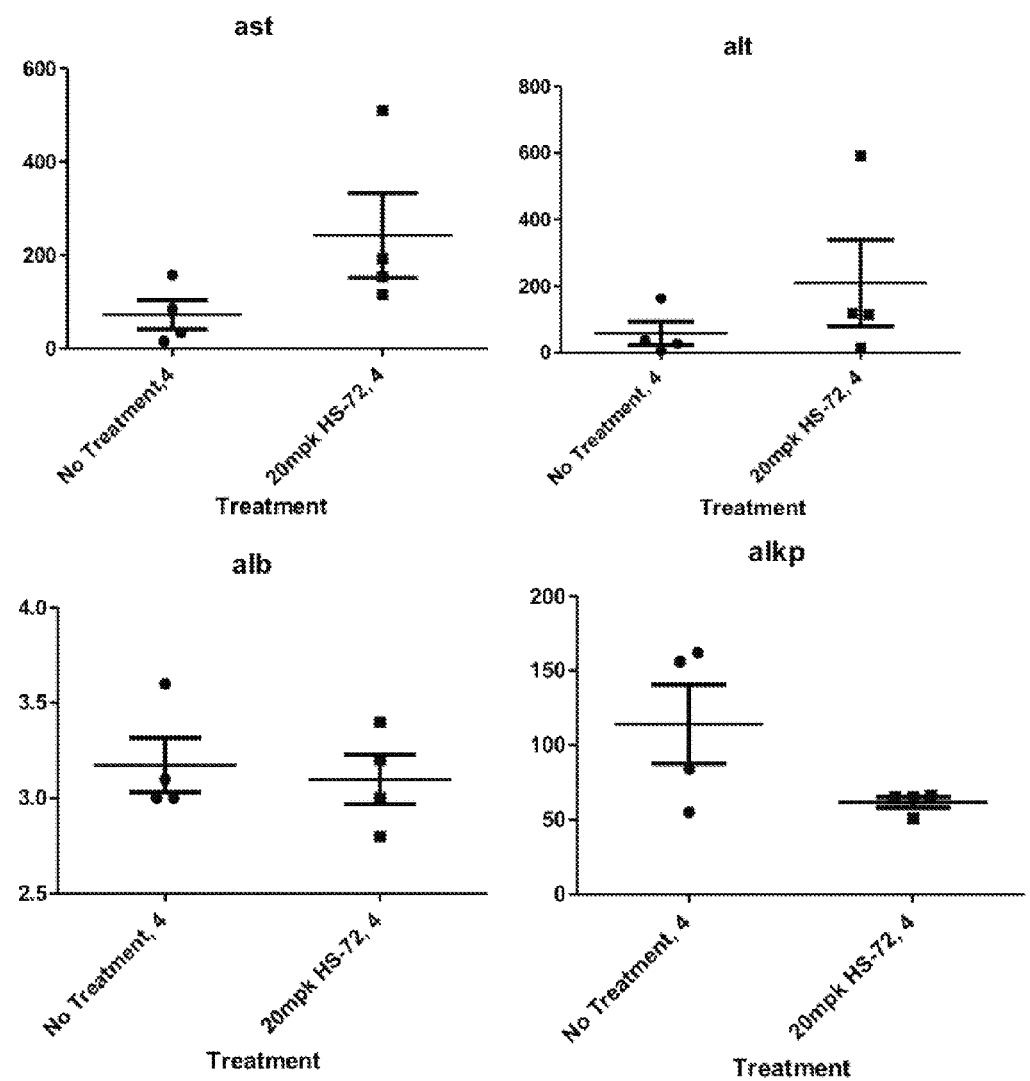
Figure 14:
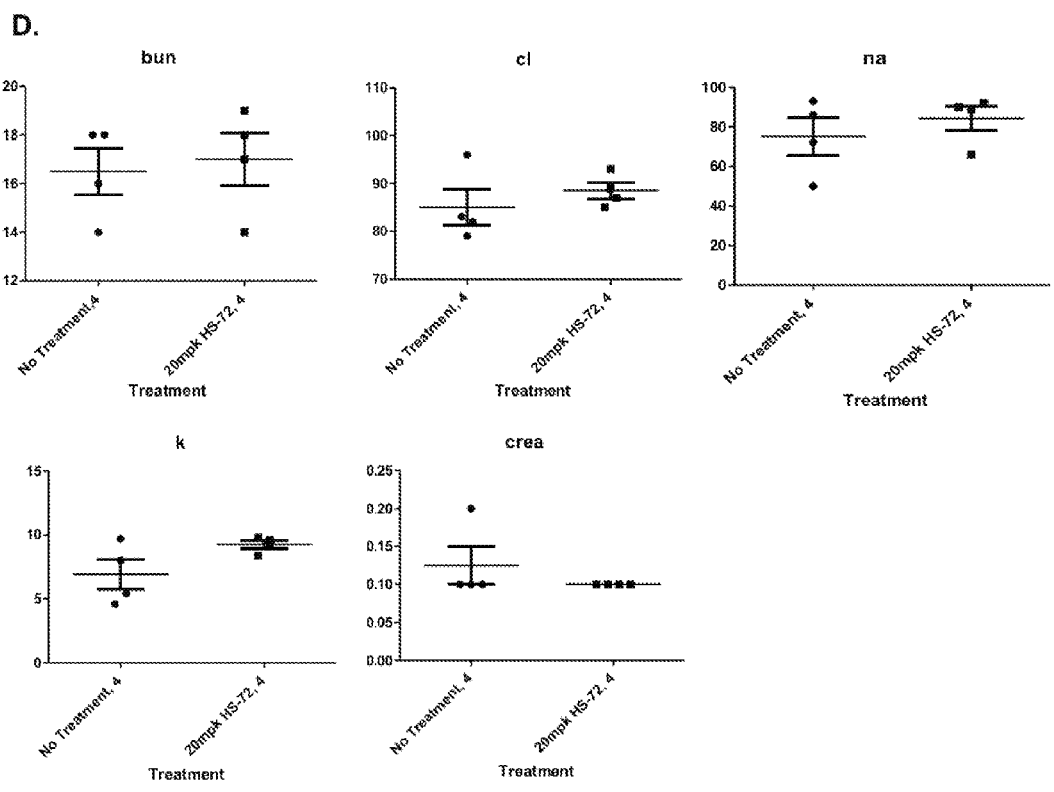
Figure 14:
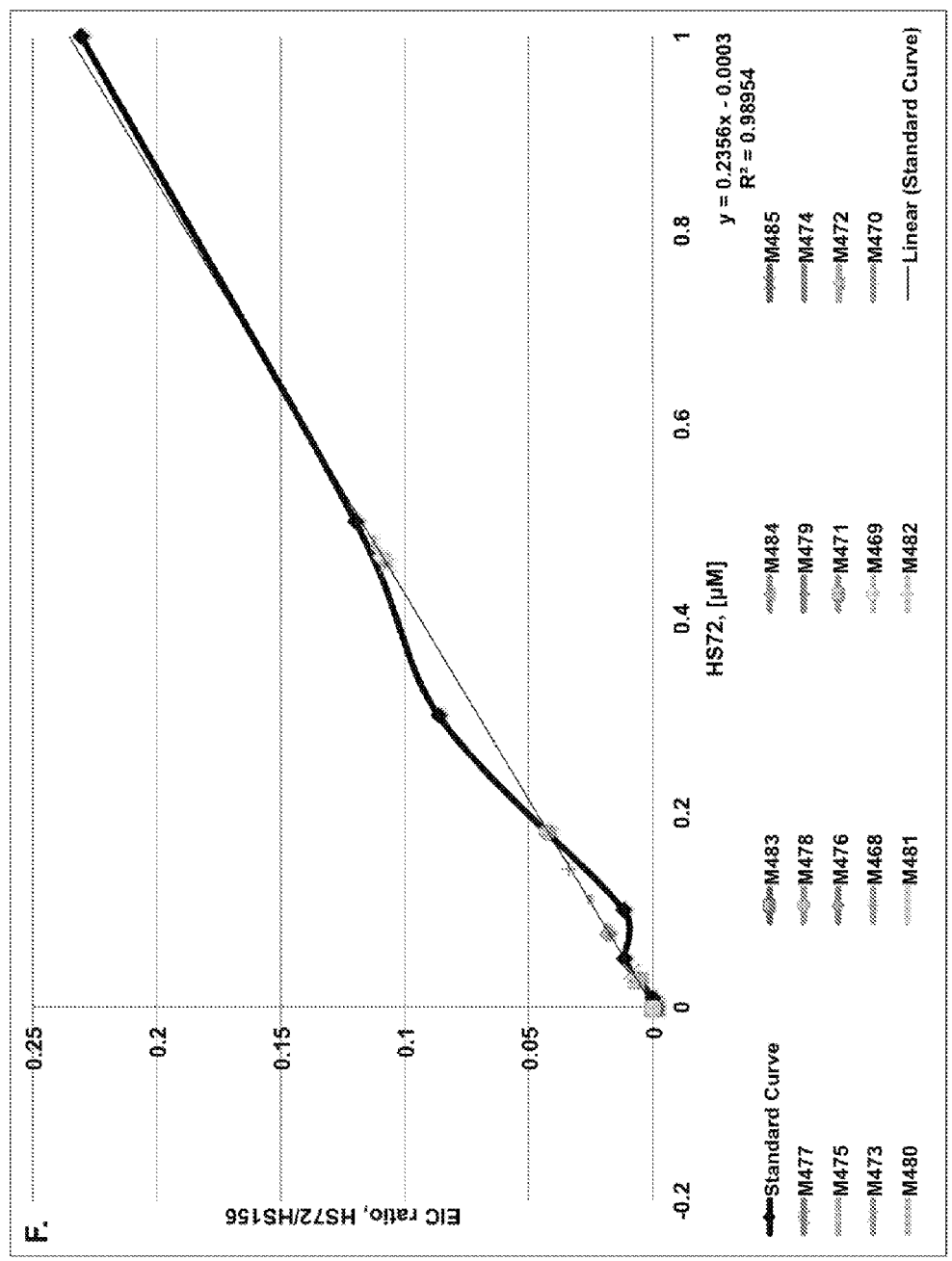
Figure 14:
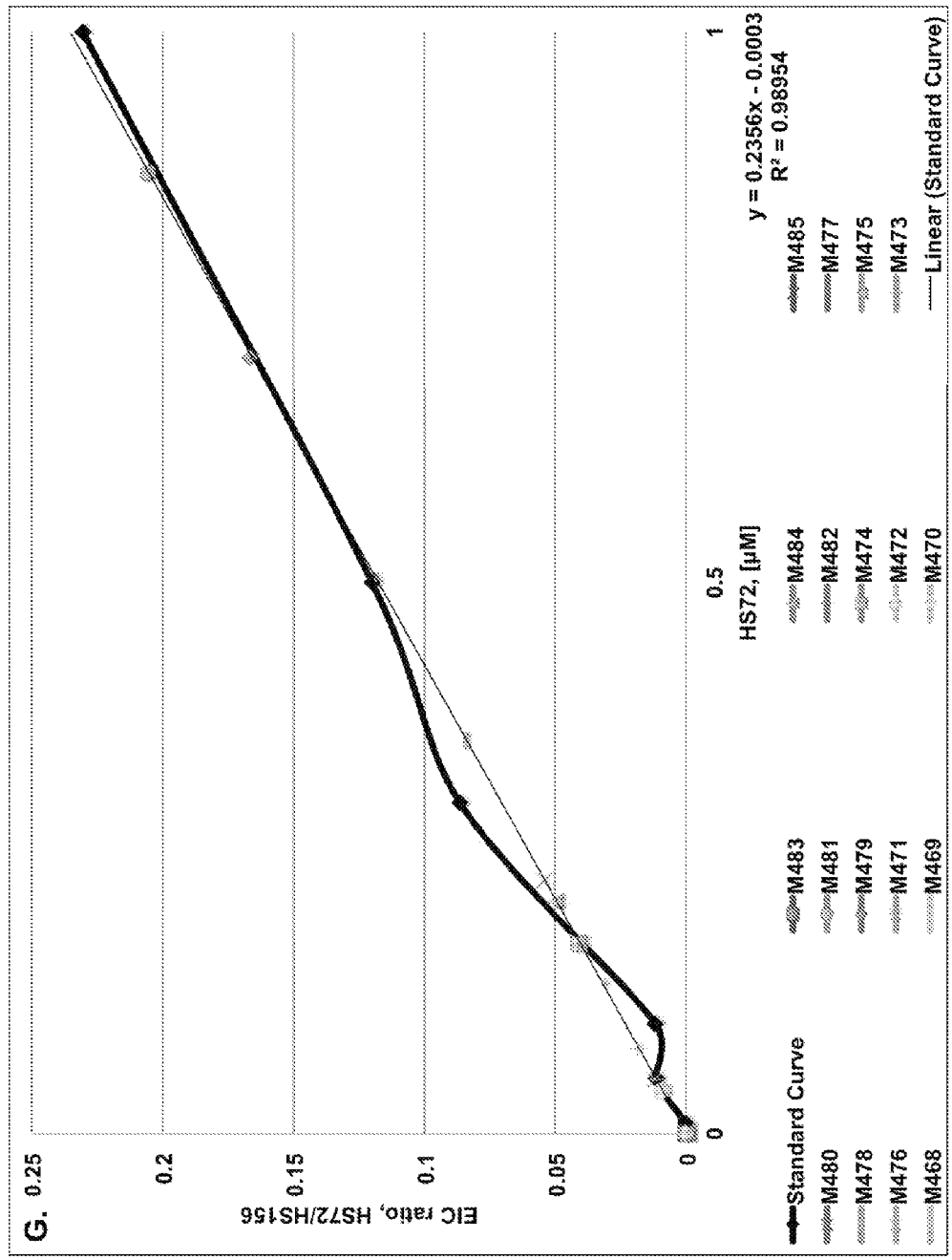
Figure 14:
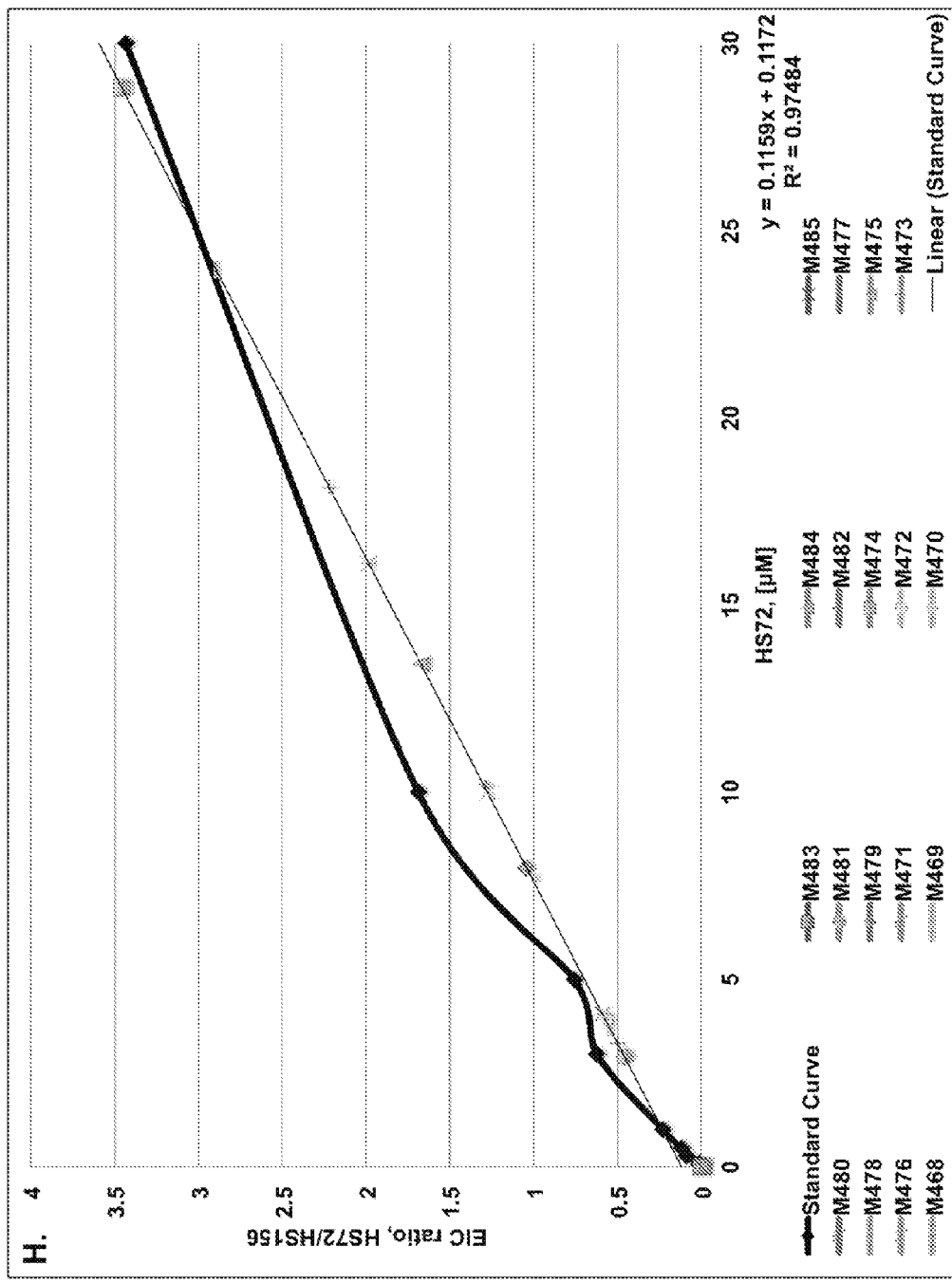
Figure 14:
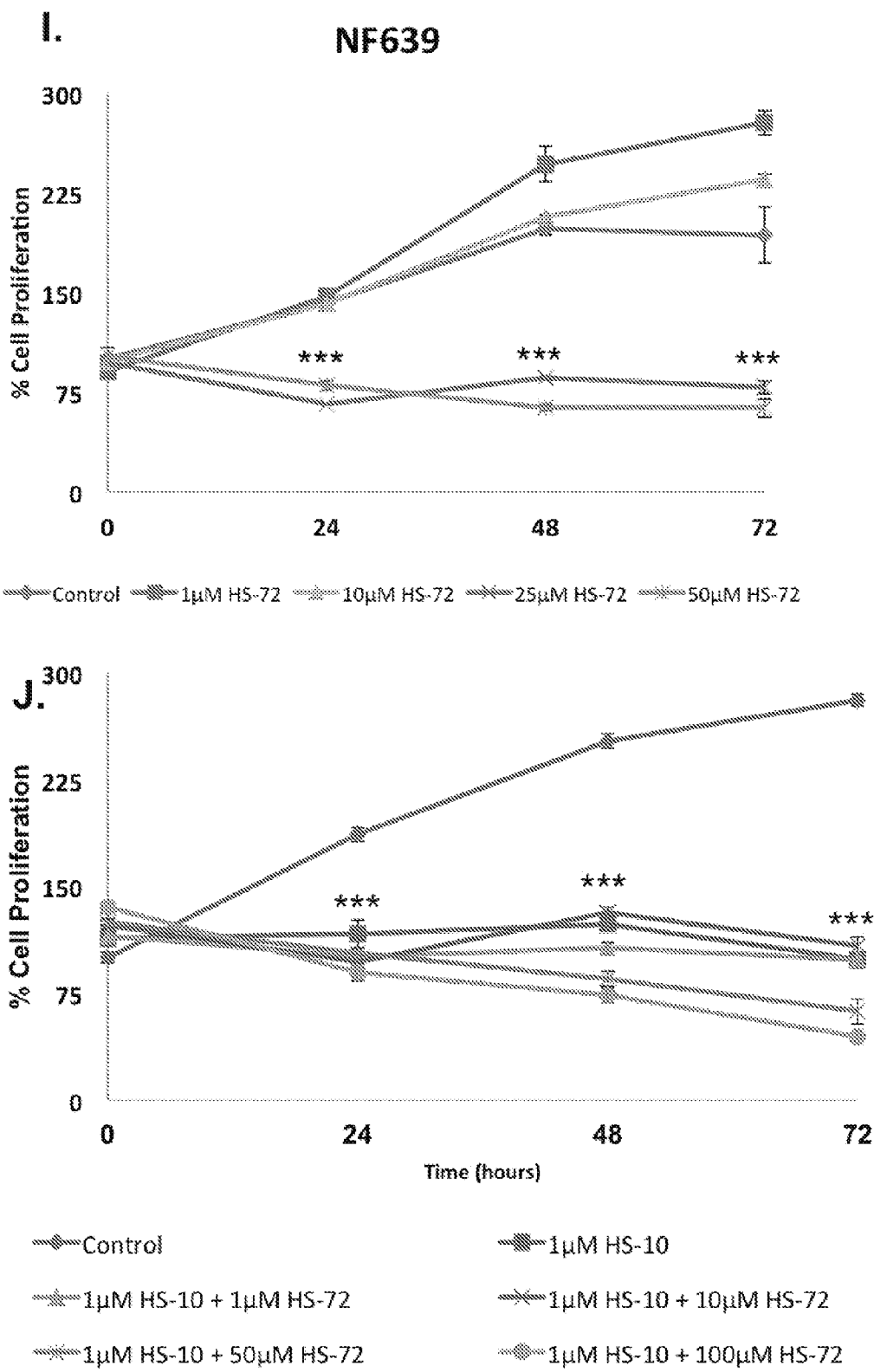

HS-72 is bioavailable in vivo and reduces tumor growth in a spontaneous mouse mammary tumor model. Prior to testing the efficacy of HS-72 in vivo, a preliminary experiment was performed to assess dose dependent effects in wild type mice. Healthy wild-type mice were dose escalated biweekly for 35 days and no adverse events, reduction in body weight, or altered behavior were observed up to 30 mg/kg (FIG. 14A). Additionally, a complete blood workup was done following HS-72 treatment in wild-type mice. Mice that were treated with HS-72 showed no effect on complete blood count, no effect on kidney function, and no effect on liver function compared to control mice (FIG. 14B-D). These data indicate that HS-72 is not toxic to wild-type mice. A limited PK study was also performed using wild-type mice, analyzing and quantifying HS-72 in the plasma, liver, and kidney. Each sample was spiked with an internal standard, HS-156 and analyzed by LC-MS (FIG. 14E). The ratio of the extracted ion chromatogram (EIC) comparing HS-72 to HS-156 was plotted on a standard curve to quantify [HS-72] present in each sample (FIG. 14F-H). FIG. 7A indicates that HS-72 is exponentially cleared from the plasma ($T_{1/2}$ elimination=0.4±0.1 hours n=3, SEM) reaching 0.07±0.03 mmol/ml (n=3, SEM) by 5 minutes post IP injection, clearing to 0.002±0.0002 mmol/ml (n=3, SEM) by 8 hours, with only trace amounts detectable (<10 nmol/ ml) by 24 hours. In kidney, HS-72 reached 0.43±0.08 mmol/gram tissue (w.w.) (n=3, SEM) at 5 minutes and by 24 hours was retained at 0.02±0.004 mmol/g (w.w.) (n=3, SEM) (FIG. 7B). In contrast, in liver HS-72 uptake peaked by 8 hours at 2.26±0.50 mmol/g (w.w.) (n=3, SEM) and was slowly cleared to 0.51±0.11 mmol/g (w.w.) (n=3, SEM) by 24 hours (FIG. 7C). These findings show plasma HS-72 present at significant levels for at least 8 hours post I.P. and that HS-72 has a high degree of tissue bioavailability. In all 3 compartments, the parent MS ion of 365.2 Da was detected intact, with no evidence of rapid metabolism. The finding that HS-72 is absorbed to high [μM] levels following IP injection at 20 mg/Kg, particularly in liver, as well as kidney without adverse event, suggests the molecule is well tolerated in vivo.

The apparent safety and bioavailability of HS-72 allowed testing the efficacy of HS-72 to reduce tumor growth in the MMTV-neu breast cancer model. In this model, HER2 is overexpressed under the transcriptional control of the mouse mammary tumor virus promoter/enhancer, leading to spontaneous development of mammary tumors [Taneja et al., 2009]. To confirm that HS-72 would have efficacy in the MMTV-neu mouse model, HS-72 was tested in the NF639 cell line, which is derived from the mammary tumor of a MMTV-neu mouse. HS-72 was shown to potently inhibit proliferation in a manner similar to previously tested cell lines (FIG. 14I). Furthermore, a synergistic effect on cell proliferation was observed when testing HS-72 and HS-10 in combination, thus highlighting the potential for combination therapy in the MMTV-neu mouse model (FIG. 14J). Tumor bearing MMTV-neu mice were treated I.P. with HS-72 at 20 mg/kg (mpk) on a biweekly (BiW) schedule for 21 days. At 21 days there is a significant reduction (p<0.05) in tumor volume in the HS-72 treated mice compared to untreated mice (FIG. 7D). A linear regression analysis comparing the slopes of the HS-72 tumor volume vs. no treatment tumor volume is trending towards significance (p=0.08) (FIG. 7D). Furthermore, median survival of animals increased by 6 days in mice treated with HS-72 20 mpk BiW, and by 13 days in animals treated with HS-72 20 mpk qd (daily dosing) (FIG. 7E). Collectively, these studies show that the HS-72 scaffold has no overt toxicities, exhibits tissue and tumor bioavailability, and demonstrates efficacy in a spontaneous mouse mammary tumor model even under conservative biweekly dosing conditions.

7. Exemplary Embodiments

For reasons of completeness, various aspects of the disclosure are set out in the following numbered clauses:

Clause 1. A compound of formula (I) as defined herein, or a pharmaceutically acceptable salt thereof, wherein $X^1$, $X^2$, $X^3$, $X^4$, $X^5$, $X^6$, $X^7$, $X^8$, $X^9$, and $X^{10}$ are each independently selected from the group consisting of N and $C(R^3)$; $Y^1$ and $Y^5$ are each independently selected from the group consisting of N and $C(R^4)$; $Y^2$, $Y^3$, $Y^4$, and $Y^6$ are each independently selected from the group consisting of a bond, O, S, $N(R^5)$, and $C(R^6R^7)$, provided no more than one of $Y^2$, $Y^3$, $Y^4$, and $Y^6$ is a bond, and provided that at least two of $Y^2$, $Y^3$, $Y^4$, and $Y^6$ are $C(R^4)$; $R^1$ is hydrogen, alkyl, haloalkyl, hydroxyalkyl, alkoxyalkyl, haloalkoxyalkyl, aminoalkyl, alkylaminoalkyl, di(alkyl)aminoalkyl, or cyanoalkyl; $R^2$ is alkyl, haloalkyl, hydroxyalkyl, alkoxyalkyl, haloalkoxyalkyl, aminoalkyl, alkylaminoalkyl, di(alkyl)aminoalkyl, or cyanoalkyl; and $R^3$, $R^4$, $R^5$, $R^6$, and $R^7$, at each occurrence, are each independently selected from the group consisting of hydrogen, halogen, alkyl, haloalkyl, hydroxyalkyl, alkoxy- alkyl, haloalkoxyalkyl, aminoalkyl, alkylaminoalkyl, di(alkyl)aminoalkyl, cyanoalkyl, alkoxy, haloalkoxy, cyano, hydroxy, amino, alkylamino, and di(alkyl)amino.

Clause 2. The compound of clause 1, wherein $X^1$ is N.

Clause 3. The compound of clause 1 or clause 2, wherein $X^2$, $X^3$, $X^4$, and $X^5$ are each $C(R^3)$.

Clause 4. The compound of any one of clauses 1-3, wherein $X^2$ is CH; $X^3$ is CH; $X^4$ is CH; and $X^5$ is CH.

Clause 5. The compound of any one of clauses 1-4, wherein $X^6$ is N; $X^7$ is $C(R^3)$; $X^8$ is $C(R^3)$; $X^9$ is N; and $X^{10}$ is $C(R^3)$.

Clause 6. The compound of any one of clauses 1-5, wherein $X^6$ is N; $X^7$ is CH; $X^8$ is CH; $X^9$ is N; and $X^{10}$ is CH.

Clause 7. The compound of any one of clauses 1-6, wherein $Y^1$ is N; $Y^2$ is $C(R^6R^7)$; $Y^3$ is $C(R^6R^7)$; $Y^4$ is $C(R^6R^7)$; $Y^5$ is $C(R^4)$; and $Y^6$ is $C(R^6R^7)$.

Clause 8. The compound of any one of clauses 1-7, wherein $Y^1$ is N; $Y^2$ is $CH_2$; $Y^3$ is $CH_2$; $Y^4$ is $CH_2$; $Y^5$ is CH; and $Y^6$ is $CH_2$.

Clause 9. The compound of any one of clauses 1-8, wherein $R^1$ is hydrogen.

Clause 10. The compound of any one of clauses 1-9, wherein $R^2$ is $C_1$-$C_{10}$-alkyl.

Clause 11. The compound of any one of clauses 1-10, wherein $R^2$ is n-propyl.

Clause 12. The compound of clause 1, having formula (I-a),

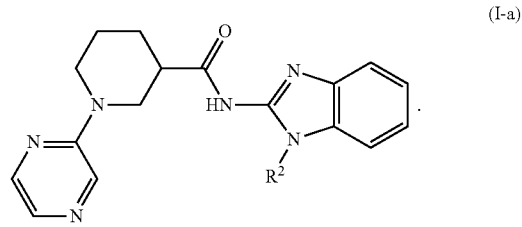

Clause 13. The compound of clause 1, having formula (I-b),

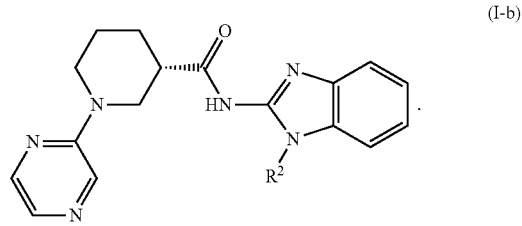

Clause 14. The compound of clause 1, having formula (I-c),

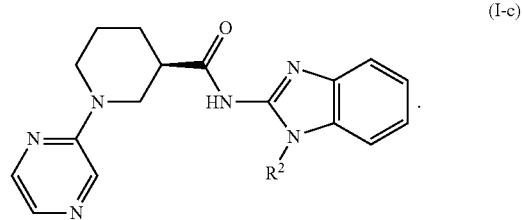

Clause 15. The compound of any one of clauses 12-14, wherein $R^2$ is $C_1$-$C_{10}$-alkyl.

Clause 16. The compound of any one of clauses 12-15, wherein $R^2$ is n-propyl.

Clause 17. The compound of clause 1, having formula (I-d),

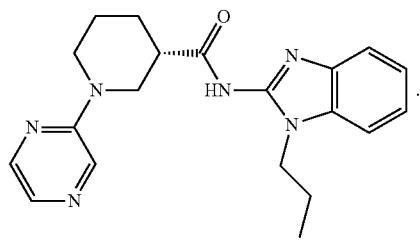

Clause 18. A pharmaceutical composition comprising a compound according to any one of clauses 1-17 and at least one pharmaceutically acceptable carrier.

Clause 19. The pharmaceutical composition of clause 18, further comprising an Hsp90 inhibitor (e.g., 2-(((1R,4R)-4-hydroxycyclohexyl)amino)-4-(3,6,6-trimethyl-4-oxo-4,5,6,7-tetrahydro-1H-indazol-1-yl)benzamide).

Clause 20. A method of the inhibiting the inducible form of heat shock protein 70 ("HSP70i"), comprising administering to a subject in need thereof a therapeutically effective amount of a compound according to any one of clauses 1-17, or a pharmaceutically acceptable salt thereof.

Clause 21. A method of inhibiting tumor growth, comprising administering to a subject in need thereof a therapeutically effective amount of a compound according to any one of clauses 1-17, or a pharmaceutically acceptable salt thereof.

Clause 22. A method of treating cancer, comprising administering to a subject in need thereof a therapeutically effective amount of a compound according to any one of clauses 1-17, or a pharmaceutically acceptable salt thereof.

Clause 23. The method of clause 22, wherein the cancer is breast cancer, prostate cancer, non-small cell lung cancer, colorectal cancer, pancreatic cancer, ovarian cancer, melanoma, or a combination thereof.

Clause 24. A method of treating Huntington's disease, comprising administering to a subject in need thereof a therapeutically effective amount of a compound according to any one of clauses 1-17, or a pharmaceutically acceptable salt thereof.

Clause 25. The method of any one of clauses 20-24, further comprising administering a therapeutically effective amount of an Hsp90 inhibitor (e.g., 2-(((1R,4R)-4-hydroxycyclohexyl)amino)-4-(3,6,6-trimethyl-4-oxo-4,5,6,7-tetrahydro-1H-indazol-1-yl)benzamide).

Clause 26. Use of a compound according to any one of clauses 1-17 in the manufacture of a medicament for inhibiting the inducible form of heat shock protein 70 ("HSP70i").

Clause 27. Use of a compound according to any one of clauses 1-17 in the manufacture of a medicament for inhibiting tumor growth.

Clause 28. Use of a compound according to any one of clauses 1-17 in the manufacture of a medicament for treating cancer.

Clause 29. Use of a compound according to any one of clauses 1-17 in the manufacture of a medicament for treating breast cancer, prostate cancer, non-small cell lung cancer, colorectal cancer, pancreatic cancer, ovarian cancer, melanoma, or a combination thereof.

Clause 30. Use of a compound according to any one of clauses 1-17 in the manufacture of a medicament for treating Huntington's disease.

Clause 31. The use according to any one of clauses 26-30, further comprising use of an Hsp90 inhibitor (e.g., 2-(((1R,4R)-4-hydroxycyclohexyl)amino)-4-(3,6,6-trimethyl-4-oxo-4,5,6,7-tetrahydro-1H-indazol-1-yl)benzamide) in the manufacture of the medicament.

Clause 32. A compound of formula (II),

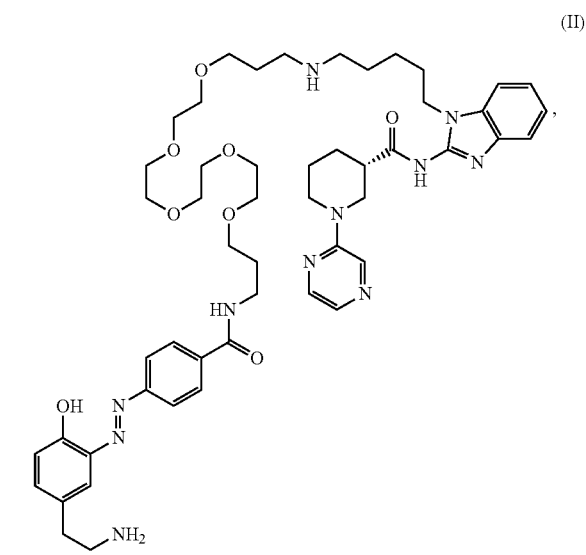 [SMILES: NCCc1ccc(O)c(/N=N/c2ccc(C(=O)NCCCOCCOCCOCCOCCOCCCNCCCCCn3c(NC(=O)[C@H]4CCCN(c5cnccn5)C4)nc4ccccc43)cc2)c1]

or a pharmaceutically acceptable salt thereof.

Clause 33. A method of using the compound according to clause 32 for detecting Hsp70 in a sample.

Clause 34. The method of clause 33, wherein the Hsp70 is Hsp70i.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A compound of formula (I), or a pharmaceutically acceptable salt or tautomer thereof,

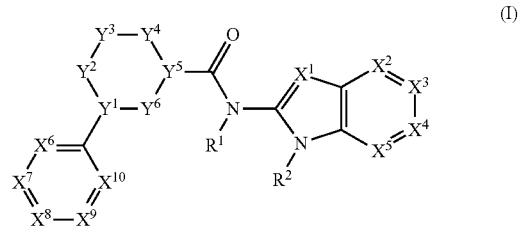

wherein
X¹ is N;
X², X³, X⁴, and X⁵ are CR³;
X⁶, X⁷, X⁸, X⁹, and X¹⁰ are each independently selected from the group consisting of N and C(R³);
Y¹ is N;
Y² is CH₂;
Y³ is CH₂;
Y⁴ is CH₂;
Y⁵ is CH with either (S) or (R) stereochemistry;
Y⁶ is CH₂;
R¹ is hydrogen, alkyl, haloalkyl, hydroxyalkyl, alkoxyalkyl, haloalkoxyalkyl, aminoalkyl, alkylaminoalkyl, di(alkyl)aminoalkyl, or cyanoalkyl;
R² is alkyl, haloalkyl, hydroxyalkyl, alkoxyalkyl, haloalkoxyalkyl, aminoalkyl, alkylaminoalkyl, di(alkyl)aminoalkyl, or cyanoalkyl; and
R³, at each occurrence, are each independently selected from the group consisting of hydrogen, halogen, alkyl, haloalkyl, hydroxyalkyl, alkoxyalkyl, haloalkoxyalkyl, aminoalkyl, alkylaminoalkyl, di(alkyl)aminoalkyl, cyanoalkyl, alkoxy, haloalkoxy, cyano, hydroxy, amino, alkylamino, and di(alkyl)amino.

2. The compound of claim 1, or a pharmaceutically acceptable salt or tautomer thereof, wherein X² is CH; X³ is CH; X⁴ is CH; and X⁵ is CH.

3. The compound of claim 1, or a pharmaceutically acceptable salt or tautomer thereof, wherein X⁶ is N; X⁷ is C(R³); X⁸ is C(R³); X⁹ is N; and X¹⁰ is C(R³).

4. The compound of claim 1, or a pharmaceutically acceptable salt or tautomer thereof, wherein X⁶ is N; X⁷ is CH; X⁸ is CH; X⁹ is N; and X¹⁰ is CH.

5. The compound of claim 1, or a pharmaceutically acceptable salt or tautomer thereof, wherein R¹ is hydrogen.

6. The compound of claim 1, or a pharmaceutically acceptable salt or tautomer thereof, wherein R² is C₁-C₁₀-alkyl.

7. The compound of claim 1, having formula (I-d), or a pharmaceutically acceptable salt or tautomer thereof,

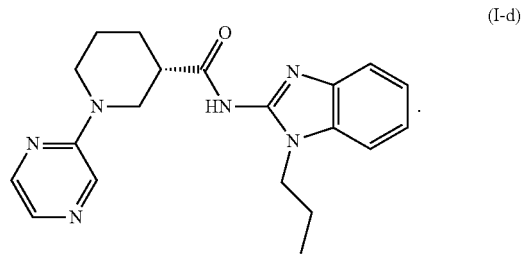 [SMILES: CCCn1c(NC(=O)[C@H]2CCCN(c3cnccn3)C2)nc2ccccc21]

(I-d)

8. A pharmaceutical composition comprising a compound according to claim 1, or a pharmaceutically acceptable salt or tautomer thereof, and at least one pharmaceutically acceptable carrier.

9. A method of the inhibiting the inducible form of heat shock protein 70 ("HSP70i"), comprising administering to a subject in need thereof a therapeutically effective amount of a compound according to claim 1, or a pharmaceutically acceptable salt thereof.

10. A method of inhibiting tumor growth, comprising administering to a subject in need thereof a therapeutically effective amount of a compound according to claim 1, or a pharmaceutically acceptable salt thereof.

* * * * *